US006667344B2

(12) United States Patent
Banerjee et al.

(10) Patent No.: US 6,667,344 B2
(45) Date of Patent: Dec. 23, 2003

(54) BRONCHODILATING COMPOSITIONS AND METHODS

(75) Inventors: Partha S. Banerjee, Davis, CA (US); Stephen Pham, Sacramento, CA (US); Samuel O. Akapo, Vacaville, CA (US); Imtiaz A. Chaudry, Napa, CA (US)

(73) Assignee: Dey, L.P., Napa, CA (US)

( * ) Notice: Subject to any disclaimer, the term of this patent is extended or adjusted under 35 U.S.C. 154(b) by 0 days.

(21) Appl. No.: 09/887,281

(22) Filed: Jun. 22, 2001

(65) Prior Publication Data

US 2002/0151597 A1 Oct. 17, 2002

Related U.S. Application Data

(60) Provisional application No. 60/284,606, filed on Apr. 17, 2001.

(51) Int. Cl.$^7$ .................................................. A61K 31/35
(52) U.S. Cl. .............................. 514/653; 424/45; 424/46
(58) Field of Search ...................... 424/45, 46; 514/653

(56) References Cited

U.S. PATENT DOCUMENTS

| 3,994,974 A | 11/1976 | Murakami et al. .......... 260/562 |
| 4,335,121 A | 6/1982 | Phillipps et al. ............. 424/241 |
| 4,992,474 A | 2/1991 | Skidmore et al. ........... 514/653 |
| 5,033,252 A | 7/1991 | Carter .......................... 53/425 |
| 5,052,558 A | 10/1991 | Carter ......................... 206/439 |
| 5,126,375 A | 6/1992 | Skidmore et al. ........... 514/651 |
| 5,225,445 A | 7/1993 | Skidmore et al. ........... 514/651 |
| 5,270,305 A | 12/1993 | Palmer ........................ 514/171 |
| 5,290,815 A | 3/1994 | Johnson et al. ............. 514/651 |
| 5,323,907 A | 6/1994 | Kalvelage ................... 206/531 |
| 5,525,623 A | 6/1996 | Spear et al. ................. 514/423 |
| 5,602,110 A | 2/1997 | Drumm et al. ................ 514/47 |
| 5,654,276 A | 8/1997 | Barrett et al. ................. 514/13 |
| 5,668,110 A | 9/1997 | Barrett et al. ................. 514/13 |
| 5,674,860 A | 10/1997 | Carling et al. .............. 514/171 |
| 5,677,280 A | 10/1997 | Barrett et al. ................. 514/14 |
| 5,677,809 A | 10/1997 | Kadlec ..................... 360/78.09 |
| 5,683,983 A | 11/1997 | Barrett et al. ................. 514/12 |
| 5,691,336 A | 11/1997 | Dorn et al. ............... 514/236.2 |
| 5,733,526 A | 3/1998 | Trevino et al. ............. 424/9.52 |
| 5,750,549 A | 5/1998 | Caldwell et al. ............ 514/364 |
| 5,780,467 A | 7/1998 | Dorn et al. ............... 514/236.2 |
| 5,795,564 A | 8/1998 | Aberg et al. .................. 424/45 |
| 5,874,063 A | 2/1999 | Briggner et al. .............. 424/45 |
| 5,874,481 A | 2/1999 | Weers et al. ................. 514/761 |
| 5,877,191 A | 3/1999 | Caldwell et al. ............ 514/337 |
| 5,929,094 A | 7/1999 | Durette et al. .............. 514/340 |
| 5,965,622 A | 10/1999 | Senanayake ................ 514/653 |
| 5,972,919 A | * 10/1999 | Carling et al. .............. 514/171 |
| 5,980,949 A | 11/1999 | Trofast ........................ 424/489 |
| 5,983,956 A | 11/1999 | Trofast ............................ 141/1 |
| 6,004,537 A | 12/1999 | Blondino et al. .............. 424/45 |
| 6,030,604 A | 2/2000 | Trofast ......................... 424/46 |
| 6,040,344 A | * 3/2000 | Gao et al. .................... 514/554 |
| 6,041,777 A | 3/2000 | Faithfull et al. ........ 128/200.24 |
| 6,068,833 A | 5/2000 | Aberg et al. .................. 424/45 |
| 6,071,971 A | 6/2000 | Senanayake ................ 514/653 |
| 6,126,919 A | 10/2000 | Stefely et al. ................. 424/45 |
| 6,136,603 A | 10/2000 | Dean et al. .................. 435/375 |
| 6,150,418 A | * 11/2000 | Hochrainer et al. ......... 514/630 |
| 6,161,536 A | * 12/2000 | Redmon et al. ......... 128/200.14 |
| 6,235,725 B1 | * 5/2001 | Ahmed ......................... 514/54 |
| 6,261,539 B1 | * 7/2001 | Adjei et al. ................... 424/46 |
| 6,287,540 B1 | 9/2001 | Trofast ......................... 424/46 |
| 6,303,145 B2 | * 10/2001 | Jerussi et al. ............... 424/464 |
| 6,369,115 B1 | 4/2002 | Ward .......................... 514/728 |
| 6,461,591 B1 | * 10/2002 | Keller et al. .................. 424/45 |
| 6,481,435 B2 | 11/2002 | Hochrainer et al. ... 128/200.14 |
| 2001/0024641 A1 | 9/2001 | Yang ............................ 424/46 |
| 2002/0032149 A1 | 3/2002 | Kensey ......................... 514/1 |
| 2002/0061835 A1 | 5/2002 | Kensey ......................... 514/1 |
| 2002/0081266 A1 | 6/2002 | Woolfe et al. ................ 424/46 |
| 2002/0099013 A1 | 7/2002 | Piccariello et al. .......... 514/12 |
| 2002/0103260 A1 | 8/2002 | Clarke et al. ............... 514/630 |
| 2002/0151597 A1 | 10/2002 | Banerjee et al. ........... 514/629 |

FOREIGN PATENT DOCUMENTS

| DE | 2305092 | 2/1973 |
| DE | 19541689 | 5/1996 |
| DE | 19835346 | 2/2000 |
| EP | 0370632 | 5/1990 |
| EP | 1157689 | 11/2001 |
| EP | 1229034 | 8/2002 |

(List continued on next page.)

OTHER PUBLICATIONS

Bartow and Brogden, "An Update of its Pharmacological Properties and Therapeutic Efficacy in the Management of Asthma," *Drugs*, 55(2):303–322 (1998).

Campbell et al, "An comparison of the efficacy of long–acting B2–agonists: eformoterol via Turbohaler(R) and salmeterol via pressurized metered dose inhaler or Accuhaler (R), in mild to moderate asthmatics," *Respiratory Medicine*, 93:236–244 (1999).

Dellamary et al, "Hollow Porous Particles in Metered Dose Inhalers," *Pharmaceutical Research*, 17(2):168–174 (2000).

Derwent#000971705, WPI Acc. No. 1973–48969U/197335 citing German Patent Application No. DE 2305092 A, "Alpha–aminomethylbenzyl alcohol derivs–prepd. by redn. of corresponding protected derivs."

(List continued on next page.)

*Primary Examiner*—Kevin E. Weddington
(74) *Attorney, Agent, or Firm*—Heller Ehrman White & McAuliffe LLP; Stephanie Seidman; Dale Rieger

(57) ABSTRACT

Bronchodilating compositions and methods are provided. The compositions are intended for administration as a nebulized aerosol. In certain embodiments, the compositions contain formoterol, or a derivative thereof. Methods for treatment, prevention, or amelioration of one or more symptoms of bronchoconstrictive disorders using the compositions provided herein are also provided.

88 Claims, No Drawings

FOREIGN PATENT DOCUMENTS

| | | |
|---|---|---|
| WO | 9311773 | 6/1993 |
| WO | 9505805 | 3/1995 |
| WO | 9531964 | 11/1995 |
| WO | 9618384 | 6/1996 |
| WO | 9619198 | 6/1996 |
| WO | 9619968 | 7/1996 |
| WO | 9632095 | 10/1996 |
| WO | 9805302 | 2/1998 |
| WO | 9815280 | 4/1998 |
| WO | 9831351 | 7/1998 |
| WO | 9831352 | 7/1998 |
| WO | 9834595 | 8/1998 |
| WO | 9834596 | 8/1998 |
| WO | 9841193 | 9/1998 |
| WO | 9900134 | 1/1999 |
| WO | 9915182 | 4/1999 |
| WO | 9925359 | 5/1999 |
| WO | 9930703 | 6/1999 |
| WO | 9900134 | 7/1999 |
| WO | 9936095 | 7/1999 |
| WO | 9940939 | 8/1999 |
| WO | 9948476 | 9/1999 |
| WO | 9961003 | 12/1999 |
| WO | 0000181 | 1/2000 |
| WO | 0006121 | 2/2000 |
| WO | 0007567 | 2/2000 |
| WO | 0016814 | 3/2000 |
| WO | 0023037 | 4/2000 |
| WO | 0028979 | 5/2000 |
| WO | 0030612 | 6/2000 |
| WO | 0030613 | 6/2000 |
| WO | 0033892 | 6/2000 |
| WO | 0047200 | 8/2000 |
| WO | 0048587 | 8/2000 |
| WO | 0051591 | 8/2000 |
| WO | 0053187 | 9/2000 |
| WO | 0053188 | 9/2000 |
| WO | 0122956 | 4/2001 |
| WO | 0127107 | 4/2001 |
| WO | 0132163 | 5/2001 |
| WO | 0139745 | 6/2001 |
| WO | 0154664 | 8/2001 |
| WO | 0170198 | 9/2001 |
| WO | 0178735 | 10/2001 |
| WO | 0178737 | 10/2001 |
| WO | 0178745 | 10/2001 |
| WO | 0183517 | 11/2001 |
| WO | 0185137 | 11/2001 |
| WO | 0189491 | 11/2001 |
| WO | 0203958 | 1/2002 |
| WO | 0207672 | 1/2002 |
| WO | 0211803 | 2/2002 |
| WO | 0228368 | 4/2002 |
| WO | 0230394 | 4/2002 |
| WO | 0234237 | 5/2002 |
| WO | 0238107 | 5/2002 |
| WO | 0243806 | 6/2002 |
| WO | 0245682 | 6/2002 |
| WO | 0249616 | 6/2002 |
| WO | 02051483 | 7/2002 |
| WO | 02060532 | 8/2002 |
| WO | 02060533 | 8/2002 |
| WO | 02060875 | 8/2002 |
| WO | 02060896 | 8/2002 |
| WO | 02060898 | 8/2002 |
| WO | 02062317 | 8/2002 |
| WO | 1236467 | 9/2002 |
| WO | 02083113 | 10/2002 |

OTHER PUBLICATIONS

Ekstrom et al, "Low–dose formoterol Turbuhaler(R) (Oxis(R)) b.i.d., a 3–month placebo–controlled comparison with terbutaline (q.i.d.)," *Respiratory Medicine*, 92:1040–1045 (1998).

Kaumann and Lemoine, "Direct labelling of myocardial B1–adrenoceptors: Comparison of binding affinity of 3H–(—)–bisoprolol with its blocking potency," *Archives of Pharmacology*, 331:27–39 (1985).

Lecaillon et al, "Pharmacokinetics and tolerability of formoterol in healthy volunteers after a single high dose of Foradil by powder Inhalation via aerolizer (TM)," *European Journal Clinical Pharmacology*, 55:131–138 (1999).

Lemoine et al, "Direct labelling of B2–adrenoceptors; Comparison of binding potency of 3H–ICI 118, 551 and blocking potency of ICI 118,551," *Archives of Pharmacology*, 331:40–51 (1985).

Lotvall et al, "Similar bronchodilation with formoterol delivered by Aerolizer or Turbuhaler," *Can Respir J*, 6(5):412–416 (1999).

Nielsen et al, "Flow–dependent effect of formoterol dry–powder inhaled from the Aeolizer (R)," *Eur Respir J*, 10:2105–2109 (1997).

Nightingale et al, "Differential Effect of Formoterol on Adenosine Monophosphate and Histamine Reactivity in Asthma," *Am J Respir Crit Care Med*, 159:1786–1790 (1999).

Nogrady, T., (editor), Medicinal Chemistry: A Biochemical Approach, Oxford University Press, New York, pp. 388–392 (1985).

Palmqvist et al, "Inhaled dry–powder formoterol and salmeterol in asthmatic patients: onset of action, duration of effect and potency," *Eur Respir J*, 10:2484–2489 (1997).

Rico–Mendez et al, "Formoterol en polvo seco, dos veces al dia versus salbutamol aerosol, cuatro veces al dia, en pacientes con asma astable," *Revista Alergia Mexico*, XLV(5):130–135 (1999).

Ringdal et al, "Onset and duration of action of single doses of formoterol inhaled via Turbuhaler(R)," *Respiratory Medicine*, 92:1017–1021 (1998).

Schreurs et al, "A dose-repsonse study with formoterol Turbuhaler(R) as maintenance therapy in asthmatic patients," *Eur Respir J*, 9:1678–1683 (1996).

Seberova and Andersson, "Oxis(R) (formoterol given by Turbuhaler(R) showed as rapid an onset of action as salbutamol given by a pMDI," *Respiratory Medicine*, 94:607–611 (2000).

Selroos et al, "Delivery Devices for Inhaled Asthma Medication," *Clin Immunother*, 6:273–299 (1996).

Tomioka et al, "Anti–Allergic Activities of the B–Adrenoceptor Stimulant Formoterol (BD 40A)," *Arch Int Pharmacodyn*, 250:279–292 (1981).

Totterman et al, "Tolerability to high dose of formoterol and terbutaline via Turbuhaler(R) for 3 days in stable asthmatic patients," *Eur Respir J*, 12:573–579 (1998).

Ullman et al, "Formoterol inhaled as dry powder or via pressurized metered–dose inhaler in a cumulative dose–response study," *Allergy*, 51:745–748 (1996).

Barnes, P.J., "Scientific rationale for inhaled combination therapy with long–acting $6_2$–agonists and corticosteroids," *Eur. Respir. J.* 19:182–191 (2002).

Campestrini et al., "Automated and sensitive method for the determination of formoterol in human plasma by high–performance liquid chromatography and electrochemical detection," *Journal of Chromatography B* 704:221–229 (1997).

Cazzola et al., "Long–Acting $6_2$–Agonists in the Treatment of Acute Exacerbations of COPD," *Clin. Drug Invest.* 22(6):369–376 (2002).

Derwent#010743444, WPI Acc No.:1996–240399/199625 for German Patent Application DE 19541689, "Medicament contg. ciclesnoid and beta2–sympathomimetic–for treating chromic obstructive respiratory disease,".

Derwent#012030009, WPI Acc No.: 1998–446919–199838 for PCT Patent Application WO 98/34595, "Pressurized liquid aerosol propellant for pharmaceutical inhalers–contains carbon dioxide and hydro–fluoroalkane; gives more consistent dosing and a better particle size spectrum,".

Derwent#013011051, WPI Acc No.:2000–182903/200016 for PCT Patent Application WO 00/06121, "Aerosol propellant comprising dinitrogen monoxide and hydrofluroalkane and optionally containing a pharmaceutically active substance,".

Derwent#013023586, WPI Acc No.: 2000–195437/200017, for PCT Patent Application WO 00/07567 "Aerosol formulation for drug administration, containing small amount of cromoglycate or nedocromil salt as drug carrier, to improve dispersion stability and accuracy of dosing,".

Derwent#013024375, WPI Acc No.: 2000–196226/200018 for German Patent Application DE 19835346, "Two–part drug capsule for use in powder inhalers is formed from hydrophobic plastics, preferably high density polyethylene,".

Derwent#013227765, WPI Acc No. 2000–399639/200034, for PCT Patent Application, WO 00/28979 "Use of magnesium stearate for stabilization of dry powder inhalation formulations to improve resistance to moisture,".

Derwent#013790372, WPI Acc No.: 2001–274583/200129, for PCT Patent Application, WO 01/22956 "Drug combination of soft steroid and beta–2–adrenoceptor agonist, administered by inhalation for effective treatment of respiratory or allergic diseases, e.g. asthma,".

Derwent#014808338, WPI Acc No.: 2002–629044/200268, for PCT Patent Application, WO 02/060533 "Medicament containing a betamimetic and an oxitropium salt useful for the treatment of respiratory disorders with reduced side effects,".

Derwent#014816787, WPI. Acc No.: 2002–637493/200269, for PCT Patent Application, WO 02/060532 "Medicament containing a betamimetic and an ipratropium salt useful for the treatment of respiratory disorders with reduced side effects,".

Eickelberg et al., "Ligand–independent Activation of the Glucocorticoid Receptor by $6_2$ –Adrnergic Receptor Agonists in Primary Human Lung Fibroblasts and vascular Smooth Muscle Cells," *The Journal of Biological Chemistry* 274(2):1005–1010 (1999).

Farmer et al., "6–Adrenergic agonists exert their "anti–inflammatory" effects in monocytic cells through the IκB/NF–κB pathway," *Am. J. Physiol. Lung. Cell. Physiol.* 279:1675–682 (2000).

Greening et al., "Added salmeterol versus higher–dose corticosteroid in asthma patients with symptoms on existing inhaled corticosteroid," *The Lancet* 344:219–224 (1994).

Grootendorst et al., "Effects of oral prednisolone on the bronchoprotective effect of formoterol in patients with persistent asthma," *Eur. Respir. J.* 17:374–379 (2001).

Ida, Hisashi, "Pharmacology of Formoterol, (αRS)–3–formamido–4–hydroxy–α–[[[(αRS)–p–methoxy–α–methylphenethyl] amino] methyl] benzylalcohol fumarate dihydrate (BD 40A)," *Oyo Yakuri* 21(2):201–210 (1981).

Ito et al., "Glucorcorticoid Receptor Recruitment of Histone Deacetylase 2 Inhibits Interleukin–16–Induced Histone H4 Acetylation on Lysines 8 and 12," *Molecular and Cellular Biology* 20(18):6892–6903 (2000).

Ito et al., "p65–activated Histone Acetyltransferase Activity Is Repressed by Glucocorticoids," *The Journal of Biological Chemistry* 276(32):30208–30215 (2001).

Korn et al., "Effects of formoterol and budesonide on Bronchoprotection against Methacholine," *Am. J. Med.* 104:431–438 (1998).

Malolepszy et al., "Safety of formoterol Turbuhaler™ at cumulative dose of 90/µg in patients with acute bronchial obstruction," *Eur. Respir. J.* 18:928–934 (2001).

O'Connor, B.J., "Combinatorial Therapy," *Pulmonary Pharmacology & Therapeutics* 11: 397–399 (1998).

Oddera et al., "Salmeterol Enhances the Inhibitory Activity of Dexamethasone on Allergen–Induced Blood Mononuclear Cell Activation," *Respiration* 65:199–204 (1998).

Package Insert for: ADVAIR™ DISKUS http://fb.a–files.net/PackageInsert/Advair.htm (acessed on Sep. 26, 2002) (Copyright, 1999 Glaxo Wellcome Inc.).

Palmqvist et al., "Onset of Bronchodilation of Budesnide/Formoterol vs. Salmeterol/Fluticasone in Single Inhalers," *Pulmonary Pharmacology & Therapeutics* 14: 29–34 (2001).

Pang, L. and A.J. Knox, "Regulation of TNF–α–induced eotaxin release from cultured human airway smooth muscle cells by $6_2$–agonists and corticosteroids," *FASEB J*, 15: 261–269 (2001).

Pang, L. and A.J. Knox, "Synergistic Inhibition by $6_2$–Agonists and Corticosteroids on Tumor Necrosis Factor–α–Induced Interleukin–8 Release from Cultured Human Airway Smooth–Muscle Cells," *Am. J. Respir. Cell Mol. Biol.* 23:79–85 (2000).

Pauwels et al., "Effect of Inhaled Formoterol and Budesonide on Exacerbations of Asthma," *The New England Journal of Medicine* 337(20):1405–1411 (1997).

Schreurs et al., "A dose–response study with formoterol Turbuhaler™ as maintenance therapy in asthmatic patients," *Eur. Respir. J.* 9:1679–1683 (1996).

Seldon et al., "Albuterol Does Not Antagonize the Inhibitory Effect of Dexamethasone on Monocyte Cytokine Release," *Am. J. Respir. Crit. Care Med.* 157:803–809 (1998).

Silvestri et al., "Fluticasone and salmeterol downregulate in vitro, fibroblast proliferation and ICAM–1 or H–CAM expression," *Eur. Respir. J.* 18:139–145 (2001).

Sköld et al., "Glucocorticoids Augment Fibroblast–Mediated Contraction of Collagen Gels by Inhibition of Endogenous PGE Production," *Proceedings of the Association of American Physicians* 111(3):249–258 (1999).

Stewart et al., "Acute formoterol administration has no argogenic effect in nonasthmatic athletes," *Medicine & Science In Sports & Exercise* 34(2):213–217 (2002).

Vianna, E.O. and R.J. Martin, "Bronchodilators and Corticosteroids in the Treatment of Asthma," *Drugs of Today* 34(3):203–223 (1998).

Wilding et al., "Efect of long term treatment with salmeterol on asthma control: a double blind, randomised crossover study," *British Medical Journal* 314:1441–1446 (1997).

Woolcock et al., "Comparison of Addition of Salmeterol to Inhaled Steroids with Doubling of the Dose of Inhaled Steroids," *Am.J. Respir. Crit. Care Med.* 153:148101488 (1996).

"Flovent", Glaxo Wellcome Inc., *Physicians' Desk Reference*, 54th ed., (2000), pp. 1186–1189.

Warne, P.J., "The discovery and clinical development of RPR 106541: an airway–selective steroid for the treatment of asthma", *Emerging Drugs*, 5(2):231–239 (2000).

Hardman et al. (Eds.), *Goodman Gilman's The Pharmacological Basis of Therapeutics*, 1996, p. 665.

Leckie et al., "Novel Therapy of COPD," *Expert Opin Investig Drugs* 9(1):3–23 (2000).

*Physicians' Desk Reference: PDR*, Oradell, N.J.: Medical Economics Co., pp. 535–537, 480–482, 2828–2829 (2000).

Smaldone et al., "Budesonide Inhalation Suspension in Chemically Compatable With Other Nebulizing Formulations," *Chest* 118(4)Suppl: 98S (2000).

* cited by examiner

US 6,667,344 B2

BRONCHODILATING COMPOSITIONS AND METHODS

RELATED APPLICATIONS

Benefit of priority under 35 U.S.C. §119(e) is claimed to U.S. provisional patent application serial No. 60/284,606; filed Apr. 17, 2001, to Pham et al. The disclosure of the above-referenced application is incorporated herein by reference in its entirety.

FIELD OF THE INVENTION

Compositions and methods are provided relating to treatment, prevention, or amelioration of one or more symptoms of broncho-constrictive disorders. In particular, the compositions and methods herein include formoterol, and/or derivatives thereof. The compositions are propellant-free, sterile unit dose or multidose inhalation solutions intended for administration via nebulization.

BACKGROUND OF THE INVENTION

Bronchoconstrictive disorders affect millions worldwide. Such disorders include asthma (including bronchial asthma, allergic asthma and intrinsic asthma, e.g., late asthma and airway hyper-responsiveness), chronic bronchitis and other chronic obstructive pulmonary diseases. Compounds having $\beta_2$-adrenoreceptor agonist activity have been developed to treat these conditions. Such compounds include, but are not limited to, Albuterol ($\alpha^1$-(((1,1-dimethylethyl)amino) methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-$\alpha$-(((1,1-dimethylethyl)amino)-methyl)-5-isoxazolemethanol); Isoproterenol (4-(1-hydroxy-2-((1-methyl-ethyl)amino)ethyl)-1,2-benzenediol); Trimetoquinol (1,2,3,4-tetrahydro-1-((3,4,5-trimethoxyphenyl)methyl)-6,7-isoquinolinediol); Clenbuterol (4-amino-3,5-dichloro-$\alpha$-(((1,1-diemthylethyl)amino)methyl)benzenemethanol); Fenoterol (5-(1-hydroxy-2-((2-(4-hydroxyphenyl)-1-methylethyl)-amino)ethyl)-1,3-benzenediol); Formoterol (2-hydroxy-5-((1RS)-1-hydroxy-2-(((1RS)-2-(p-methoxyphenyl)-1-methylethyl)amino)ethyl)formanilide); (R,R)-Formoterol; Desformoterol ((R,R) or (S,S)-3-amino-4-hydroxy-$\alpha$-(((2-(4-methoxyphenyl)-1-methylethyl) amino)methyl)benzenemethanol); Hexoprenaline (4,4'-(1,6-hexanediyl)-bis(imino(1-hydroxy-2,1-ethanediyl)))bis-1,2-benzenediol); Isoetharine (4-(1-hydroxy-2-((1-methylethyl) amino)-butyl)-1,2-benzenediol); Isoprenaline (4-(1-hydroxy-2-((1-methylethyl)-amino)ethyl)-1,2-benzenediol); Metaproterenol (5-(1-hydroxy-2-((1-methylethyl)amino) ethyl)-1,3-benzenediol); Picumeterol (4-amino-3,5-dichloro-$\alpha$-(((6-(2-(2-pyridinyl)ethoxy)hexyl)amino) methyl)benzenemethanol); Pirbuterol ($\alpha^6$-(((1,1-dimethylethyl)amino)methyl)-3-hydroxy-2,6-pyridinemethanol); Procaterol (((R*,S*)-(±)-8-hydroxy-5-(1-hydroxy-2-((1-methylethyl)amino)butyl)-2(1H)-quinolinone); Reproterol ((7-(3-((2-(3,5-dihydroxyphenyl)-2-hydroxyethyl)amino)propyl)-3,7-dihydro-1,3-dimethyl-1H-purine-2,6-dione); Rimiterol (4-(hydroxy-2-piperidinylmethyl)-1,2-benzenediol); Salbutamol ((±)-$\alpha^1$-(((1,1-dimethylethyl)amino)methyl)-4-hydroxy-1,3-benzenedimethanol); (R)-Salbutamol; Salmeterol ((±)-4-hydroxy-$\alpha^1$-(((6-(4-phenylbutoxy)hexyl)amino)methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-$\alpha$-(((1,1-dimethylethyl) amino)methyl)benzenemethanol); and TA-2005 (8-hydroxy-5-((1R)-1-hydroxy-2-(N-((1R)-2-(4-methoxyphenyl)-1-methylethyl)amino)ethyl)-carbostyril hydrochloride).

These compounds are typically formulated for inhalation therapy. Aqueous or liquid formulations are preferred over solid formulations. Powdered formulations are more difficult to administer, particularly to the young and elderly who are most often the patients in need of such therapy. Compounds, such as formoterol, which has many desirable properties, are not adequately stable in aqueous solutions to be formulated as liquids. Hence there is a need for formulations of compounds, such as formoterol, in a form that can be conveniently administered and that are stable for extended periods of time. Therefore, it is an object herein to provide liquid formulations of $\beta_2$-adrenoreceptor agonist compounds. It is also an object herein to provide more stable formulations of others of these compounds.

SUMMARY OF THE INVENTION

Compositions and methods for treatment, prevention, or amelioration of one or more symptoms of bronchoconstrictive disorders are provided. The compositions provided herein are stable solutions of a bronchodilating agent, or a derivative thereof, in a pharmacologically suitable fluid that contains water, that are stable during long term storage. The compositions are suitable for direct administration to a subject in need thereof. Pharmacologically suitable fluids include, but are not limited to, polar fluids, including protic fluids. In certain embodiments herein, the compositions are aqueous solutions.

The compositions provided herein possess an estimated shelf-life of greater than 1, 2 or 3 months usage time at 25° C. and greater than or equal to 1, 2 or 3 years storage time at 5° C. In certain of these embodiments, using Arrhenius kinetics, >80% or >85% or >90% or >95% estimated bronchodilating agent remains after such storage. These compositions are particularly useful for administration via nebulization. In certain embodiments herein, the subject is a mammal. In other embodiments, the subject is a human.

The compositions provided herein are formulated to remain stable over a relatively long period of time. For example, the compositions provided herein are stored between −15° C. and 25° C., or between 2° C. and 8° C., and remain stable for the desired time. In one embodiment, the compositions are stored at 5° C.

Among the bronchodilating agents for use herein are Albuterol ($\alpha^1$-(((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-$\alpha$-(((1,1-dimethylethyl)amino)methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl)methyl)-6,7-isoquinolinediol); Clenbuterol (4-amino-3,5-dichloro-$\alpha$-(((1,1-diemthylethyl)amino)methyl)benzenemethanol); Fenoterol (5-(1-hydroxy-2-((2-(4-hydroxyphenyl)-1-methylethyl)amino)ethyl)-1,3-benzenediol); Formoterol (2-hydroxy-5-((1RS)-1-hydroxy-2-(((1RS)-2-(p-methoxyphenyl)-1-methylethyl)amino)ethyl)formanilide); (R,R)-Formoterol; Desformoterol ((R,R) or (S,S)-3-amino-4-hydroxy-$\alpha$-(((2-(4-methoxyphenyl)-1-methylethyl) amino)methyl)benzenemethanol); Hexoprenaline (4,4'-(1,6- hexanediyl)-bis(imino(1-hydroxy-2,1-ethanediyl)))bis-1,2-benzenediol); Isoetharine (4-(1-hydroxy-2-((1-methylethyl)amino)butyl)-1,2-benzenediol); Isoprenaline (4-(1-hydroxy-2-((methylethyl)amino)ethyl)-1,2-benzenediol); Metaproterenol (5-(1-hydroxy-2-((1-methylethyl)amino)ethyl)-1,3-benzenediol); Picumeterol (4-amino-3,5-dichloro-α-(((6-(2-(2-pyridinyl)ethoxy)hexyl)amino)methyl)benzenemethanol); Pirbuterol ($α^6$-(((1,1-dimethylethyl)amino)methyl)-3-hydroxy-2,6-pyridinemethanol); Procaterol (((R*,S*)-(±)-8-hydroxy-5-(1-hydroxy-2-((1-methylethyl)amino)butyl)-2(1H)-quinolinone); Reproterol ((7-(3-((2-(3,5-dihydroxyphenyl)-2-hydroxyethyl)amino)propyl)-3,7-dihydro-1,3-dimethyl-1H-purine-2,6-dione); Rimiterol (4-(hydroxy-2-piperidinylmethyl)-1,2-benzenediol); Salbutamol ((±)-$α^1$-(((1,1-dimethylethyl)amino)methyl)-4-hydroxy-1,3-benzenedimethanol); (R)-Salbutamol; Salmeterol ((±)-4-hydroxy-$α^1$-(((6-(4-phenylbutoxy)hexyl)amino)methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl)amino)methyl)benzenemethanol); and TA-2005 (8-hydroxy-5-((1R)-1-hydroxy-2-(N-((1R)-2-(4-methoxyphenyl)-1-methylethyl)amino)ethyl)carbostyril hydrochloride).

Of particular interest herein is formoterol, having the formula:

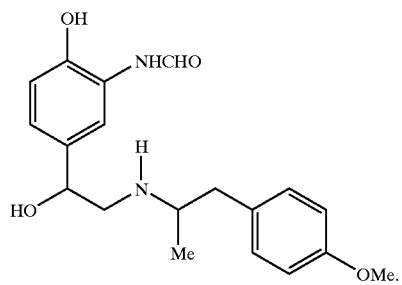

Formoterol for use in the compositions and methods provided herein includes 2-hydroxy-5-((1RS)-1-hydroxy-2-(((1RS)-2-(p-methoxyphenyl)-1-methylethyl)amino)ethyl)formanilide; or a stereoisomer thereof; and also includes the single enantiomers 2-hydroxy-5-((1S)-1-hydroxy-2-(((1S)-2-(p-methoxyphenyl)-1-methylethyl)amino)ethyl)formanilide and 2-hydroxy-5-((1R)-1-hydroxy-2-(((1R)-2-(p-methoxyphenyl)-1-methylethyl)amino)ethyl)formanilide.

In certain embodiments, the compositions are administered via nebulization. Administration of a nebulized aerosol is preferred over the use of dry powders for inhalation in certain subject populations, including pediatric and geriatric groups.

In one embodiment, the compositions for use in the methods provided herein contain a pharmaceutically acceptable derivative of formoterol. In another embodiment, the compositions for use in the methods provided herein contain a pharmaceutically acceptable salt of formoterol. Pharmaceutically acceptable salts include, but are not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. In one embodiment, the compositions for use in the methods provided herein contain formoterol fumarate or formoterol fumarate dihydrate. In another embodiment, the compositions for use in the methods provided herein contain formoterol tartrate.

Also provided herein are combinations containing a composition provided herein and a nebulizer. The combinations can be packaged as kits, which optionally contain other components, including instructions for use of the nebulizer. Any nebulizer is contemplated for use in the kits and methods provided herein. In particular, the nebulizers for use herein nebulize liquid formulations, including the compositions provided herein, containing no propellant. The nebulizer may produce the nebulized mist by any method known to those of skill in the art, including, but not limited to, compressed air, ultrasonic waves, or vibration. The nebulizer may further have an internal baffle. The internal baffle, together with the housing of the nebulizer, selectively removes large droplets from the mist by impaction and allows the droplets to return to the reservoir. The fine aerosol droplets thus produced are entrained into the lung by the inhaling air/oxygen.

Methods for the treatment, prevention, or amelioration of one or more symptoms of bronchoconstrictive disorders, including, but not limited to, asthma, including, but not limited to, bronchial asthma, allergic asthma and intrinsic asthma, e.g., late asthma and airway hyper-responsiveness; chronic bronchitis; and other chronic obstructive pulmonary diseases are provided. The methods involve administering an effective amount of a pharmaceutical composition provided herein to a subject in need of such treatment.

Articles of manufacture, containing packaging material, a composition provided herein, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction, are also provided.

DETAILED DESCRIPTION OF PREFERRED EMBODIMENTS

Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, formoterol refers to 2-hydroxy-5-((1RS)-1-hydroxy-2-(((1RS)-2-(p-methoxyphenyl)-1-methylethyl)amino)ethyl)formanilide; or a stereoisomer thereof. The term formoterol also refers to the single enantiomers 2-hydroxy-5-((1S)-1-hydroxy-2-(((1S)-2-(p-methoxyphenyl)-1-methylethyl)amino)ethyl)formanilide and 2hydroxy-5-((1R)-1hydroxy-2-(((1R)-2-(p-methoxyphenyl)-1-methylethyl)amino)ethyl)formanilide.

As used herein, formoterol fumarate refers to a salt of formoterol having the formula (formoterol)·½ fumarate.

As used herein, formoterol free base refers to the neutral, anhydrous form of formoterol. Thus, a recitation that a composition contains, e.g., 59 μg/mL of formoterol free base means that the composition contains 59 μ/mL of neutral, anhydrous formoterol. Such compositions may be prepared using a derivative of formoterol.

As used herein, an aerosol is liquid or particulate matter dispersed in air. Aerosols include dispersions of liquids, including aqueous and other solutions, and solids, including powders, in air.

As used herein, a nebulized solution refers to a solution that is dispersed in air to form an aerosol. Thus, a nebulized solution is a particular form of an aerosol.

As used herein, a nebulizer is an instrument that is capable of generating very fine liquid droplets for inhalation into the lung. Within this instrument, the nebulizing liquid or solution is atomized into a mist of droplets with a broad size distribution by methods known to those of skill in the art, including, but not limited to, compressed air, ultrasonic waves, or a vibrating orifice. Nebulizers may futher contain, eg., a baffle which, along with the housing of the instrument, selectively removes large droplets from the mist by impaction. Thus, the mist inhaled into the lung contains fine aerosol droplets.

As used herein, a pharmacologically suitable fluid is a solvent suitable for pharmaceutical use which is not a liquified propellant gas. Exemplary pharmacologically suitable fluids include polar fluids, including protic fluids such as water.

As used herein, a combination refers to any association between two or among more items.

As used herein, fluid refers to any composition that can flow. Fluids thus encompass compositions that are in the form of semi-solids, pastes, solutions, aqueous mixtures, gels, lotions, creams and other such compositions.

As used herein, a mixture is a mutual incorporation of two or more substances, without chemical union, the physical characteristics of each of the components being retained.

As used herein, the stability of a composition provided herein refers to the length of time at a given temperature that is greater than 80%, 85%, 90% or 95% of the initial amount of active ingredient, e.g., formoterol, is present in the composition. Thus, for example, a composition that is stable for 30 days at 25° C. would have greater than 80%, 85%, 90% or 95% of the initial amount of active ingredient present in the composition at 30 days following storage at 25° C.

As used herein, pharmaceutically acceptable derivatives of a compound include salts, esters, enol ethers, enol esters, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl) aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl and heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl and heterocyclyl. Pharmaceutically acceptable solvates and hydrates are complexes of a compound with one or more solvent or water molecule, preferably 1 to about 100, more preferably 1 to about 10, most preferably one to about 2, 3 or 4, solvent or water molecules. Formoterol salts and hydrates are used in certain embodiments herein.

As used herein, treatment means any manner in which one or more of the symptoms of a condition, disorder or disease are ameliorated or otherwise beneficially altered. Treatment also encompasses any pharmaceutical use of the compositions herein, such as use for treating cancer.

As used herein, amelioration of the symptoms of a particular disorder by administration of a particular pharmaceutical composition refers to any lessening, whether permanent or temporary, lasting or transient that can be attributed to or associated with administration of the composition.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392).

It is to be understood that the compounds for use in the compositions and methods provided herein may contain chiral centers. Such chiral centers may be of either the (R) or (S) configuration, or may be a mixture thereof. Thus, the compounds for use in the compositions provided herein may be enantiomerically pure, or be stereoisomeric or diastereomeric mixtures. It is to be understood that the chiral centers of the compounds provided herein may undergo epimerization in vivo. Thus, one of skill in the art will recognize that administration of a compound in its (R) form is equivalent, for compounds that undergo epimerization in vivo, to administration of the compound in its (S) form.

As used herein, bronchoconstriction refers to a reduction in the caliber of a bronchus or bronchi.

As used herein, undesired and/or uncontrolled bronchoconstriction refers to bronchoconstriction that results in or from a pathological symptom or condition. Pathological conditions include, but are not limited to, asthma and chronic obstructive pulmonary disease (COPD). Pathological symptoms include, but are not limited to, asthma and COPD.

As used herein, the statement that a composition is stable during "long term storage" means that the composition is suitable for administration to a subject in need thereof when it has an estimated shelf-life of greater than 1, 2 or 3 months usage time at 25° C. and greater than or equal to 1, 2 or 3 years storage time at 5° C. In certain embodiments herein, using Arrhenius kinetics, >80% or >85% or >90% or >95% estimated bronchodilating agent remains after such storage.

A. Formoterol

Formoterol (2-hydroxy-5-((1RS)-1-hydroxy-2-(((1RS)-2-(p-methoxyphenyl)-1-methylethyl)amino)ethyl) formanilide) is derived from adrenaline and, as noted above, is used as a $\beta_2$-stimulator in inhalation therapy of respiratory diseases, particularly for the treatment of bronchial asthma. It has been reported that in patients with reversible obstructive respiratory diseases, formoterol has a bronchodilatory effect. This effect has a relatively rapid onset (approximately 1–3 minutes) and a relatively long duration (greater than 12 hours). Formoterol inhibits the release of leukotrienes and other messenger substances involved with inflammation, such as histamines. In addition, formoterol may bring about a hyperglycaemic activity.

To date, formoterol has been formulated as a dry powder and administered via devices such as the Turbuhaler® and the Aerolizer®. See, e.g., Seberova et al. (2000) *Respir. Med.* 94(6):607–611; Lotvall et al. (1999) *Can. Respir. J.* 6(5): 412–416; Campbell et al. (1999) *Respir. Med.* 93(4): 236–244; *Nightingale* et al. (1999) *Am. J. Respir. Crit. Care Med.* 159(6):1786–1790; Lecaillon et al. (1999) *Eur. J. Clin. Pharmacol.* 55(2):131–138; Bartow et al. (1998) *Drugs* 55(2):303–322; Ekstrom et al. (1998) *Respir. Med.* 92(8): 1040–1045; Ringdal et al. (1998) *Respir. Med.* 92(8): 1017–1021; Totterman et al. (1998) *Eur. Respir. J.* 12(3): 573–579; Palmqvist et al. (1997) *Eur. Respir. J.* 10(11): 2484–2489; Nielsen et al. (1997) *Eur. Respir. J.* 10(9): 2105–2109; Ullman et al. (1996) *Allergy* 51(10):745–748; Selroos et al. (1996) *Clin. Immunother.* 6:273–299; and Schreurs et al. (1996) *Eur. Respir. J.* 9(8):1678–1683.

Formoterol is also available as a tablet and a dry syrup in certain areas of the world (e.g., Atock®, marcketed by Yamanouchi Pharmaceutical Co. Ltd., Japan). Formoterol formulations are also available in other areas (e.g., Europe and U.S.) for propellant-based metered dose inhalers and dry powder inhalers (e.g., Turbuhaler®, Aerolizer® and Foradil Aerolizer®). None of these formulations are water based. Sterile, stable, aqueous based inhalation solutions of formoterol for nebulization are not available, nor have they been reported.

Compositions containing formoterol in combination with other active ingredients have been disclosed. See, e.g., U.S. Pat. Nos. 6,004,537, 5,972,919 and 5,674,860 (formoterol and budenoside), U.S. Pat. Nos. 5,668,110, 5,683,983, 5,677,280 and 5,654,276 (formoterol and IL-5 inhibitors), U.S. Pat. No. 6,136,603 (formoterol and antisense modulators of IL-5), U.S. Pat. No. 5,602,110 (formoterol and millrinone), U.S. Pat. No. 5,525,623 (formoterol and a tryptase inhibitor), U.S. Pat. Nos. 5,691,336, 5,877,191, 5,929,094, 5,750,549 and 5,780,467 (formoterol and a tachykinin receptor antagonist); and International Patent Application Publication Nos. WO 99/00134 (formoterol and rofleponide) and WO 99/36095 (formoterol and a dopamine $D_2$ receptor agonist).

Other compositions containing formoterol have been disclosed in U.S. Pat. Nos. 5,677,809, 6,126,919, 5,733,526, 6,071,971, 6,068,833, 5,795,564, 6,040,344, 6,041,777, 5,874,481, 5,965,622 and 6,161,536.

U.S. Pat. No. 6,150,418 discloses a "liquid active substance concentrate" containing formoterol in the form of its free base or in the form of one of the pharmacologically acceptable salts or addition products (adducts) thereof as active substance. This "liquid active substance concentrate" is reported to be a concentrated (i.e., greater than 10 mg/mL, preferably 75 to 500 mg/mL) solution or suspension that is stable for a period of several months possibly up to several years without any deterioration in the pharmaceutical quality. This patent teaches that it is the high concentration that allows for the stability of the concentrate. The "liquid active substance concentrate" is not suitable for direct administration to a patient.

U.S. Pat. No. 6,040,344 discloses an aqueous aerosol formulation of formoterol tartrate for use in a nebulizer. This patent states that the formulation disclosed therein is not attractive for long term storage.

B. Compositions for Use in Treatment, Prevention, or Amelioration of One or More Symptoms of Bronchoconstrictive Disorders Pharmaceutical compositions containing a $\beta_2$-adrenoreceptor agonist for administration via nebulization are provided. The compositions are sterile filtered and filled in vials, including unit dose vials providing sterile unit dose formulations which are used in a nebulizer and suitably nebulized. Each unit dose vial is sterile and is suitably nebulized without contaminating other vials or the next dose.

The unit dose vials are formed in a form-fill-seal machine or by any other suitable method known to those of skill in the art. The vials may be made of plastic materials that are suitably used in these processes. For example, plastic materials for preparing the unit dose vials include, but are not limited to, low density polyethylene, high density polyethylene, polypropylene and polyesters. In one embodiment, the plastic material is low density polyethylene.

In one embodiment, the $\beta_2$-adrenoreceptor agonist is formoterol, or a pharmaceutically acceptable derivative thereof. In other embodiments, the formoterol for use in the compositions provided herein is formoterol fumarate. Formoterol refers to 2-hydroxy-5-((1RS)-1-hydroxy-2-(((1RS)-2-(p-methoxyphenyl)-1-methylethyl)amino)ethyl) formanilide; or a stereoisomer thereof. The term formoterol also refers herein to the single enantiomers 2-hydroxy-5-((1S)-1-hydroxy-2-(((1S)-2-(p-methoxyphenyl)-1-methylethyl)amino)ethyl)formanilide and 2-hydroxy-5-((1R)-1-hydroxy-2-(((1R)-2-(p-methoxyphenyl)-1-methylethyl)-amino)ethyl)formanilide.

In one embodiment, the compositions contain formoterol free base at a concentration of about 5 µg/mL to about 2 mg/mL. In other embodiments, the maximum concentration of formoterol free base in the compositions is 1.5 mg/mL. In further embodiments, the concentration of formoterol free base in the compositions is about 10 µ/mL to about 1 mg/mL, or about 50 µg/mL to about 200 µ/mL. In other embodiments, the compositions contain formoterol fumarate at a concentration of about 80 µg/mL up to about 175 to 200 µg/mL. In further embodiments, the compositions contain formoterol fumarate at a concentration of about 90 µg/mL up to about 125 to 150 µg/mL. The formoterol fumarate is formulated, in certain compositions provided herein, at a concentration of about 100 µg/mL. The formoterol fumarate is formulated, in other compositions provided herein, at a concentration of about 85 µg/mL or about 170 µg/mL. In one embodiment, the formoterol fumarate is formulated for single dosage administration via nebulization at a concentration of about 100 µg/mL. In another embodiment, the compositions contain formoterol free base at a concentration of about 40 to about 150 µg/mL, particularly about 59 or about 118 µg/mL.

The compostions containing the $\beta_2$-adrenoreceptor agonist, including formoterol, are formulated with a pharmacologically suitable fluid. Pharmacologically suitable fluids include, but are not limited to, polar solvents, including, but not limited to, compounds that contain hydroxyl groups or other polar groups. Such solvents include, but are not limited to, water or alcohols, such as ethanol, isopropanol, and glycols including propylene glycol, polyethylene glycol, polypropylene glycol, glycol ether, glycerol and polyoxyethylene alcohols.

Polar solvents also include protic solvents, including, but not limited to, water, aqueous saline solutions with one or more pharmaceutically acceptable salt(s), alcohols, glycols or a mixture thereof. For a saline solution as the solvent or as a component othereof, particularly suitable salts are those which display no or only negligible pharmacological activity after administration.

In the embodiments herein, the compositions have a pH of about 2.0 to about 8.0. In other embodiments, the compositions have a pH of about 4.0 to about 6.0, or about 4.5 to about 5.5. In certain of the above embodiments, the compositions are formulated at a pH of about 4, 4.4 or 4.6 up to about 5.5, 5.7 or 6. In other embodiments, the pH is about 5.0. It has been found herein that the rate constant for decomposition of an aqueous solution of formoterol is dependent on pH. The rate constant ($k_{obs}$) at 60° C. at a pH of 3, 4, 5 and 7 is approximately 0.62, 0.11, 0.044 and 0.55 day$^{-1}$, respectively. Therefore, the decomposition of formoterol in aqueous solution at 60° C. at a buffer concentration of 5 mM and an ionic strength of 0.05 is slowest at a pH of about 5.0.

The solubility of formoterol in aqueous solution has been found herein to be dependent on pH. Thus, at a pH of between about 5 and about 7, the aqueous solubility of formoterol at ambient temperature is approximately 2.2 mg/mL. At a pH of about 4, the aqueous solubility of formoterol at ambient temperature is approximately 3 mg/mL, while at a pH of about 3, the aqueous solubility of formoterol at ambient temperature is about 4.8 mg/mL. The solubility of formoterol in pure water, for example, high performance liquid chromatography (HPLC) water, at ambient temperature is approximately 2 mg/mL.

In other of the above embodiments, the compositions further contain a buffer, including, but not limited to, citric acid/phosphate, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)iminotris(hydroxymethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxymethyl)methylamino)propane), BES (N,N-bis(2-hydroxyethyl)-2-aminoethanesulfonaic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis (2-hydroxyethyl)amino)-2-hydroxypropanesulfonic acid), MOBS (4-(N-morpholino)butanesulfonic acid), TAPSO (3-(N-tris(hydroxymethyl)methylamino)-2-hydroxypropanesulfonic acid), TRIZMA® (tris (hydroxymethylaminomethane), HEPPSO (N-(2-hydroxyethyl)piperazine-N'-(2-hydroxypropanesulfonic acid), POPSO (piperazine-N,N'-bis(2-hydroxypropanesulfonic acid)), TEA (triethanolamine), EPPS (N-(2-hydroxyethyl)piperazine-N'-(3-propanesulfonic acid), TRICINE (N-tris(hydroxymethyl)methylglycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS (N-tris (hydroxymethyl)methyl-3-aminopropanesulfonic acid), AMPD (2-amino-2-methyl-1,3-propanediol), and/or any other buffers known to those of skill in the art. In one embodiment, the buffer is citric acid/phosphate buffer, acetate buffer, citrate buffer or phosphate buffer. In another embodiment, the buffer is a citrate buffer (citric acid/sodium citrate). The buffer concentration has been found herein to affect the stability of the composition. Buffer concentrations for use herein include from about 0 or 0.01 mM to about 150 mM, or about 1 mM to about 20 mM. In one embodiment, the buffer concentration is about 5 mM. In another embodiment, the buffer concentration is about 1 mM to about 50 mM, or about 20 mM. The kinetic-pH profile of formoterol is dependent on buffer concentration. At low and approximately neutral conditions, increasing the buffer concentration from 5 mM to 20 mM increased the rate constant of decomposition significantly. However, no noticeable differences in rate constant were observed in the pH region of about 4.5 to about 5.5 with increasing buffer concentration from 5 mM to 20 mM. The particular buffer and buffer concentration of a given composition for long term storage provided herein may be determined empirically using standard stability assays well known to those of skill in the art (see, e.g., the Examples).

The ionic strength of the compositions provided herein also has been found herein to affect the stability of the composition. Ionic strengths of the compositions provided herein are from about 0 to about 0.4, or from about 0.05 to about 0.16. Compositions having a lower ionic strength exhibit improved stability over formulations having higher ionic strength. The rate constant of decomposition was essentially the same at ionic strength 0.05 to 0.1, but increased to some extent at ionic strength of 0.2. The particular ionic strength of a given composition for long term storage provided herein may be determined empirically using standard stability assays well known to those of skill in the art (see, e.g., the Examples).

In embodiments where the pharamacologically suitable fluid is a saline solution, tonicity adjusting agents may be added to provide the desired ionic strength. Tonicity adjusting agents for use herein include those which display no or only negligible pharmacological activity after administration. Both inorganic and organic tonicity adjusting agents may be used in the compositions provided herein. Tonicity adjusting agents include, but are not limited to, ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, propylene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine and zinc sulfate. In certain embodiments, the tonicity adjusting agent is sodium chloride, which is present at a concentration of from about 0 mg/mL to about 10, 15 or 20 mg/mL. In further embodiments, the compositions contain sodium chloride at a concentration of from about 0 mg/mL to about 7.5 mg/mL. In another embodiment, the compositions contain sodium chloride at a concentration of 0 mg/mL, 1.5 mg/mL, 6.8 mg/mL or 7.5 mg/mL. In these embodiments, the pharmacologically suitable fluid is aqueous saline.

The storage temperature of the compositions provided herein also has been found herein to affect the stability of the composition. Compositions stored at a lower temperature exhibit improved stability over formulations stored at higher temperatures. The effect of temperature on the rate constant of decomposition at pH5, a buffer concentration of 5 mM, and an ionic strength of 0.05, was linear according to Arrhenius kinetics, i.e., when Ln $k_{obs}$ was plotted against 1/T, where T is the temperature in degree Kelvin.

The estimated shelf-life of formoterol in the compositions provided herein is significantly greater than that reported for known formoterol compositions. The estimated shelf-life of formoterol in the compositions provided herein is about 6.2 years at 5° C. and about 7.5 months at 25° C. The estimated formoterol concentrations in the compositions provided herein as a function of storage time at 5° C. and usage time at 25° C. was determined. It is estimated that greater than 90% of the initial formoterol present in the composition remains after 3 months of usage time at 25° C. and 3 years of storage time at 5° C. as well as after 0.5 months of usage time at 25° C. and 1 year of storage time at 5° C.

In one embodiment, the compositions provided herein are prepared containing formoterol fumarate at a nominal concentration of 0.1 mg/mL at the indicated pH and citric acid/phosphate buffer concentrations. The solutions were stored at 60° C. In these compositions, formoterol is relatively more stable at a pH from about 4 to about 5, and is also more stable at lower buffer concentration.

The compositions provided herein also may include excipients and additives. The particular excipient or additive for use in the compositions for long term storage provided herein may be determined empirically using methods well known to those of skill in the art (see, e.g., the Examples). Excipients and additives are any pharmacologically suitable and therapeutically useful substance which is not an active substance. Excipients and additives generally have no pharmacological activity, or at least no undesirable pharmacological activity. The excipients and additives include, but are not limited to, surfactants, stabilizers, complexing agents, antioxidants, or presevatives which prolong the duration of use of the finished pharmaceutical formulation, flavorings, vitamins, or other additives known in the art. Complexing agents include, but are not limited to, ethylenediaminetetraacetic acid (EDTA) or a salt thereof, such as the disodium salt, citric acid, nitrilotriacetic acid and the salts thereof. In one embodiment, the complexing agent is EDTA. Preservatives include, but are not limited to, those that protect the solution from contamination with pathogenic particles, including benzalkonium chloride or benzoic acid, or benzoates such as sodium benzoate. Antioxidants include, but are not limited to, vitamins, provitamins, ascorbic acid, vitamin E or salts or esters thereof.

The compositions provided herein also may include a cosolvent, which increases the solubility of additives or the active ingredient(s). The particular cosolvent for use in the compositions for long term storage provided herein may be determined empirically using methods well known to those of skill in the art (see, e.g., the Examples). Cosolvents for use herein include, but are not limited to, hydroxylated solvents or other polar solvents, such as alcohols such as isopropyl alcohol, glycols such as propylene glycol, polyethylene glycol, polypropylene glycol, glycol ether, glycerol, and polyoxyethylene alcohols.

C. Preparation of Compounds for Use in the Compositions

The preparation of the compounds used in the compositions provided herein is described below. Any such compound or similar compound may be synthesized according to a method discussed in general below or by only minor modification of the methods by selecting appropriate starting materials.

Formoterol may be prepared according to the method disclosed in U.S. Pat. No. 3,994,974. Briefly, 4-benzyloxy-3-nitro-α-bromoacetophenone is reacted with N-benzyl-N-(1-methyl-2-p-methoxyphenylethyl)amine to form the α-aminoacetophenone. This compound was subjected to the following series of reactions: (i) reduction of the ketone with sodium borohydride; (ii) reduction of the nitro group with aqueous hydrochloric acid and iron powder; (iii) amine formulation with acetic anhydride and formic acid; and (iv) catalytic reduction over 10% palladium on carbon to afford formoterol free base. Crystallization of the ½ fumarate salt from ethanol provides (formoterol)·½ fumarate.

The individual enantiomers of formoterol, 2-hydroxy-5-((1S)-1-hydroxy-2-(((1S)-2-(p-methoxyphenyl)-1-methylethyl)amino)ethyl)-formanilide and 2-hydroxy-5-((1R)-1-hydroxy-2-(((1R)-2-(p-methoxyphenyl)-1-methylethyl)amino)ethyl)formanilide, may be prepared by the method disclosed in U.S. Pat. No. 6,040,344. Briefly, reaction of optically pure 4-benzyloxy-3-formamidostyrene oxide with an optically pure 4-methoxy-α-methyl-N-(phenylmethyl)benzeneethanamine, followed by debenzylation, affords the desired enantiomer of formoterol. Debenzylation may be accomplished by reduction with hydrogen gas in the presence of a noble metal catalyst, such as palladium on carbon.

The required optically pure 4-benzyloxy-3-formamidostyrene oxide may be prepared from 4-benzyloxy-3-nitro-α-bromoacetophenone by (i) reduction with vorane in the presence of an optically pure aminoindanol, (ii) hydrogenation over platinum oxide catalyst, (iii) formulation with formic acid and acetic anhydride, and (iv) epoxide formation in the presence of potassium carbonate.

The required optically pure 4-methoxy-α-methyl-N-(phenylmethyl)-benzeneethanamine may be prepared from 4-methoxyphenylacetone by (i) reductive amination with benzylamine in the presence of hydrogen and a platinum catalyst, and (ii) crystallization of the desired optically pure amine from the resulting racemic mixture as its mandelic acid salt.

D. Formulation of Pharmaceutical Compositions

The compositions provided herien are prepared by procedures well known to those of skill in the art. For example, a formoterol fumarate solution may be prepared by the procedure of EXAMPLE 1. Briefly, a buffer solution having a pH and ionic strength of interest herein is prepared. In one embodiment, the buffer is a mixture of citric acid and sodium citrate, with sodium chloride added to achieve the desired ionic strength. Formoterol fumarate dihydrate is added to the buffer solution with agitation to produce a solution of the desired formoterol concentration. Exemplary formoterol concentrations are 0.17 g formoterol fumarate dihydrate/2 L and 0.34 g formoterol fumarate dihydrate/2 L buffer.

E. Evaluation of the Activity of the Compositions

Standard physiological, pharmacological and biochemical procedures are available for testing the compositions provided herein to identify those that possess bronchodilatory activity.

In vitro and in vivo assays that may be used to evaluate bronchodilatory activity are well known to those of skill in the art. See also, e.g., U.S. Pat. Nos. 3,994,974, and 6,068, 833; German Patent No. 2,305,092; Kaumann et al. (1985) *Naunyn-Schmied Arch. Pharmacol.* 331:27–39; Lemoine et al. (1985) *Naunyn-Schmied Arch. Pharmacol.* 331:40–51; Tomioka et al (1981) *Arch. Int. Pharmacodyn.* 250:279–292; Dellamary et al. (2000) *Pharm. Res.* 17(2):168–174; Rico-Mendez et al. (1999) *Rev. Alerg. Mex.* 46(5):130–135; Seberova et al. (2000) *Respir. Med.* 94(6):607–611; Lotvall et al. (1999) *Can. Respir. J.* 6(5):412–416; Campbell et al. (1999) *Respir. Med.* 93(4):236–244; Nightingale et al. (1999) *Am. J. Respir. Crit. Care Med.* 159(6):1786–1790; Lecaillon et al. (1999) *Eur. J. Clin. Pharmacol.* 55(2): 131–138; Bartow et al. (1998) *Drugs* 55(2):303–322; Ekstrom et al. (1998) *Respir. Med.* 92(8):1040–1045; Ringdal et al. (1998) *Respir. Med.* 92(8):1017–1021; Totterman et al. (1998) *Eur. Respir. J.* 12(3):573–579; Palmqvist et al. (1997) *Eur. Respir. J.* 10(11):2484–2489; Nielsen et al. (1997) *Eur. Respir. J.* 10(9):2105–2109; Ullman et al. (1996) *Allergy* 51(10):745–748; Selroos et al. (1996) *Clin. Immunother.* 6:273–299; and Schreurs et al. (1996) *Eur. Respir. J.* 9(8):1678–1683.

F. Methods of Treatment of Bronchoconstrictive Disorders

The compositions provided herein are used for treating, preventing, or ameliorating one or more symptoms of a bronchoconstrictive disorders in a subject. In one embodiment, the method includes administering to a subject an effective amount of a composition containing a bronchodilating agent, including, but not limited to, formoterol, whereby the disease or disorder is treated or prevented. The subject treated is, in certain embodiments, a mammal. The mammal treated is, in certain embodiments, a human.

In another embodiment, the method provided herein includes oral administration of a composition provided herein. In certain embodiments herein, the composition is directly administered to a subject in need of such treatment via nebulization without dilution or other modification of the composition prior to administration.

The methods for treatment, prevention, or amelioration of one or more symptoms of bronchoconstrictive disorders, in another embodiment, further include administering one or more of (a), (b), (c) or (d) as follows: (a) a $\beta_2$-adrenoreceptor agonist; (b) a dopamine ($D_2$) receptor agonist; (c) a prophylactic therapeutic, such as a steroid; or (d) an anticholinergic agent; simultaneously with, prior to or subsequent to the composition provided herein.

$\beta_2$-Adrenoreceptor agonists for use in combination with the compositions provided herein include, but are not limited to, Albuterol ($\alpha^1$-(((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-α-(((1,1-dimethylethyl)amino)methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl)methyl)-6,7-isoquinolinediol); Clenbuterol (4-amino-3,5-dichloro-α-(((1,1-diemthylethyl)amino)methyl)benzenemethanol); Fenoterol (5-(1-hydroxy-2-((2-(4-hydroxyphenyl)-1-methylethyl)amino)ethyl)-1,3-benzenediol); Formoterol (2-hydroxy-5-((1RS)-1-hydroxy-2-(((1RS)-2-(p-methoxyphenyl)-1-methylethyl)amino)ethyl)formanilide); (R,R)-Formoterol; Desformoterol ((R,R) or (S,S)-3-amino-4-hydroxy-α-(((2-(4-methoxyphenyl)-1-methylethyl)amino)methyl)benzenemethanol); Hexoprenaline (4,4'-(1,6-hexanediiyl)-bis(imino(1-hydroxy-2,1-ethanediyl)))bis-1, 2benzenediol); Isoetharine (4-(1-hydroxy-2-((1-methylethyl)amino)butyl)-1,2-benzenediol); Isoprenaline (4-(1-hydroxy-2-((1-methylethyl)amino)ethyl)-1,2-benzenediol); Metaproterenol (5-(1-hydroxy-2-((1-methylethyl)amino)ethyl)-1,3-benzenediol); Picumeterol (4-amino-3,5-dichloro-α-(((6-(2-(2-pyridinyl)ethoxy)hexyl)amino)methyl)benzenemethanol); Pirbuterol ($\alpha^6$-(((1,1-dimethylethyl)amino)methyl)-3-hydroxy-2,6-pyridinemethanol); Procaterol (((R*,S*)-(±)-8-hydroxy-5-(1-hydroxy-2-((1-methylethyl)amino)butyl)-2(1H)-quinolinone); Reproterol ((7-(3-((2-(3,5-dihydroxyphenyl)-2-hydroxyethyl)amino)propyl)-3,7-dihydro-1,3-dimethyl-1H-purine-2,6-dione); Rimiterol (4-(hydroxy-2-piperidinylmethyl)-1,2-benzenediol); Salbutamol ((±)-$\alpha^1$-(((1,1-dimethylethyl)amino)methyl)-4-hydroxy-1,3-benzenedimethanol); (R)-Salbutamol; Salmeterol ((±)-4-hydroxy-$\alpha^1$-(((6-(4-phenylbutoxy)hexyl)amino)methyl)-1, 3-benzenedimethananol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl)amino)methyl)benzenemethanol); and TA-2005 (8-hydroxy-5-((1R)-1-hydroxy-2-(N-((1R)-2-(4-methoxyphenyl)-1-methylethyl)amino)ethyl)amino)ethyl)carbostyril hydrochloride).

Dopamine ($D_2$) receptor agonists include, but are not limited to, Apomorphine ((r)-5,6,6a,7-tetrahydro-6-methyl-4H-dibenzo[de,g]quinoline-10,11-diol); Bromocriptine ((5'α)-2-bromo-12'-hydroxy-2'-(1-methylethyl)-5'-(2-methylpropyl)ergotaman-3',6',18-trione); Cabergoline ((8β)-N-(3(dimethylamino)propyl)-N-((ethylamino) carbonyl)6-(2-propenyl)ergoline-8-carboxamide); Lisuride (N'-((8α)-9,10-didehydro-6-methylergolin-8-yl)-N,N-diethylurea); Pergolide ((8β)-8-((methylthio)methyl)-6-propylergoline); Levodopa (3-hydroxy-L-tryrosine); Pramipexole ((s)-4,5,6,7-tetrahydro-$N^6$-propyl-2,6-benzothiazolediamine); Quinpirole hydrochirodie (trans-(−)-4aR-4,4a,5,6,7,8,8a,9-octahydro-5-propyl-1H-pyrazolo[3,4-g]quinoline hydrochloride); Ropinirole (4-(2-(dipropylamino)ethyl)-1,3-dihydro-2H-indol-2-one); and Talipexole (5,6,7,8-tetrahydro-6-(2-propenyl)-4H-thiazolo[4,5-d]azepin-2-amine). Other dopamine $D_2$ receptor agonists for use herein are disclosed in International Patent Application Publication No. WO 99/36095.

Prophylactic therapeutics for use in combination therapy herein include steroidal anti-inflammatory agents, including, but not limited to, beclomethasone dipropionate (BDP), beclomethasone monopropionate (BMP), flunisolide, triamcinolone acetonide, dexamethasone, tipredane, ciclesonid, rofleponide, mometasone, mometasone furoate (Asmanex® Twisthaler™, Shering-Plough Corporation, Kenilworth, N.J.), RPR 106541, having the formula

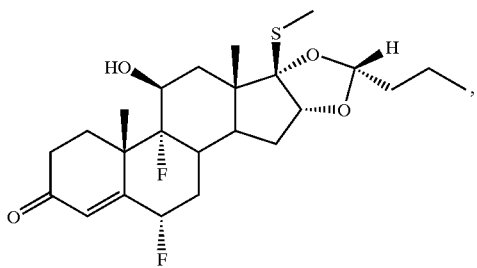

fluticasone or fluticasone propionate and budesonide or by way of sodium cromoglycate or nedocromil sodium.

Anticholinergic agents for use herein include, but are not limited to, ipratropium bromide, oxitropium bromide, atropine methyl nitrate, atropine sulfate, ipratropium, belladonna extract, scopolamine, scopolamine methobromide, homatropine methobromide, hyoscyamine, isopriopramide, orphenadrine, benzalkonium chloride, tiotropium bromide and glycopyrronium bromide. In certain embodiments, the compositions contain an anticholinergic agent, such as ipratropium bromide or tiotropium bromide, at a concentration of about 5 µg/mL to about 5 mg/mL, or about 50 µg/mL to about 200 µg/mL. In other embodiments, the compositions for use in the methods herein contain an anticholinergic agent, including ipratropium bromide and tiotropium bromide, at a concentration of about 83 µg/mL or about 167 µg/mL.

Other active ingredients for use herein in combination therapy, include, but are not limited to, IL-5 inhibitors such as those disclosed in U.S. Pat. Nos. 5,668,110, 5,683,983, 5,677,280 and 5,654,276; antisense modulators of IL-5 such as those disclosed in U.S. Pat. No. 6,136,603; milrinone (1,6-dihydro-2-methyl-6-oxo-[3,4'-bipyridine]-5-carbonitrile); milrinone lactate; tryptase inhibitors such as those disclosed in U.S. Pat. No. 5,525,623; tachykinin receptor antagonists such as those disclosed in U.S. Pat. Nos. 5,691,336, 5,877,191, 5,929,094, 5,750,549 and 5,780,467; leukotriene receptor antagonists such as montelukast sodium (Singular®, R-(E)]-1-[[[1-[3-[2-(7-chloro-2-quinolinyl)ethenyl]phenyl]-3-[2-(1-hydroxy-1-methylethyl) phenyl]propyl]thio]methyl]cyclopropaneacetic acid, monosodium salt), 5-lapoxygenase inhibitors such as zileuton (Zyflo®, Abbott Laboratories, Abbott Park, Ill.), and anti-IgE antibodies such as Xolair® (recombinant humanized anti-IgE monoclonal antibody (CGP 51901; IGE 025A; rhuMAb-E25), Genentech, Inc., South San Francisco, Calif.).

The bronchoconstrictive disorder to be treated, prevented, or whose one or more symptoms are to be ameliorated is associated with asthma, including, but not limited to, bronchial asthma, allergic asthma and intrinsic asthma, e.g., late asthma and airway hyper-responsiveness; and, particularly in embodiments where an anticholinergic agent is used, other chronic obstructive pulmonary diseases (COPDs), including, but not limited to, chronic bronchitis, emphysema, and associated cor pulmonale (heart disease secondary to disease of the lungs and respiratory system) with pulmonary hypertension, right ventricular hypertrophy and right heart failure. COPD is frequently associated with cigarette smoking, infections, environmental pollution and occupational dust exposure.

G. Nebulizers

The compositions provided herein are intended for administration to a subject in need of such treatment via nebulization. Nebulizers that nebulize liquid formulations containing no propellant are suitable for use with the compositions provided herein. Nebulizers are available from, e.g., Pari GmbH (Starnberg, Germany), DeVilbiss Healthcare (Heston, Middlesex, UK), Healthdyne, Vital Signs, Baxter, Allied Health Care, Invacare, Hudson, Omron, Bremed, AirSep, Luminscope, Medisana, Siemens, Aerogen, Mountain Medical, Aerosol Medical Ltd. (Colchester, Essex, UK), AFP Medical (Rugby, Warwickshire, UK), Bard Ltd. (Sunderland, UK), Carri-Med Ltd. (Dorking, UK), Plaem Nuiva (Brescia, Italy), Henleys Medical Supplies (London, UK), Intersurgical (Berkshire, UK), Lifecare Hospital Supplies (Leies, UK), Medic-Aid Ltd. (West Sussex, UK), Medix Ltd. (Essex, UK), Sinclair Medical Ltd. (Surrey, UK), and many others.

Nebulizers for use herein include, but are not limited to, jet nebulizers (optionally sold with compressors), ultrosonic nebulizers, and others. Exemplary jet nebulizers for use herein include Pari LC plus/ProNeb, Pari LC plus/ProNeb Turbo, Pari LC plus/Dura Neb 1000 & 2000, Pari LC plus/Walkhaler, Pari LC plus/Pari Master, Pari LC star, Omron CompAir XL Portable Nebulizer System (NE-C18 and JetAir Disposable nebulizer), Omron CompAir Elite Compressor Nebulizer System (NE-C21 and Elite Air Reusable Nebilizer), Pari LC Plus or Pari LC Star nebulizer with Proneb Ultra compressor, Pulmo-aide, Pulmo-aide LT, Pulmo-aide traveler, Invacare Passport, Inspiration Healthdyne 626, Pulmo-Neb Traverler, DeVilbiss 646, Whisper Jet, Acorn II, Misty-Neb, Allied aerosol, Schuco Home Care, Lexan Plasic Pocet Neb, SideStream Hand Held Neb, Mobil Mist, Up-Draft, Up-Draft II, T Up-Draft, ISO-NEB, AVA-NEB, Micro Mist, and PulmoMate. Exemplary ultrasonic nebulizers for use herein include MicroAir, UltraAir, Siemens Ultra Nebulizer 145, CompAir, Pulmosonic, Scout, 5003 Ultrasonic Neb, 5110 Ultrasonic Neb, 5004 Desk Ultrasonic Nebulizer, Mystique Ultrasonic, Luminscope's Ultrasonic Nebulizer, Medisana Ultrasonic Nebulizer, Microstat Ultrasonic Nebulizer, and MABISMist Hand Held Ultrasonic Nebulizer. Other nebulizers for use herein include 5000 Electromagnetic Neb, 5001 Electromagnetic Neb 5002 Rotary Piston Neb, Lumineb I Piston Nebulizer 5500, Aeroneb™ Portable Nebulizer System, Aerodose™ Inhaler, and AeroEclipse Breath Actuated Nebulizer.

H. Articles of Manufacture

The compositions provided herein may be packaged as articles of manufacture containing packaging material, a composition provided herein, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

In one embodiment herein, the compositions are packaged with a nebulizer for direct administration of the composition to a subject in need thereof.

The following examples are included for illustrative purposes only and are not intended to limit the scope of the invention.

EXAMPLE 1

Preparation of Formoterol Inhalation Solution Formulation

To a 5 L stainless steel vessel were added 0.68 g citric acid USP, 1.99 g sodium citrate USP, and 17.5 g sodium chloride USP. Purified water USP (2 L) was added to the stainless steel vessel and the contents were mixed with an overhead stirrer at a speed of 240 rpm for 10 minutes. Formoterol fumarate dihydrate (0.17 g for low dosage strength formulation, 0.34 g for high dosage strength formulation) was added and the solution was stirred at 240 rpm for 90 minutes.

EXAMPLE 2

Preparation of Formoterol Unit Dose Formulations

Following the procedure of EXAMPLE 1, the following formoterol unit dose formulations were prepared.

Low Strength (0.0085%)

A low strength formoterol unit dose formulation was prepared using the following reagents in the amounts indicated: formoterol fumarate dihydrate (0.170 mg), citric acid monohydrate, USP (0.68 mg), sodium citrate dihydrate, USP (1.99 mg), sodium chloride, USP (17.5 mg), and purified water, USP (qs to 2 mL).

High Strength (0.0170%)

A high strength formoterol unit dose formulation was prepared using the following reagents in the amounts indicated: formoterol fumarate dihydrate (0.340 mg), citric acid monohydrate, USP (0.68 mg), sodium citrate dihydrate, USP (1.99 mg), sodium chloride, USP (17.5 mg), and purified water, USP (qs to 2 mL).

EXAMPLE 3

Procedure for Stability Testing of Formoterol Solutions

Stability samples of the solutions prepared in EXAMPLES 1 and 2 were placed in scintillation vials with teflon-lined caps and stored in stability ovens at accelerated temperatures. At selected time points, aliquots of the samples were removed from the scintillation vials. The formoterol concentrations of the samples were analyzed by high performance liquid chromatography.

Since modifications will be apparent to those of skill in this art, it is intended that this invention be limited only by the scope of the appended claims.

What is claimed is:

1. A pharmaceutical composition, comprising formoterol, or a derivative thereof, in a pharmacologically suitable fluid, wherein the composition is stable during long term storage, the fluid comprises water, and the composition is formulated at a concentration suitable for direct administration to a subject in need thereof.

2. The pharmaceutical composition of claim 1, wherein the composition has an estimated shelf-life of greater than 1 month usage time at 25° C. and greater than or equal to 1 year storage time at 5° C.

3. The pharmaceutical composition of claim 2, wherein greater than about 80% of the initial formoterol is present after 1 month usage time at 25° C. and 1 year storage time at 5° C.

4. The pharmaceutical composition of claim 1 that has been nebulized.

5. The pharmaceutical composition of claim 1, wherein the pharmacologically suitable fluid comprises a polar solvent.

6. The pharmaceutical composition of claim 5, wherein the polar solvent is a protic solvent.

7. The pharmaceutical composition of claim 6, further comprising a tonicity adjusting agent.

8. The pharmaceutical composition of claim 7, wherein the tonicity adjusting agent is ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, propylene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine or zinc sulfate.

9. The pharmaceutical composition of claim 8, wherein the tonicity adjusting agent is sodium chloride.

10. The pharmaceutical composition of claim 1, wherein the pharmacologically suitable fluid comprises a buffer.

11. The pharmaceutical composition of claim 10, wherein the buffer is citric acid/phosphate, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)iminotris(hydroxymethyl) methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxymethyl) methylamino)propane), BES (N,N-bis(2-hydroxyethyl)-2-aminoethanesulfonaic acid), MOPS (3-(N-morpholino) propanesulfonic acid), TES (N-tris(hydroxymethyl)methyl-2-aminoethanesulfonic acid), HEPES (N-(2-hydroxyethyl) piperazine-N'-(2-ethanesulfonic acid), DIPSO (3-(N,N-bis (2-hydroxyethyl)amino)-2-hydroxy-propanesulfonic acid), MOBS (4-(N-morpholino)butanesulfonic acid), TAPSO (3-(N-tris(hydroxymethyl)methylamino)-2-hydroxy-propanesulfonic acid), tris(hydroxymethylaminomethane, HEPPSO (N-(2-hydroxyethyl)piperazine-N'-(2-hydroxypropanesulfonic acid), POPSO (piperazine-N,N'-bis (2-hydroxypropanesulfonic acid)), TEA (triethanolamine), EPPS (N-(2-hydroxyethyl)piperazine-N'-(3-propane-sulfonic acid), TRICINE (N-tris(hydroxymethyl) methylglycine), GLY-GLY (glycylglycine), BICINE (N,N-bis(2-hydroxyethyl)glycine), HEPBS (N-(2-hydroxyethyl) piperazine-N'-(4-butanesulfonic acid)), TAPS (N-tris (hydroxy-methyl)methyl-3-aminopropanesulfonic acid), or AMPD (2-amino-2-methyl-1,3-propanediol) buffer.

12. The pharmaceutical composition of claim 11, wherein the buffer is citrate buffer.

13. The pharmaceutical composition of claim 12, wherein the buffer concentration is from about 0.01 mM to about 150 mM.

14. The pharmaceutical composition of claim 13, wherein the buffer concentration is from about 1 mM to about 20 mM.

15. The pharmaceutical composition of claim 14, wherein the buffer concentration is about 5 mM.

16. The pharmaceutical composition of claim 8, wherein the ionic strength of the composition is about 0 to about 0.4.

17. The pharmaceutical composition of claim 16, wherein the ionic strength of the composition is about 0.05 to about 0.16.

18. The pharmaceutical composition of claim 1, wherein the pH of the composition is about 2.0 to about 8.0.

19. The pharmaceutical composition of claim 18, wherein the pH of the composition is about 4.0 to about 6.0.

20. The pharmaceutical composition of claim 19, wherein the pH of the composition is about 4.5 to about 5.5.

21. The pharmaceutical composition of claim 20, wherein the pH of the composition is about 5.0.

22. The pharmaceutical composition of claim 1, wherein the formoterol free base concentration is about 5 µg/mL to about 2 mg/mL.

23. The pharmaceutical composition of claim 22, wherein the formoterol free base concentration is about 10 µg/mL to about 1 mg/mL.

24. The pharmaceutical composition of claim 23, wherein the formoterol free base concentration is about 50 µg/mL to about 200 µg/mL.

25. The pharmaceutical composition of claim 24, wherein the formoterol free base concentration is about 59 µg/mL.

26. The pharmaceutical composition of claim 24, wherein the formoterol free base concentration is about 118 µg/mL.

27. The pharmaceutical composition of claim 8, further comprising a buffer.

28. The pharmaceutical composition of claim 27, wherein the buffer is citric acid/phosphate, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)iminotris(hydroxymethyl) methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxymethyl) methylamino)propane), BES (N,N-bis(2-hydroxyethyl)-2-aminoethanesulfonaic acid), MOPS (3-(N-morpholino) propanesulfonic acid), TES (N-tris(hydroxymethyl)methyl-2-aminoethanesulfonic acid), HEPES (N-(2-hydroxyethyl) piperazine-N'-(2-ethanesulfonic acid), DIPSO (3-(N,N-bis (2-hydroxyethyl)amino)-2-hydroxypropanesulfonic acid), MOBS (4-(N-morpholino)butanesulfonic acid), TAPSO (3-(N-tris(hydroxymethyl)methylamino)-2-hydroxy-propanesulfonic acid), tris(hydroxymethylaminomethane, HEPPSO (N-(2-hydroxyethyl)piperazine-N'-(2-hydroxypropanesulfonic acid), POPSO (piperazine-N,N'-bis (2-hydroxypropanesulfonic acid)), TEA (triethanolamine), EPPS (N-(2-hydroxyethyl)piperazine-N'-(3-propane-sulfonic acid), TRICINE (N-tris(hydroxymethyl) methylglycine), GLY-GLY (glycylglycine), BICINE (N,N-bis(2-hydroxyethyl)glycine), HEPBS (N-(2-hydroxyethyl) piperazine-N'-(4-butanesulfonic acid)), TAPS (N-tris (hydroxy-methyl)methyl-3-aminopropanesulfonic acid), or AMPD (2-amino-2-methyl-1,3-propanediol) buffer.

29. The pharmaceutical composition of claim 28, wherein the buffer is citrate buffer.

30. The pharmaceutical composition of claim 29, wherein the buffer concentration is from about 0.01 mM to about 150 mM.

31. The pharmaceutical composition of claim 30, wherein the buffer concentration is from about 1 mM to about 20 mM.

32. The pharmaceutical composition of claim 31, wherein the buffer concentration is about 5 mM.

33. The pharmaceutical composition of claim 27, wherein the ionic strength of the composition is about 0 to about 0.4.

34. The pharmaceutical composition of claim 33, wherein the ionic strength of the composition is about 0.05 to about 0.16.

35. The pharmaceutical composition of claim 27, wherein the pH of the composition is about 2.0 to about 8.0.

36. The pharmaceutical composition of claim 35, wherein the pH of the composition is about 4.0 to about 6.0.

37. The pharmaceutical composition of claim 36, wherein the pH of the composition is about 4.5 to about 5.5.

38. The pharmaceutical composition of claim 37, wherein the pH of the composition is about 5.0.

39. The pharmaceutical composition of claim 27, wherein the formoterol free base concentration is about 5 µg/mL to about 2 mg/mL.

40. The pharmaceutical composition of claim 39, wherein the formoterol free base concentration is about 10 µg/mL to about 1 mg/mL.

41. The pharmaceutical composition of claim 40, wherein the formoterol free base concentration is about 50 µg/mL to about 200 µg/mL.

42. The pharmaceutical composition of claim 41, wherein the formoterol free base concentration is about 59 µg/mL.

43. The pharmaceutical composition of claim 41, wherein the formoterol free base concentration is about 118 µg/mL.

44. The pharmaceutical composition of claim 25 that has been nebulized.

45. The pharmaceutical composition of claim 26 that has been nebulized.

46. The pharmaceutical composition of claim 42 that has been nebulized.

47. The pharmaceutical composition of claim 43 that has been nebulized.

48. The pharmaceutical composition of claim 27 that has been nebulized.

49. The pharmaceutical composition of claim 42, wherein the buffer is citrate buffer.

50. The pharmaceutical composition of claim 42, wherein the buffer concentration is about 5 mM.

51. The pharmaceutical composition of claim 42, wherein the ionic strength of the composition is about 0.05 to about 0.16.

52. The pharmaceutical composition of claim 42, wherein the pH of the composition is about 5.0.

53. The pharmaceutical composition of claim 42, wherein the buffer is citrate buffer; the buffer concentration is about 5 mM; the ionic strength of the composition is about 0.05 to about 0.16; and the pH of the composition is about 5.0.

54. The pharmaceutical composition of claim 43, wherein the buffer is citrate buffer.

55. The pharmaceutical composition of claim 43, wherein the buffer concentration is about 5 mM.

56. The pharmaceutical composition of claim 43, wherein the ionic strength of the composition is about 0.05 to about 0.16.

57. The pharmaceutical composition of claim 43, wherein the pH of the composition is about 5.0.

58. The pharmaceutical composition of claim 43, wherein the buffer is citrate buffer; the buffer concentration is about 5 mM; the ionic strength of the composition is about 0.05 to about 0.16; and the pH of the composition is about 5.0.

59. The pharmaceutical composition of claim 53 that has been nebulized.

60. The pharmaceutical composition of claim 58 that has been nebulized.

61. A nebulized solution, comprising formoterol or a derivative thereof in a pharmacologically suitable fluid.

62. A combination, comprising:
(a) the pharmaceutical composition of claim 1 formulated for single dosage administration; and
(b) a vial.

63. The combination of claim 62, wherein the aqueous composition comprises (a) formoterol free base at a concentration of about 59 µg/mL; (b) aqueous saline comprising sodium chloride; and (c) citrate buffer at a concentration of about 5 mM;
wherein the ionic strength of the composition is about 0.05 to about 0.1 6; and the pH of the composition is about 5.0.

64. The combination of claim 62, wherein the aqueous composition comprises (a) formoterol free base at a concentration of about 118 µg/mL; (b) aqueous saline comprising sodium chloride; and (c) citrate buffer at a concentration of about 5 mM;
wherein the ionic strength of the composition is about 0.05 to about 0.16; and the pH of the composition is about 5.0.

65. An article of manufacture, comprising packaging material, an aqueous composition comprising the composition of claim 1 formulated for single dosage administration, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction.

66. An article of manufacture, comprising packaging material, the composition of claim 53 formulated for single dosage administration, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction.

67. An article of manufacture, comprising packaging material, the composition of claim 58 formulated for single dosage administration, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction.

68. The pharmaceutical composition of claim 1, further comprising one or more of (a) to (j) as follows: (a) a $\beta_2$-adrenoreceptor agonist; (b) a dopamine ($D_2$) receptor agonist; (c) an IL-5 inhibitor; (d) an antisense modulator of IL-5; (e) a tryptase inhibitor; (f) a tachykinin receptor antagonist; (g) milrinone or milrinone lactate; (h) a leukotriene receptor antagonist; (i) a 5-lypoxygenase inhibitor; or (j) an anti-IgE antibody.

69. The pharmaceutical composition of claim 11, wherein the buffer comprises citric acid/phosphate buffer, acetate buffer, citrate buffer or phosphate buffer.

70. The pharmaceutical composition of claim 27, wherein the buffer comprises citric acid/phosphate buffer, acetate buffer, citrate buffer or phosphate buffer.

71. The pharmaceutical composition of claim 13, wherein the buffer concentration is from about 1 mM to about 50 mM.

72. The pharmaceutical composition of claim 71, wherein the buffer concentration is about 20 mM.

73. The pharmaceutical composition of claim 30, wherein the buffer concentration is from about 1 mM to about 50 mM.

74. The pharmaceutical composition of claim 73, wherein the buffer concentration is about 20 mM.

75. The pharmaceutical composition of claim 42, wherein the buffer concentration is about 20 mM.

76. The pharmaceutical composition of claim 42, wherein the buffer is citrate buffer; the buffer concentration is about 20 mM; the ionic strength of the composition is about 0.05 to about 0.16; and the pH of the composition is about 5.0.

77. The pharmaceutical composition of claim 43, wherein the buffer concentration is about 20 mM.

78. The pharmaceutical composition of claim 43, wherein the buffer is citrate buffer; the buffer concentration is about 20 mM; the ionic strength of the composition is about 0.05 to about 0.16; and the pH of the composition is about 5.0.

79. The pharmaceutical composition of claim 76 that has been nebulized.

80. The pharmaceutical composition of claim 78 that has been nebulized.

81. The combination of claim 62, wherein the aqueous composition comprises (a) formoterol free base at a concentration of about 59 µg/mL; (b) aqueous saline comprising sodium chloride; and (c) citrate buffer at a concentration of about 20 mM;
wherein the ionic strength of the composition is about 0.05 to about 0.16; and the pH of the composition is about 5.0.

82. The combination of claim 62, wherein the aqueous composition comprises (a) formoterol free base at a concentration of about 118 µg/mL; (b) aqueous saline comprising sodium chloride; and (c) citrate buffer at a concentration of about 20 mM;
wherein the ionic strength of the composition is about 0.05 to about 0.16; and the pH of the composition is about 5.0.

83. The pharmaceutical composition of claim 1, further comprising an anticholinergic agent.

84. The pharmaceutical composition of claim 83, wherein the anticholinergic agent is ipratropium bromide, oxitropium bromide, atropine methyl nitrate, tiotropium bromide or glycopyrronium bromide.

85. The pharmaceutical composition of claim 84, wherein the anticholinergic agent is ipratropium bromide.

86. The pharmaceutical composition of claim 85, wherein the ipratropium bromide is present at a concentration of about 5 µg/mL to about 5 mg/mL.

87. The pharmaceutical composition of claim 84, wherein the anticholinergic agent is tiotropium bromide.

88. The pharmaceutical composition of claim 85, wherein the tiotropium bromide is present at a concentration of about 5 µg/mL to about 5 mg/mL.

* * * * *

UNITED STATES PATENT AND TRADEMARK OFFICE
CERTIFICATE OF CORRECTION

PATENT NO. : 6,667,344 B2
DATED : December 23, 2003
INVENTOR(S) : Banerjee et al.

It is certified that error appears in the above-identified patent and that said Letters Patent is hereby corrected as shown below:

Title page,
Item [56], References Cited, OTHER PUBLICATIONS, please add the following:

-- Lipworth *et al.*, "Effects of treatment with formoterol on bronchoprotection against methacholine," *Am. J. Med.* 104:431-438 (1998). --

Signed and Sealed this

Twentieth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,667,344 B2
APPLICATION NO. : 09/887281
DATED : December 23, 2003
INVENTOR(S) : Partha S. Banerjee et al.

It is certified that error appears in the above-identified patent and that said Letters Patent is hereby corrected as shown below:

At column 1, claim number 1, line number 31, "pharmecutical" should be changed to --pharmaceutical--;

At column 1, claim number 1, line number 35, "effect" should be changed to --effective--.

At column 3, claim number 102, line number 8, "citratic" should be changed to --citric--;

At column 3, claim number 106, line number 26, "wherein the formoterol" should be changed to wherein --said-- formoterol;

At column 3, claim number 106, line number 27, "stereoisomer optically" should be changed to stereoisomer --is-- optically;

At column 3, claim number 109, line number 45-46, "tartate" should be changed to --a tartrate--.

Signed and Sealed this
Third Day of January, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 6,667,344 B2 |
| APPLICATION NO. | : 09/887281 |
| DATED | : December 23, 2003 |
| INVENTOR(S) | : Partha S. Banerjee et al. |

It is certified that error appears in the above-identified patent and that said Letters Patent is hereby corrected as shown below:

This certificate supersedes the Certificate of Correction issued January 12, 2012. The certificate is vacated since errors appearing on the Certificate of Correction does not correspond to text in the printed patent. The Certificate of Correction should not have been issued.

Signed and Sealed this
Thirty-first Day of January, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,667,344 C1 | Page 1 of 1 |
| APPLICATION NO. | : 90/010488 | |
| DATED | : October 11, 2011 | |
| INVENTOR(S) | : Partha S. Banerjee et al. | |

It is certified that error appears in the above-identified patent and that said Letters Patent is hereby corrected as shown below:

At column 1, claim number 1, line number 31, "pharmecutical" should be changed to --pharmaceutical--;

At column 1, claim number 1, line number 35, "effect" should be changed to --effective--.

At column 3, claim number 102, line number 8, "citratic" should be changed to --citric--;

At column 3, claim number 106, line number 26, "wherein the formoterol" should be changed to wherein --said-- formoterol;

At column 3, claim number 106, line number 27, "stereoisomer optically" should be changed to stereoisomer --is-- optically;

At column 3, claim number 109, line number 45-46, "tartate" should be changed to --a tartrate--.

Signed and Sealed this
Seventh Day of February, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 6,667,344 B2 |
| APPLICATION NO. | : 09/887281 |
| DATED | : December 23, 2003 |
| INVENTOR(S) | : Partha S. Banerjee et al. |

It is certified that error appears in the above-identified patent and that said Letters Patent is hereby corrected as shown below:

This certificate supersedes the Certificate of Correction issued January 3, 2012 and January 31, 2012. The certificate is vacated since errors appearing on the Certificate of Correction does not correspond to text in the printed patent. The Certificates of Correction should not have been issued.

Signed and Sealed this
Twenty-eighth Day of February, 2012

David J. Kappos
*Director of the United States Patent and Trademark Office*

UNITED STATES PATENT AND TRADEMARK OFFICE
CERTIFICATE OF CORRECTION

PATENT NO. : 6,667,344 C1  
APPLICATION NO. : 90/010488  
DATED : October 11, 2011  
INVENTOR(S) : Partha S. Banerjee et al.

Page 1 of 1

It is certified that error appears in the above-identified patent and that said Letters Patent is hereby corrected as shown below:

Title Page, Item (73) Assignee should read -- Dey, L.P., Napa, CA (US) --

Signed and Sealed this
Fifteenth Day of July, 2014

Michelle K. Lee
*Deputy Director of the United States Patent and Trademark Office*

(12) EX PARTE REEXAMINATION CERTIFICATE (8624th)
United States Patent
Banerjee et al.

(10) Number: US 6,667,344 C1
(45) Certificate Issued: Oct. 11, 2011

(54) BRONCHODILATING COMPOSITIONS AND METHODS

(75) Inventors: Partha S. Banerjee, Davis, CA (US);
Stephen Pham, Sacramento, CA (US);
Samuel O. Akapo, Vacaville, CA (US);
Imtiaz A. Chaudry, Napa, CA (US)

(73) Assignee: JPMorgan Chase Bank, N.A., Chicago, IL (US)

Reexamination Request:
No. 90/010,488, May 11, 2009

Reexamination Certificate for:
Patent No.: 6,667,344
Issued: Dec. 23, 2003
Appl. No.: 09/887,281
Filed: Jun. 22, 2001

Certificate of Correction issued Apr. 20, 2004.

Related U.S. Application Data

(60) Provisional application No. 60/284,606, filed on Apr. 17, 2001.

(51) Int. Cl.
| | |
|---|---|
| *A61K 9/12* | (2006.01) |
| *A61K 9/00* | (2006.01) |
| *A61K 31/135* | (2006.01) |
| *A61K 31/16* | (2006.01) |
| *A61K 31/165* | (2006.01) |
| *A61K 31/167* | (2006.01) |
| *A61K 31/35* | (2006.01) |
| *A61K 31/375* | (2006.01) |
| *A61K 31/444* | (2006.01) |
| *A61K 31/46* | (2006.01) |
| *A61K 31/56* | (2006.01) |
| *A61K 31/58* | (2006.01) |
| *A61K 39/395* | (2006.01) |
| *A61K 45/00* | (2006.01) |
| *A61K 47/04* | (2006.01) |
| *A61K 47/10* | (2006.01) |
| *A61K 47/12* | (2006.01) |
| *A61K 47/16* | (2006.01) |
| *A61K 47/18* | (2006.01) |
| *A61K 47/22* | (2006.01) |
| *A61K 47/26* | (2006.01) |
| *A61K 47/38* | (2006.01) |
| *A61K 31/4427* | (2006.01) |
| *A61K 47/02* | (2006.01) |
| *A61L 9/04* | (2006.01) |
| *A61P 11/06* | (2006.01) |
| *A61P 11/08* | (2006.01) |
| *A61P 11/00* | (2006.01) |

(52) U.S. Cl. .................. 514/653; 424/45; 424/46
(58) Field of Classification Search .......... None
See application file for complete search history.

(56) References Cited

U.S. PATENT DOCUMENTS

| | | |
|---|---|---|
| 3,929,768 A | 12/1975 | Brattsand et al. |
| 3,994,974 A | 11/1976 | Murakami et al. |
| 4,335,121 A | 6/1982 | Phillipps et al. |
| 4,578,221 A | 3/1986 | Phillipps et al. |
| 4,826,689 A | 5/1989 | Violanto et al. |
| 4,985,418 A | 1/1991 | Richards |
| 4,992,474 A | 2/1991 | Skidmore et al. |
| 5,033,252 A | 7/1991 | Carter |
| 5,052,558 A | 10/1991 | Carter |
| 5,126,123 A | 6/1992 | Johnson |
| 5,126,375 A | 6/1992 | Skidmore et al. |
| 5,145,684 A | 9/1992 | Liversidge et al. |
| 5,225,445 A | 7/1993 | Skidmore et al. |
| 5,270,305 A | 12/1993 | Palmer |
| 5,284,656 A | 2/1994 | Platz |
| 5,290,815 A | 3/1994 | Johnson et al. |
| 5,323,907 A | 6/1994 | Kalvelage |
| 5,376,359 A | 12/1994 | Johnson |
| 5,434,304 A | 7/1995 | Trofast et al. |
| 5,510,118 A | 4/1996 | Bosch et al. |

(Continued)

FOREIGN PATENT DOCUMENTS

| | | |
|---|---|---|
| DE | 2305092 | 8/1973 |
| DE | 19541689 | 5/1996 |
| DE | 19835346 | 2/2000 |
| DE | 19847970 | 4/2000 |
| EP | 0370632 | 5/1990 |
| EP | 0616525 | 9/1994 |
| EP | 1157689 | 11/2001 |
| EP | 1229034 | 8/2002 |
| EP | 1236467 | 9/2002 |
| WO | WO91/04984 | 4/1991 |
| WO | WO92/05147 | 4/1992 |
| WO | WO93/11773 | 6/1993 |
| WO | WO95/05805 | 3/1995 |
| WO | WO95/31964 | 11/1995 |
| WO | WO96/18384 | 6/1996 |

(Continued)

OTHER PUBLICATIONS

Ball, D.I., et al., "Salmeterol, a novel, long–acting $\beta_2$–adrenoceptor agonist: characterization of pharmacological activity in vitro and in vivo" (1991), Br. J. Pharmacol. 104, 665–671.

Barnes, "Scientific rationale for inhaled combination therapy with long–acting b2–agonists and corticosteroids," *Eur. Respir. J.*, 19:182–191 (2002).

Bartow et al., "An Update of its Pharmacological Properties and Therapeutic Efficacy in the Management of Asthma," *Drugs*, 55(2):303–322 (1998).

(Continued)

*Primary Examiner*—Dwayne Jones

(57) ABSTRACT

Bronchodilating compositions and methods are provided. The compositions are intended for administration as a nebulized aerosol. In certain embodiments, the compositions contain formoterol, or a derivative thereof. Methods for treatment, prevention, or amelioration of one or more symptoms of bronchoconstrictive disorders using the compositions provided herein are also provided.

U.S. PATENT DOCUMENTS

| | | | |
|---|---|---|---|
| 5,525,623 | A | 6/1996 | Spear et al. |
| 5,552,160 | A | 9/1996 | Liversidge et al. |
| 5,556,964 | A | 9/1996 | Hofstraat et al. |
| 5,602,110 | A | 2/1997 | Drumm et al. |
| 5,637,620 | A | 6/1997 | Trofast et al. |
| 5,647,347 | A | 7/1997 | Van Oort |
| 5,654,276 | A | 8/1997 | Barrett et al. |
| 5,658,549 | A | 8/1997 | Akehurst et al. |
| 5,668,110 | A | 9/1997 | Barrett et al. |
| 5,674,860 | A | 10/1997 | Carling et al. |
| 5,677,280 | A | 10/1997 | Barrett et al. |
| 5,677,809 | A | 10/1997 | Kadlec |
| 5,683,983 | A | 11/1997 | Barrett et al. |
| 5,691,336 | A | 11/1997 | Dorn et al. |
| 5,709,884 | A | 1/1998 | Trofast et al. |
| 5,733,526 | A | 3/1998 | Trevino et al. |
| 5,736,124 | A | 4/1998 | Akehurst et al. |
| 5,750,549 | A | 5/1998 | Caldwell et al. |
| 5,753,218 | A | 5/1998 | Smith et al. |
| 5,780,467 | A | 7/1998 | Dorn et al. |
| 5,785,952 | A | 7/1998 | Taylor et al. |
| 5,795,564 | A | 8/1998 | Aberg et al. |
| 5,823,182 | A | 10/1998 | Van Oort |
| 5,849,265 | A | 12/1998 | Li-bovet et al. |
| 5,874,063 | A | 2/1999 | Briggner et al. |
| 5,874,481 | A | 2/1999 | Weers et al. |
| 5,877,191 | A | 3/1999 | Caldwell et al. |
| 5,916,540 | A | 6/1999 | Akehurst et al. |
| 5,919,435 | A | 7/1999 | Taylor et al. |
| 5,922,306 | A | 7/1999 | Akehurst et al. |
| 5,929,094 | A | 7/1999 | Durette et al. |
| 5,955,439 | A | 9/1999 | Green |
| 5,965,622 | A | 10/1999 | Senanayake |
| 5,972,327 | A | 10/1999 | Lin et al. |
| 5,972,919 | A | 10/1999 | Carling et al. |
| 5,972,920 | A | 10/1999 | Seidel et al. |
| 5,980,949 | A | 11/1999 | Trofast |
| 5,983,956 | A | 11/1999 | Trofast |
| 5,993,781 | A | 11/1999 | Snell et al. |
| 5,993,782 | A | 11/1999 | Gardner |
| 6,001,336 | A | 12/1999 | Gordon |
| 6,004,537 | A | 12/1999 | Blondino et al. |
| 6,027,714 | A | 2/2000 | Trofast |
| 6,030,604 | A | 2/2000 | Trofast |
| 6,040,344 | A | 3/2000 | Gao et al. |
| 6,041,777 | A | 3/2000 | Faithfull et al. |
| 6,068,833 | A | 5/2000 | Aberg et al. |
| 6,068,860 | A | 5/2000 | Carlsson et al. |
| 6,071,971 | A | 6/2000 | Senanayake |
| 6,123,924 | A | 9/2000 | Mistry et al. |
| 6,126,919 | A | 10/2000 | Stefely et al. |
| 6,136,603 | A | 10/2000 | Dean et al. |
| 6,150,418 | A | 11/2000 | Hochrainer et al. |
| 6,153,173 | A | 11/2000 | Sapsford et al. |
| 6,161,536 | A | 12/2000 | Redmon et al. |
| 6,183,782 | B1 | 2/2001 | Hallworth |
| 6,199,607 | B1 | 3/2001 | Trofast et al. |
| 6,200,549 | B1 | 3/2001 | Akehurst et al. |
| 6,221,398 | B1 | 4/2001 | Jakupovic et al. |
| 6,235,725 | B1 | 5/2001 | Ahmed |
| 6,241,969 | B1 | 6/2001 | Saidi et al. |
| 6,251,368 | B1 | 6/2001 | Akehurst et al. |
| 6,253,762 | B1 | 7/2001 | Britto |
| 6,261,539 | B1 | 7/2001 | Adjei et al. |
| 6,287,540 | B1 | 9/2001 | Trofast |
| 6,287,693 | B1 | 9/2001 | Savoir et al. |
| 6,291,445 | B1 | 9/2001 | Nilsson et al. |
| 6,303,145 | B2 | 10/2001 | Jerussi et al. |
| 6,306,368 | B1 | 10/2001 | Taylor et al. |
| 6,306,369 | B1 | 10/2001 | Akehurst et al. |
| 6,309,623 | B1 | 10/2001 | Weers et al. |
| 6,309,624 | B1 | 10/2001 | Sapsford et al. |
| 6,365,190 | B1 | 4/2002 | Gordon et al. |
| 6,369,115 | B1 | 4/2002 | Ward |
| 6,406,718 | B1 | 6/2002 | Cooper |
| 6,413,496 | B1 | 7/2002 | Goodman et al. |
| 6,416,742 | B1 | 7/2002 | Stefely et al. |
| 6,423,298 | B2 | 7/2002 | McNamara et al. |
| 6,448,296 | B2 | 9/2002 | Yasueda et al. |
| 6,451,287 | B1 | 9/2002 | Desimone et al. |
| 6,461,591 | B1 | 10/2002 | Keller et al. |
| 6,464,958 | B1 | 10/2002 | Bernini et al. |
| 6,475,467 | B1 | 11/2002 | Keller et al. |
| 6,479,035 | B1 | 11/2002 | Cripps et al. |
| 6,481,435 | B2 | 11/2002 | Hochrainer et al. |
| 6,482,390 | B1 | 11/2002 | Hiscocks et al. |
| 6,598,603 | B1 | 7/2003 | Andersson et al. |
| 6,632,842 | B2 | 10/2003 | Chaudry et al. |
| 6,667,344 | B2 | 12/2003 | Banerjee et al. |
| 6,686,346 | B2 | 2/2004 | Nilsson et al. |
| 6,702,997 | B2 | 3/2004 | Chaudry et al. |
| 6,814,953 | B2 | 11/2004 | Banerjee et al. |
| 6,816,510 | B1 | 11/2004 | Banerjee |
| 7,070,800 | B2 | 7/2006 | Bechtold-Peters et al. |
| 7,348,362 | B2 | 3/2008 | Banerjee et al. |
| 7,462,645 | B2 | 12/2008 | Chaudry et al. |
| 7,465,756 | B2 | 12/2008 | Chaudry et al. |
| 7,473,710 | B2 | 1/2009 | Chaudry et al. |
| 7,541,385 | B2 | 6/2009 | Chaudry et al. |
| 2001/0024641 | A1 | 9/2001 | Yang |
| 2002/0032148 | A1 | 3/2002 | Kensey |
| 2002/0042404 | A1 | 4/2002 | Bauer et al. |
| 2002/0061835 | A1 | 5/2002 | Kensey |
| 2002/0081266 | A1 | 6/2002 | Woolfe et al. |
| 2002/0099013 | A1 | 7/2002 | Piccariello et al. |
| 2002/0103260 | A1 | 8/2002 | Clarke et al. |
| 2002/0151597 | A1 | 10/2002 | Banerjee et al. |
| 2002/0151598 | A1 | 10/2002 | Banerjee et al. |
| 2002/0183293 | A1 | 12/2002 | Banerjee |
| 2003/0055026 | A1 | 3/2003 | Banerjee et al. |
| 2003/0109510 | A1 | 6/2003 | Gavin |
| 2003/0124063 | A1 | 7/2003 | Chaudry et al. |
| 2004/0023935 | A1 | 2/2004 | Banerjee et al. |
| 2004/0109826 | A1 | 6/2004 | Malledi et al. |
| 2004/0110845 | A1 | 6/2004 | Malladi et al. |
| 2005/0009923 | A1 | 1/2005 | Banerjee et al. |
| 2007/0160541 | A1 | 7/2007 | Chaudry |
| 2007/0166235 | A1 | 7/2007 | Banerjee |
| 2007/0166236 | A1 | 7/2007 | Banerjee |
| 2007/0166240 | A1 | 7/2007 | Banerjee |

FOREIGN PATENT DOCUMENTS

| | | |
|---|---|---|
| WO | WO96/19198 | 6/1996 |
| WO | WO96/19968 | 7/1996 |
| WO | WO96/32095 | 10/1996 |
| WO | WO97/47286 | 12/1997 |
| WO | WO98/05302 | 2/1998 |
| WO | WO98/15280 | 4/1998 |
| WO | WO98/24450 | 6/1998 |
| WO | WO98/31350 | 7/1998 |
| WO | WO98/31351 | 7/1998 |
| WO | WO98/31352 | 7/1998 |
| WO | WO98/34595 | 8/1998 |
| WO | WO98/34596 | 8/1998 |
| WO | WO98/41193 | 9/1998 |
| WO | WO98/52544 | 11/1998 |
| WO | WO99/00134 | 1/1999 |
| WO | WO99/15182 | 4/1999 |
| WO | WO99/25359 | 5/1999 |
| WO | WO99/30703 | 6/1999 |
| WO | WO99/36095 | 7/1999 |

| | | |
|---|---|---|
| WO | WO99/40939 | 8/1999 |
| WO | WO99/48476 | 9/1999 |
| WO | WO99/53926 | 10/1999 |
| WO | WO99/61003 | 12/1999 |
| WO | WO99/64014 | 12/1999 |
| WO | WO99/65464 | 12/1999 |
| WO | WO00/00181 | 1/2000 |
| WO | WO00/03613 | 1/2000 |
| WO | WO00/06121 | 2/2000 |
| WO | WO00/07567 | 2/2000 |
| WO | WO00/16814 | 3/2000 |
| WO | WO00/23037 | 4/2000 |
| WO | WO00/23065 | 4/2000 |
| WO | WO00/28979 | 5/2000 |
| WO | WO00/30612 | 6/2000 |
| WO | WO00/33892 | 6/2000 |
| WO | WO00/47200 | 8/2000 |
| WO | WO00/48587 | 8/2000 |
| WO | WO00/51591 | 9/2000 |
| WO | WO00/53187 | 9/2000 |
| WO | WO00/53188 | 9/2000 |
| WO | WO01/22956 | 4/2001 |
| WO | WO01/27107 | 4/2001 |
| WO | WO01/32163 | 5/2001 |
| WO | WO01/39745 | 6/2001 |
| WO | WO01/54664 | 8/2001 |
| WO | WO01/70198 | 9/2001 |
| WO | WO01/78735 | 10/2001 |
| WO | WO01/78737 | 10/2001 |
| WO | WO01/78745 | 10/2001 |
| WO | WO01/83517 | 11/2001 |
| WO | WO01/85137 | 11/2001 |
| WO | WO01/89491 | 11/2001 |
| WO | WO01/89492 | 11/2001 |
| WO | WO02/03958 | 1/2002 |
| WO | WO02/07672 | 1/2002 |
| WO | WO02/11803 | 2/2002 |
| WO | WO02/28368 | 4/2002 |
| WO | WO02/30394 | 4/2002 |
| WO | WO02/34237 | 5/2002 |
| WO | WO02/38107 | 5/2002 |
| WO | WO02/43806 | 6/2002 |
| WO | WO02/45682 | 6/2002 |
| WO | WO02/49616 | 6/2002 |
| WO | WO02/051483 | 7/2002 |
| WO | WO02/060532 | 8/2002 |
| WO | WO02/060533 | 8/2002 |
| WO | WO02/060875 | 8/2002 |
| WO | WO02/060896 | 8/2002 |
| WO | WO02/060898 | 8/2002 |
| WO | WO02/062317 | 8/2002 |
| WO | WO02/083079 | 10/2002 |
| WO | WO02/083113 | 10/2002 |
| WO | WO03/024433 | 3/2003 |
| WO | WO03/047578 | 6/2003 |
| WO | WO2005/007142 | 1/2005 |

OTHER PUBLICATIONS

Becker et al., "Formoterol, a new long–acting selective b2–adrenergic receptor agonist: Double–blind comparison with salbutamol and placebo in children with asthma" *J. Allergy Clin. Immunol.*, 84:891–895 (1989).

Bedi, "Inhaled Corticosteroids in COPD," *Indian J Chest Allied Sci*, 47:243–244 (2005).

Berger, "Aerosol Devices and Asthma Therapy" Current Drug Delivery, 2009, 6, 38–49.

Campbell et al., "A comparison of the efficacy of long–acting B2–agonists:eformoterol via Turbohaler( 4) and salmeterol via pressurized metered dose inhaler or Accuhaler(R), in mild to moderate asthmatics," *Respiratory Medicine*, 93:236–244 (1999).

Campestrini et al., "Automated and sensitive method of the determination of formoterol in human plasma by high–performance liquid chromatography and electrochemical detection," *Journal of Chromatography B*, 704:221–229 (1997).

Cazzola et al., "Long–Acting b2–Agonists in the Treatment of Acute Exacerbations of COPD," *Clin. Drug Invest.*, 22(6): 168–174 (2002).

Daugbjerg et al., "Duration of action of formoterol and salbutamol dry–powder inhalation in prevention of exercise–induced asthma in children," *Acta Paediatr.*, 85:684–687 (1998).

Dellamary et al., "Hollow Porous Particles in Meterd Dose Inhalers," *Pharmaceutical Research*, 17(2):168–174 (2000).

Derwent #000971705, WPI Acc. No. 1973–48969U/197335 citing German Patent Application No. DE 2305092 A, "Alphaaminomethylbenzyl alcohol derives. –prepd. by redn. Of corresponding protected derives.", date unavailable.

Derwent #010743444, WPI Acc No. 1996–2403991199625 for German Patent Application DE 19541689, "Medicament contg. ciclesonid and beta2–sympathomimetic for treating chronic obstructive respiratory disease", 1996.

Derwent #012030009, EPI Acc No. 1998–446919–199838 for PCT Patent Application WO 98/34595, "Pressurised liquid aerosol propellant for pharmaceutical inhalers—contains carbondioxide and hydro–fluoroalkane; give more consistent dosing and abetter particle size spectrum", 1998.

Derwent #013011051, WPI Acc No. 2000–182903/200016 for PCT Patent Application WO 00106121, "Aerosol propellant comprising dinitrogen monoxide and hydrofluoroalkane and optionally containing a pharmaceutically active substance", 2000.

Derwent #013023586, WPI Acc No. 2000–195437/200017, for PCT Patent Application WO 00107567, "Aerosol formulation of rdrug administration, containing small amount of cromoglycate or nedocromil salt as drug carrier, to improve dispersion stability and accuracy of dosing", 2000.

Derwent #013024375, WPI Acc No. 2000–196226/200018 for German Patent Application DE 19835346, "Two–part drug capsule for use in powder inhalers is formed from hydrophobic plastics, preferably high density polyethylene", 2001.

Derwent #013132855, WPI Acc No. 2000–3047261200027, for German Patent De 19847970, "Stable concentrated liquid formulation of inhalable drug, e.g. formoterol or salbutamol, in solution or suspensionmedium, used after dilution for treatment of respiratory disorders by inhalation", 2000.

Derwent #013227765, WPI Acc No. 2000–3996391200034, for PCT Patent Application WO 00128979, "Use of magnesium state for stabilization of dry powder inhalation formulations to improve resistance to moisture", 2000.

Derwent #013790372, WPI Acc No. 2001–274583/200129, for PCT Patent Application WO 01122956, "Drug combination of soft steroid and beta–2–adrenorecetptor agonist, administered by inhalation for effective treatment of respiratory or allergic diseases, e.g. asthma", 2001.

Derwent #014808338, EPI Acc No. 2002–829044/200268, for PCT Patent Application WO 021060533, "Medicament containing a betamimetic and an oxitropium slat useful for the treatment of respiratory disorders with reduced side effects", 2002.

Derwent #014816787, EIP Acc No. 2002–637493/200269, for PCT Patent Application Woo 021060532, "Medicament containing a betamimetic and an ipratropium salt useful for the treatment of respiratory disorders with reduced side effects", 2002.

Derwent WPI Acc No. 2000–304726 for PCT Patent Application WO 00123037, "Stable concentrated liquid formulation of inhalable drug, e.g. formoterol or salbutamol, in solution or suspension medium, used after dilution for treatment of respiratory disorders by inhalation", 2000.

Dolovich, "Device Selection and Outcomes of Aerosol Therapy: Evidence–Based Guidelines" Chest 2005, 127, 335–371.

Eidkelberg et al., "Ligand–independent Activation of the Glucocorticoid Receptor by b2–Adrenergic Recaptor Agonists in Primary Human Lung Fibroblasts and Bascular Smooth Muscle Cell," J. Biol. Chem., 272(2):1005–1010 (1999).

Ekstrom et al., "Low–dose formoterol Turbuhaler(R) (Oxis(R>> b.i.d., a 3–month placebo–controlled comparison with terbutaline (q.i.d.)," Respiratory Medicine, 92:1040–1045 (1998).

Farmer et al., "b–Adrenergic agonists exert their "anti–inflammatory" effects in monocytic cells through the lκB/NF–κB pathway," Am. J. Physiol. Lung. Cell. Mol. Physiol., 279:1675–682 (2000).

"Flovent," Glaxo Wellcome Inc., Physicians' Desk Reference, 54th Ed., (2000), pp. 1186–1189.

Geller, Comparing Clinical Features of the Nebulizer, Metered–Dose Inhaler, and Dry Powder Inhaler, Respiratory Care, Oct. 2005, vol. 50 No. 10 pgs. 1313–1322.

Greening et al., "Added salmeterol versus higher–dose corticosteroid in asthma patients with symptoms on existing inhaled corticosteroid," The Lancet, 344:219–244 (1994).

Grootendorst et al., "Effect of oral prednisolone on the bronchoprotective effect of formoterol in patient with persistent asthma," Eur. Respir. J., 17:374–379 (2001).

Hardman et al. (Eds.), Goodman Gilman's The Pharmacological Basis of Therapeutics, p. 665 (1996).

Hess, Respiratory Care, Jun. 2008, vol. 53 No. 6, 699–725.

Hess, Aerosol delivery during mechanical ventilation, Minerva Anestisiologica, vol. 68 No. 5 (2002) pp. 321–325.

Ida, "Cardiorespiratory Activities of 3–Formylamino–4–hydroxy–a(N–1–methyl–2–p–methoxyphenethylarnino–methyl)benzylalcoholhemifumarate (BD 40A) and some other b–Adrenoceptor Stimulants in Conscious Guinea Pigs," Arzneim.–Forsch. (Drug Res.), 26:1337–1340 (1976).

Ida, "Comparison of the Action of BD 40A and some Other b–Adrenoceptor Stimulants on the Isolated Trachea and Atria of the Guinea Pig," Arzneim.–Forsch. (Drug Res.), 26:839–842 (1976).

Ida, Hisashi, "Pharmacology of Formoterol, (aRS)–3–formamido–4–hydroxy–a[[[(aRS)–p–methoxy–amethyl–phenethyl]amino]methyl]benzyl alcohol fumatate dehydrate (BD 40A)," Oyo Yakui, 21(2):201–210 (1981).

Ikeda, et al., Comparison of the Bronchodilator Effects of Salbutamol Delivered via a Metered–Dose Inhaler with Spacer, a Dry–Powder Inhaler, and a Jet Nebulizer in Patients with Chronic Obstructive Pulmonary Disease, Respiration (1999) 66:119–123.

Ito et al., "Glucocorticoid Receptor Recruitment of Histone Deacetylase 2 Inhibits Interleukin–lb–Induced Histone H4 Acetylation of Lysines 8 and 12," Molecular and Cellular Biology, 20(18):6892–6903 (2000).

Ito et al., "p65–activated Histone Acetyltransferase Activity is Repressed by Glucocorticoids," J. Biol. Chem., 276(32):30208–30215 (2001).

Kamimura et al. "Quantitative Determination of the b–adrenoceptor stimulant Formoterol in Urine by Gas Chromatograph Mass Sptectrometry," J. Chromo, 229:337–345 (1982).

Kaumann et al., "Direct Labelling of myocardial B1–adrenoreceptors; Comparison of Binding Affinity of 3H–(—)–bisoprolol with its blocking potency," Arch. Pharm., 331:27–39 (1985).

Kibbe, A.H. (ed.), Handbook of Pharmaceutical Excipients, 3rd Ed., "Citric Acid Monohydrate," pp. 140–142 (2000).

Korn et al., "Effects offormoterol and budesonide on GM–CSF and IL–8 secretion by triggered human bronchial epithelial cells," Eur. Respir. J., 17:1070–1077 (2001).

Lachman et al., "Chapter 26. Kinetic Principles and Stability Testing," The Theory and Practice of Industrial Pharmacy, 3rdEdition, pp. 760–803, (1986).

Lebecque et al. "Effet d'une dose unique de formoterol par voie daerosol–doseur chez l'enfant asthmatique," Rev. Mal. Resp., 11:47–50 (1994).

Lecaillon et al., "Parmacokinetics and tolerability of formoterol in healthy volunteers after a single high dose of Foradil dry powder inhalation via aerolizer (TM)," Eur. J. Clin. Pharm., 55:131–139 (1999).

Leckie et al., "Novel Therapy of COPD," Expert Opin. Investig. Drugs, 9(1):3–23 (2000).

Lemoine et al., "Direct labeling of B2–adrenoreceptors; Comparison of binding potency of3H–ICI 118,551 and blocking potency of ICI 118,551," Arch. Pharm., 331:40–51 (1985).

Lipworth et al., "Effects of Treatment with Formoterol on Bronchoprotection against Methacholine," Am. J. Med., 104:431–438 (1998).

Lofdahl et al. "Formoterol Fumarate, a new b2–adrenoceptor agonist," Allergy, 44:264–271 (1989).

Lotvall et al., "Similar bronchodilation with formoterol delivered by Aerolizer or Turbuhaler," Can. Respir. J., 6(5):412–416 (1999).

Maesen et al. "Formoterol as Dry Powder Inhalation," Chest, 101:1376–1381 (1992).

Maesen et al. "Formoterol Suspension Aerosol" Chest 102: 1544–1549 (1992).

Maesen et al. "The Effect of Maximal Doses of Formoterol and Salbutamol from a Metered Dose Inhaler on Pulse Rates, ECG, and Serum Potassium Concentrations," Chest, 99:1367–1373 (1991).

Malolepszy et al., "Safety of formoterol Turbuhaler(TM) at cumulative dose of 90 mg in patients with acute bronchial obstruction," Eur. Respir. J., 18:928–934 (2001).

Miller et al. "Chronic Effects of the Novel Glucocorticosteroid RPR 106541 Administered to Beagle Dogs by Inhalation" Toxic. Path., 28:226–236 (2000).

Mohammed et al., "Duration of action of inhaled vs. Intravenous β2–adrenoceptor . . . ", *Pulmonary Pharmacology & Therapeutics*, 13:287–292 (2000).

Murase et al. "New b–Adrenoreceptor Stimulants. Studies on 3–Acylamino–4–hydroxy–a–(N–substituted aminomethyl)benzyl Alcohols," *Chem Pharm. Bull.*, 26:1368–1377 (1977).

Nials, A.T., et al., "Effects of β–adrenoceptor agonists in human bronchial smooth muscle", *Br. J. Pharmacol.*, 110:1112–1116 (1993).

Nials, A.T., et al., "Formoterol on airway smooth muscle and human lung mast cells:.", *European Journal of Pharmacology*, 251:127–135 (1994).

Nielsen et al., "Flow–dependent effect of formoterol dry powder inhaled from the Aerolizer(R)," *Eur. Respir. J.*, 10:2105–2109 (1997).

Nightingale et al., "Differential Effect of Formoterol on Adenosine Monophophate and Histamine Reactivity in Asthma," *Am. J. Respir. Crit. Care Med.*, 159 1786–1790 (1999).

Nogrady. T., (Editor), Medicinal Chemistry: A Biochemical Approach, Oxford University Press, New York, pp. 388–392 (1985).

O'Connor, "Combination Therapy," *Pulm. Pharm. & Ther.*, 11:379–399 (1998).

Oddera et al., "Salmetereol Enhances the Inhibitor Activity of Dexamethasone on Allergen–Induced Blood Mononuclear Cell Activation," *Respiration*, 65: 199–204 (1998).

On–line Orange Book Listing for Dey's "Perforomist," formoterol for nebulization.

Package Insert for: Advair(TM) Discus http://fb.a–files.netl Packageinsert? Advair.htm (Accessed on Sep. 26, 2002) (Copyright, 1999 Glaxo Wellcome Inc.).

Palmqvist et al., "Inhaled dry–powder formoterol and almeterol in asthmatic patients: onset on action, duration of effect and potency," *Eur. Respir. J.*, 10:2484–2489 (1997).

Palmqvist et al , "Onset of Bronchodilation of Budesonide?formoterol vs. Salmeterol/Fluticasone in Single inhalers," *Pulm. Pharm. & Ther.*, 14:29–34 (2001).

Pang et al., "Regulation of TNF–a–induced eotaxin release from cultured human airway smooth muscle cells by b2–agonists and corticoseroids," *FASEB J.*, 15:261–269 (2001).

Pang et al., "Synergistic Inhibition by b2–Agonists and Corticosteroids on Tumor Necrosis Factor–a–Induced Interleukin–8 Release from Cultured Human Airway Smooth–Muscle Cells," *Am. J. Respir. Cell Mol. Bio.*, 23:79–85 (2000).

Pauwels et al., "Effect of Inhaled Formoterol and Budesonide on Exacerbations of Asthma," *The New England J. Med.*, 337(20): 1405–1411 (1997).

Physicians' Desk Reference: PDR, Oradell, J.J.: Medical Economics, Co., pp. 535–537, 480–482, 2828–2829 (2000).

Puigbo, et al., "A New Alternative Therapy In The Management Of Acute Asthma" Allergy, Asthma and Immunology, vol. II No. 2 (2000).

Rau, *Practical Problems With Aerosol Therapy in COPD*, Respiratory Care, Feb. 2006 vol. 51 No. 2, pp. 158–172.

Remington, "Chapter 38, Stability of Pharmaceutical Products," Remington: The Science and Practice of Pharmacology, 19th Edition, vol. 1, pp. 635–647, (1995).

Remington's Pharmaceutical Sciences, Seventeenth Edition, pp. 1443 and 1451 (1985).

Rico–Mendez et al., "Formoterol en polvo seco, dos veces al dia versus salbutamol aerosol, cuatro veces al dia, en pacientes con asma estable," *Revista Alergia Mexico XLVI*, (5):130–135 (1999).

Ringdal et al., "Onset and duration of action of single doses of formoterol inhaled via Turbuhaler(R)," *Resp. Med.*, 92:1017–1021 (1998).

Sasaki et al. "Desposition and metabolism of formoterol fumarate, a new bronchodilator, in rats and dogs" *Xenobiotic*, 12:803–812 (1982).

Sasaki et al. "Desposition and metabolism of formoterol fumarate, a new bronchodilator, in rats and dogs" *Xenobiotic*, vol. 12, pp. 803–809 (1998).

Scheen, "Pharma–Clinics le Medicament du Mois le formoterol (Oxis Turbohaler)," *Rev. Med. Liege*, 53:11:715–718 (1998).

Schreurs et al., "A dose–response study with formoterol Turbuhaler(R) as maintenance therapy in asthmatic patients," *Eur. Respir. J.*, 9:1678–1683 (1996).

Seberova et al., "Oxis(R) (formoterol given by Turbuhale(R>> showed as rapid an onset of action as salbutamol given by a pMDI," *Resp. Med.*, 94:607–611 (2000).

Seldon et al., "Albuterol Does Not Antagonize the Inhibitory Effect on Dexamethasone on Monocyte Cytokine Release," *Am. J. Respir. Crit. Care Med.*, 157:803–809 (1998).

Selroos et al., "Delivery Devices for Inhaled Asthma Medication," *Clin. Immunother.*, 6:273–299 (1996).

Siegel, F., "Tonicity, osmoticity, osmolality and osmolarity," *Remington's Pharmaceutical Sciences*, Seventeenth Edition, Chaprter 80, pp. 1455–1472 (1985).

Silvestri et al., "Fluticasone and salmeterol donregulate in vitro, fibroblast proliferation and ICAM–I or H–CAM expression," *Eru. Respir. J.*, 18:139–145 (2001).

Skold et al., "Glucocorticoids Augment Fibroblast–Mediated Contration of Collagen Gels by Inhibition of Endogenous PGE Production," *Proc. Assoc. Am. Phys.*, 111(3):239–258 (1999).

Smaldone et al., "Budesonide Inhalation Suspension in Chemically Compatable with Other Nebulizing Formulations," *Chest*, 119(4) Suppl: 98S (2000).

Sovijarvi et al., "Preventive Effects of Inhaled Formoterol and Salbutamol on Histamine–Induced Bronchoconstriction–A Placebo–Controlled Study," *Respiration*, 59:279–282 (1992).

Stevens et al., "Use of the Steroid Derivative RPR 106541 in Combination wit Site–Directed Mutagenesis for Enhanced Cytochrome P–450 3A4 Structure/Function Analysis," *J. Pharma. Exp. Ther.*, 290:594–602 (1999).

Stewart et al., "Acute formoeterol administration has no argogenic effect in nonasthmatic athletes," *Medicine & Science in Sports & Exercise*, 34(2):213–217 (2002).

Tomioka et al., "Anti–Allergic Activities of the b–Adrenoreceptor Stimulant Formoterol (BD–40A)," *Arch. Int. Pharmacodyn.*, 250279–292 (1981).

Totterman et al. "Tolerability to high doses of formoterol and terbutaline via Turbuhaler(R) for 3 days in stable asthmatic patients," *Eur. Respir. J.*, 12:573–579 (1998).

U.S. Appl. No. 09/887,496: Advisory Action dated Oct. 8, 2003, 3 pages.

U.S. Appl. No. 09/887,496: Final Office Action dated May 20, 2003, 9 pages.

U.S. Appl. No. 09/887,496: Final Office Action dated Jan. 11, 2005, 15 pages.

U.S. Appl. No. 09/887,496: Final Office Action dated Mar. 13, 2007, 15 pages.
U.S. Appl. No. 09/887,496: Final Office Action dated Jun. 4, 2008, 17 pages.
U.S. Appl. No. 09/887,496: Final Office Action dated Jul. 22, 2009, 19 pages.
U.S. Appl. No. 09/887,496: Non–Final Office Action dated Apr. 24, 2002, 7 pages.
U.S. Appl. No. 09/887,496: Non–Final Office Action dated Dec. 18, 2002, 9 pages.
U.S. Appl. No. 09/887,496: Non–Final Office Action dated Jul. 1, 2004, 16 pages.
U.S. Appl. No. 09/887,496: Non–Final Office Action dated Jul. 5, 2006, 15 pages.
U.S. Appl. No. 09/887,496: Non–Final Office Action dated Aug. 27, 2007, 15 pages.
U.S. Appl. No. 09/887,496: Non–Final Office Action dated Oct. 28, 2008, 21 pages.
U.S. Appl. No. 09/887,496: Supplemental Advisory Action dated Dec. 19, 2003, 2 pages.
U.S. Appl. No. 10/145,978: Final Office Action dated May 12, 2004, 8 pages.
U.S. Appl. No. 10/145,978: Final Office Action dated Jan. 3, 2008, 11 pages.
U.S. Appl. No. 10/145,978: Final Office Action dated May 26, 2009, 11 pages.
U.S. Appl. No. 10/145,978: Interview Summary/Advisory Action dated May 13, 2008, 4 pages.
U.S. Appl. No. 10/145,978: Non–Final Office Action dated Aug. 26, 2003, 8 pages.
U.S. Appl. No. 10/145,978: Non–Final Office Action dated Dec. 29, 2004, 8 pages.
U.S. Appl. No. 10/145,978: Non–Final Office Action dated Sep. 28, 2005, 10 pages.
U.S. Appl. No. 10/145,978: Non–Final Office Action dated Jun. 11, 2007, 10 pages.
U.S. Appl. No. 10/145,978: Non–Final Office Action dated Aug. 20, 2008, 17 pages.
U.S. Patent No. 7,348,632 (U.S. Appl. No. 10/887,785): Non–Final Office Action dated Jun. 14, 2007, 7 pages.
U.S. Patent No. 7,462,645 (U.S. Appl. No. 11/688,429): Non–Final Office Action dated Oct. 18, 2007, 7 pages.
U.S. Patent No. 7,465,756 (U.S. Appl. No. 11/688,436): Non–Final Office Action dated Oct. 18, 2007, 7 pages.
U.S. Patent No. 7,473,710 (U.S. Appl. No. 11/688,450): Non–Final Office Action dated Oct. 17, 2007, 7 pages.
U.S. Patent No. 7,541,385 (U.S. Appl. No. 11/688,463): Non–Final Office Action dated Oct. 17, 2007, 7 pages.
U.S. Appl. No. 10/145,978: Final Office Action dated May 22, 2006, 11 pages.
Ullman et al., "Formoterol inhaled as dry powder or via pressurized meterd–dose inhaler in a cumulative dose–response study," *Allergy*, 51:745–748 (1996).
Van den Berg et al. ,"Evaluation of different doses of formoterol from a newly developed powder inhalation device in asthmatic patients," *Fundam. Clin. Pharmacol.*, 9:593–603 (1995).
Vianna et al., "Bronchodilators and Corticosteroids in the Treatment of Asthma," *Drugs of Today*, 34(3):203–223 (1998).
Wade et al, "Lecithin," In Handbook of Pharmaceutical Excipients, 2nd Edition, pp. 267–268, (1994).

Whelan et al., "Comparison of the Anti–Inflammatory Properties of Formoterol, Salbutamol, and Salmeterol in Guinea–Pig Skin and Lung," British Journal of Pharmacology, 110, pp. 613–618, (1993).
Wallin et al., "Time course and duration of bronchodilation with formoterol dry powder in patients with stable asthma," *Thorax*, 48:611–614 (1993).
Warne, "The discovery and clinical development of RPR 106541: an airway–selective steroid for the treatment of asthma," *Emerging Drugs*, 5(2):231–239 (2000).
Wilding et al., "Effect of long term treatment with salmeterol on asthma control: a double blind, randomized crossover study," *British Med. J.*, 314:1441–1446 (1997).
Woolcock et al., "Comparison of Addition of Salmeterol to Inhaled Steroids with Doubling of the Dose of Inhaled Steroids," *Am. J. Respir. Crit. Care Med.*, 153:1481–1488 (1996).
Yokoi et al. ,"The Development of a Radioimmunoassay for Formoterol," *Life Sciences*, 33:1665–1672 (1983).
Yoshida et al., "Acute, Subacute and Chronic toxicity Studies of a Bronchodilator, Formoterol Fumarate (BD 40)," *Oyo Yakuri*, 26(5), 811–29 (1983).
Docket Sheet dated Aug. 8, 2010 in *Dey v. Teva* in the United States District Court for the Northern District of West Virginia, Civil Action No. 1:09–cv–00087, Jun. 23, 2009.
Dey's Complaint in *Dey v. Teva* in the United States District Court for the Northern District of West Virginia, Civil Action No. 1:09–cv–00087.
Teva's Answer in *Dey v. Teva* in the United States District Court for the Northern District of West Virginia, Civil Action No. 1:09–cv–00087.
Teva's Invalidity Contentions in *Dey v. Teva* in the United States District Court for the Northern District of West Virginia, Civil Action No. 1:09–cv–00087.
Letter of May 12, 2009 from Teva Parenternal to Dey L.P.: Notice of ANA 91–141 Concerning Formoterol Fumarate Inhalation Solution, 0.02 mg/2 mL, With Paragraph IV Certification Concerning U.S. Patent Nos. 6,667,344, 6,814,953, 7,348,362 and 7,462,645 (Teva) [Teva Confidential—Filed Under Seal].
Teva Parenteral Medicines, Inc.'s Detailed Statement Of The Factual And Legal Bases For Its Opinion Letter of May 12, 2009 from Teva Parenternal to Dey L.P.: Notice of ANA 91–141 Concerning Formoterol Fumarate Inhalation Solution, 0.02 mg/2 mL, With Paragraph IV Certification Concerning U.S. Patent Nos. 6,667,344, 6,814,953, 7,348,362 and 7,462,645 (Teva) [Teva Confidential—Filed Under Seal].
Docket Sheet dated Aug. 8, 2010 in *Dey v. Sepracor* in the United States District Court for the Southern District of New York, Civil Action No. 1:07–cv–2353, Mar. 21, 2007.
Dey's Complaint in *Dey v. Sepracor* in the United States District Court for the Southern District of New York, Civil Action No. 1:07–cv–2353, Mar. 21, 2007 (Dey).
Sepracor's Answer and Counterclaims in the United States District Court for the Southern District of New York, Civil Action No. 1:07–cv–2353 (Sepracor).
Dey's Reply to Counterclaims and Additional Claim in the United States District Court for the Southern District of New York, Civil Action No. 1:07–cv–2353 (Dey).
Sepracor's Reply to Additional Claim in the United States District Court for the Southern District of New York, Civil Action No. 1:07–cv–2353 (Sepracor).

Sepracor's Second Amended Answer and Counterclaims in the United States District Court for the Southern District of New York, Civil Action No. 1:07–cv–2353, Jan. 23, 2009 (Sepracor) [Dey Confidential—Filed Under Seal].

Reply to Second Amended Answer and Counterclaims in the United States District Court for the Southern District of New York, Civil Action No. 1:07–cv–2353, Feb. 12, 2009 (Dey) [Dey Confidential—Filed Under Seal].

Supplemental Complaint in the United States District Court for the Southern District of New York, Civil Action No. 1:07–cv–2353, Mar. 30, 2009 (Dey).

Sepracor's Answer and Counterclaims to Dey's Supplemental Complaint in the United States District Court for the Southern District of New York, Civil Action No. 1:07–cv–2353, Apr. 10, 2009 (Sepracor) [Dey Confidential—Filed Under Seal].

Sepracor's Amended Answer and Counterclaims to Dey's Supplemental Complaint in the United States District Court for the Southern District of New York, Civil Action No. 1:07–cv–2353, Apr. 23, 2009 (Sepracor) [Dey Confidential—Filed Under Seal].

Dey's Reply to Sepracor's Amended Answer and Counterclaims to Dey's Supplemental Complaint in the United States District Court for the Southern District of New York, Civil Action No. 1:07–cv–2353, May 7, 2009 (Dey) [Dey Confidential—Filed Under Seal].

Mylan's Reply to Sepracor's Amended Answer and Counterlcaims to Dey's Supplemental Complaint in the United States District Court for the Southern District of New York, Civil Action No. 1:07–cv–2353, May 7, 2009 (Dey) [Dey Confidential—Filed Under Seal].

Second Supplemental Complaint in the United States District Court for the Southern District of New York, Civil Action No. 1:07–cv–2353, Jun. 4, 2009 (Dey).

Sepracor's Answer and Counterclaims to Dey's Second Supplemental Complaint in the United States District Court for the Southern District of New York, Civil Action No. 1:07–cv–2353, Jun. 18, 2008 (Sepracor) [Dey Confidential—Filed Under Seal].

Dey's Reply to Sepracor's Answer and Counterclaims to Dey's Second Supplemental Complaint in the United States District Court for the Southern District of New York, Civil Action No. 1:07–cv–2353, Jul. 8, 2009 (Dey) [Dey Confidential—Filed Under Seal].

Mylan's Reply to Sepracor's Answer and Counterclaims to Dey's Second Supplemental Complaint in the United States District Court for the Southern District of New York, Civil Action No. 1:07–cv–2353, Jul. 8, 2009 (Dey) [Dey Confidential—Filed Under Seal].

Dey's Supplemental Objections and Responses to Sepracor's First Set of Interrogatories to Dey in the United States District Court for the Southern District of New York, Civil Action No. 1:07–cv–2353 (Dey) [Dey Confidential—Filed Under Seal].

Dey's Objections and Responses to Sepracor's First Set of Interrogatories in the United States District Court for the Southern District of New York, Civil Action No. 1:07–cv–2353 (Dey) [Dey Confidential—Filed Under Seal].

Dey and Mylan's Objections and Responses to Sepracor's Third Set of Interrogatories in the United States District Court for the Southern District of New York, Civil Action No. 1:07–cv–2353, (Dey) [Dey Confidential—Filed Under Seal].

Opening Expert Report of Peter Byron, Sep. 25, 2009 (Sepracor) [Dey Confidential—Filed Under Seal] [Sepracor Confidential—Redacted] [Ok].

Opening Expert Report of Peter Byron Exhibit 1: Curriculum Vitae of Peter Byron (Sepracor).

Opening Expert Report of Peter Byron Exhibit 2: List of Documents Considered (Sepracor).

Opening Expert Report of Peter Byron Exhibit 3: U.S. Patent No. 6,667,344 (currently under reexamination, Control No. 90/010,488) (provided as Document A129).

Opening Expert Report of Peter Byron Exhibit 4: U.S. Patent No. 6,814,953 (currently under reexamination, Control No. 90/010,489) (provided as Document A133).

Opening Expert Report of Peter Byron Exhibit 5: U.S. Patent No. 7,348,362 (provided as Document A136).

Opening Expert Report of Peter Byron Exhibit 6: U.S. Patent No. 7,462,645 (provided as Document A137).

Opening Expert Report of Peter Byron Exhibit 7: U.S. Patent No. 7,465,756 (provided as Document A138).

Opening Expert Report of Peter Byron Exhibit 8: U.S. Patent No. 7,473,710 (provided as Document A139).

Opening Expert Report of Peter Byron Exhibit 9: U.S. Patent No. 7,541,385 (provided as Document A140).

Opening Expert Report of Peter Byron Exhibit 10: U.S. Patent No. 3,994,974 (provided as Document A23).

Opening Expert Report of Peter Byron Exhibit 11: *Aerosols in Medicine: Principles, Diagnosis and Therapy.* (ed. by Moren, F., Dolovich, M.B., Newhouse, M.T. and Newman, S.P., Second, revised edition, pp. 340–350 1993).

Opening Expert Report of Peter Byron Exhibit 12: Byron, P.R., *Aerosol Formulation, Generation, and Delivery Using Nonmetered Systems.,* Respiratory Drug Delivery, Ch. 6, pp. 143–165.

Opening Expert Report of Peter Byron Exhibit 13: *Pharmaceutical Inhalation Aerosol Technology.* (ed. by Hickey, A.J.)., 54: 166–167 (1992).

Opening Expert Report of Peter Byron Exhibit 14: *Physical Pharmacy: Physical Chemical Principles in the Pharmaceutical Sciences.* (ed. by Martin, A.), Fourth edition, pp. 147, 178–186, 284–317 (1993).

Opening Expert Report of Peter Byron Exhibit 15: Pharmaceutical Development Report for Formoterol Fumarate Inhalation Solution 20 mcg/2 mL (Sepracor) [Dey Confidential—Filed Under Seal].

Opening Expert Report of Peter Byron Exhibit 16: PCT Publication WO 01/39745 (provided as Document B59).

Opening Expert Report of Peter Byron Exhibit 17: U.S. Patent No. 6,667,344 (provided as Document A129).

Opening Expert Report of Peter Byron Exhibit 18: Response to Office Action, dated Apr. 22, 2003 in U.S. Appl. No. 09/887,281.

Opening Expert Report of Peter Byron Exhibit 19: Summary of Formoterol work done by M. Joyce (Sepracor) [Dey Confidential—Filed Under Seal].

Opening Expert Report of Peter Byron Exhibit 20: U.S. Patent No. 6,150,418 (provided as Document A93).

Opening Expert Report of Peter Byron Exhibit 21: Lachman, L., et al., *The Theory and Practice of Industrial Pharmacy.* (Third edition, pp. 176, 191–193, 761–770)(1986).

Opening Expert Report of Peter Byron Exhibit 22: Summary of Formoterol Unit Dose Formulation Development (Sepracor) [Dey Confidential—Filed Under Seal].

Opening Expert Report of Peter Byron Exhibit 23: First Banerjee Deposition Transcript, Feb. 13, 2009 (Sepracor) [Dey Confidential—Filed Under Seal].

Opening Expert Report of Peter Byron Exhibit 24: Oral Inhalation PDT Meeting Minutes Nov. 9, 2000 (Sepracor) [Dey Confidential—Filed Under Seal].

Opening Expert Report of Peter Byron Exhibit 25: U.S. Patent No. 6,161,536 (provided as Document A95).

Opening Expert Report of Peter Byron Exhibit 26: Effect Of Surfactants And Cosolvents On Formoterol Stability (Sepracor) [Dey Confidential—Filed Under Seal].

Opening Expert Report of Peter Byron Exhibit 27: A Comparative Stability Study Of Formoterol In Active Substance Concentrate (U.S. Patent #6,150,418) And Dey's Formoterol Fumarate Inhalation Solutions (Sepracor) [Dey Confidential—Filed Under Seal].

Opening Expert Report of Peter Byron Exhibit 28: Akapo Deposition Transcript, Dec. 10, 2008 (Sepracor) [Dey Confidential—Filed Under Seal].

Opening Expert Report of Peter Byron Exhibit 29: Letter of May 12, 2009 from Teva Parenternal to Dey L.P.: Notice of ANA 91–141 Concerning Formoterol Fumarate Inhalation Solution, 0.02 mg/2 mL, With Paragraph IV Certification Concerning U.S. Patent Nos. 6,667,344, 6,814,953, 7,348,362 and 7,462,645 (Teva) [Teva Confidential—Filed Under Seal].

Opening Expert Report of Peter Byron Exhibit 30: Ionic Strength Calculations (Sepracor) [Sepracor Confidential—Redacted].

Opening Expert Report of Peter Byron Exhibit 31: Formoterol: Merck Index (Twelfth Edition, p. 4273) (1996).

Opening Expert Report of Peter Byron Exhibit 32: Canadian Patent No. 2,257,329.

Opening Expert Report of Peter Byron Exhibit 33: PCT Publication WO 95/31964 (provided as Document B14).

Opening Expert Report of Peter Byron Exhibit 34: Maesen, FP., et al., *Formoterol suspension aerosol. Comparison with formoterol solution aerosol for 12 weeks in asthmatic patients.* Chest 102:1544–1549 (1992) (provided as Document C45).

Opening Expert Report of Peter Byron Exhibit 35: Pham Deposition Transcript, Sep. 9, 2000 (Sepracor) [Dey Confidential—Filed Under Seal].

Opening Expert Report of Peter Byron Exhibit 36: Formoterol Unit Dose Preliminary Results and Formulation Plan. (Sepracor) [Dey Confidential—Filed Under Seal].

Opening Expert Report of Peter Byron Exhibit 37: Vodas, E.B., *Stability of Pharmaceutical Products.* (Remington Nineteenth Edition, vol. 1) Ch. 38, pp. 639–647 (1995).

Opening Expert Report of Peter Byron Exhibit 38: U.S. Appl. No. 60/061,363.

Opening Expert Report of Peter Byron Exhibit 39: Decision on Petition dated Oct. 8, 2002 in U.S. Appl. No. 09/887,281.

Opening Expert Report of Peter Byron Exhibit 40: Table Comparing the Claims of the '344 patent to the prior art, for Obviousness (Sepracor).

Opening Expert Report of Peter Byron Exhibit 41: Table Comparing the Claims of the '953 patent to the prior art, for Obviousness (Sepracor).

Opening Expert Report of Peter Byron Exhibit 42: Table Comparing the Claims of the '362 patent to the prior art, for Obviousness (Sepracor).

Opening Expert Report of Peter Byron Exhibit 43: Table Comparing the Claims of the '385 patent to the prior art, for Obviousness (Sepracor).

Opening Expert Report of Peter Byron Exhibit 44: Table Comparing the Claims of the '645 patent to the prior art, for Obviousness (Sepracor).

Opening Expert Report of Peter Byron Exhibit 45: Table Comparing the Claims of the '710 patent to the prior art, for Obviousness (Sepracor).

Opening Expert Report of Peter Byron Exhibit 46: Table Comparing the Claims of the '756 patent to the prior art, for Obviousness (Sepracor).

Opening Expert Report of Peter Byron Exhibit 47: Rosenborg, J., et al., *Mass Balance and Metabolism of [$^3H$] Formoterol in Healthy Men After Combined I.V. and Oral Administration Mimicking Inhalation.* Drug Metabolism and Disposition 27(10): 1104–1116 (1999).

Opening Expert Report of Peter Byron Exhibit 48: Formoterol Fumarate Formulation Activities (Sepracor) [Dey Confidential—Filed Under Seal].

Opening Expert Report of Peter Byron Exhibit 49: (Sepracor) [Dey Confidential—Filed Under Seal] Missing Still Need Document.

Opening Expert Report of Peter Byron Exhibit 50: Laskar Deposition Transcript, Sep. 11, 2008 (Sepracor) [Dey Confidential—Filed Under Seal].

Opening Expert Report of Peter Byron Exhibit 51: (Sepracor) [Sepracor Confidential—Copy Not Available].

Opening Expert Report of Peter Byron Exhibit 52: (Sepracor) [Sepracor Confidential—Copy Not Available].

Opening Expert Report of Peter Byron Exhibit 80: Dey's Supplemental Objections and Responses to Sepracor's First Set of Interrogatories to Dey. (Sepracor) [Dey Confidential—Filed Under Seal].

Opening Expert Report of Peter Byron Exhibit 91: Dey's and Mylan's Objections and Responses to Sepracor's Third Set of Interrogatories. (Sepracor) [Dey Confidential—Filed Under Seal].

Opening Expert Report of Peter Byron Exhibit 97: Second Chaudry Deposition Transcript, Jul. 1, 2009. (Sepracor) [Dey Confidential—Filed Under Seal].

Opening Expert Report of Peter Byron Exhibit 98: Formoterol, Formoterol Concentrate, and Formoterol Low Volume Pls (also cited as Document D__(Carpenter Exh 114) (Sepracor) [Dey Confidential—Filed Under Seal].

Opening Expert Report of Peter Byron Exhibit 99: Declaration of P. Banerjee dated Sep 24, 2004 submitted in U.S Appl. No. 09/887,496.

Rebuttal Expert Report of Peter Byron, Oct. 23, 2009 (Sepracor) [Dey Confidential—Filed Under Seal] [Sepracor Confidential—Redacted].

Rebuttal Expert Report of Peter Byron Exhibit 100: Amendment After Final dated Apr. 22, 2003, submitted in U.S. Appl. No. 09/887,281.

Rebuttal Expert Report of Peter Byron Exhibit 101: Notice of Allowance.

Rebuttal Expert Report of Peter Byron Exhibit 102: Akapo Deposition Transcript, Dec. 10, 2008 (Sepracor) [Dey Confidential—Filed Under Seal].

Rebuttal Expert Report of Peter Byron Exhibit 103: Laskar Deposition Transcript, Sep. 11, 2008 (Sepracor) [Dey Confidential—Filed Under Seal].

Rebuttal Expert Report of Peter Byron Exhibit 104: Second Chaudry Deposition Transcript, Ju. 1, 2009 (Sepracor) [Dey Confidential—Filed Under Seal].

Rebuttal Expert Report of Peter Byron Exhibit 105: United States Pharmacopeia, pp. 2–14 (1999).

Reply Expert Report of Peter Byron Nov. 20, 2009 (Sepracor) [Dey Confidential—Filed Under Seal] [Sepracor Condifential—Redacted].

Reply Expert Report of Peter Byron Exhibit 107: Cohen, S.P., et al., *Nebulized Morphine as a Treatment for Dyspnea in a Child with Cystic Fibrosis.* Pediatrics, 2002; vol. 110, No. 3, Sep. 2002.

Reply Expert Report of Peter Byron Exhibit 108: Foral, P.A., et al., *Nebulized Opioids Use in COPD.* Chest 125:691–694 (2004).

Reply Expert Report of Peter Byron Exhibit 109: Second Chaudry Deposition Transcript, Jul. 1, 2009 (Sepracor) [Dey Confident—Filed Under Seal].

Reply Expert Report of Peter Byron Exhibit 110: Laskar Deposition Transcript, Sep. 11, 2008 (Sepracor) [Dey Confident—Filed Under Seal].

Reply Expert Report of Peter Byron Exhibit 111: Amendment dated Mar. 23, 2007 submitted in U.S. Appl. No. 10/887,785.

Reply Expert Report of Peter Byron Exhibit 112: Rieger Deposition Transcript, Aug. 19, 2009 (Sepracor) [Dey Confident—Filed Under Seal].

Reply Expert Report of Peter Byron Exhibit 113: Fluorouracil® Package Insert.

Reply Expert Report of Peter Byron Exhibit 114: Buffered Pfizerpen® Instructions.

Reply Expert Report of Peter Byron Exhibit 115: Interoffice Memo from G. Michaud to M. Engle, Apr. 4, 2002 (Sepracor) [Dey Confident—Filed Under Seal].

Reply Expert Report of Peter Byron Exhibit 118: Akapo Deposition Transcript, Dec. 10, 2008 (Sepracor) [Dey Confident—Filed Under Seal].

Opening Expert Report of Peter Byron—noted in Exhibit 2: Handbook of Pharmaceutical Excipients, 3rd Ed., (ed. Kibbe, A.H.), "Citric Acid Monohydrate," pp. 140–142 (2000) (provided as document C43) (copy not available—will supply in Supplemental IDS).

Expert Report of Dr. Gene Colice, Nov. 20, 2009 (Dey).

Expert Report of Dr. Gene Colice Exhibit 1: Curriculum Vitae for Dr. Gene Colice (Dey).

Expert Report of Dr. Gene Colice Exhibit 2: Testifying Case List for Dr. Gene Colice (Dey).

Expert Report of Dr. Gene Colice Exhibit 3: List of Documents Considered (Dey).

Expert Report of Dr. Gene Colice Exhibit 4: Global Strategy for Diagnosis, Management, and Prevention of Chronic Obstructive Pulmonary Disease—Update 2008.

Expert Report of Dr. Gene Colice Exhibit 5: Dolovich et. al., *Device Selection and Outcomes of Aerosol Therapy: Evidence–Based Guidelines.* Chest 2005; 127; 335–371.

Expert Report of Dr. Gene Colice Exhibit 6: Nebulizers—Perforomist and Brovana—Coverage Criteria and Billing Instructions. TriCenturion Bulletin, Aug. 2007.

Expert Report of Hon. Gerald Mossinghoff, Oct. 23, 2009 (Dey) [Dey Confidential—Filed Under Seal].

Expert Report of Hon. Gerald Mossinghoff Exhibit A: Curriculum Vitae for Hon. Gerald Mossinghoff (Dey).

Expert Report of Hon. Gerald Mossinghoff Exhibit B: Publications of Hon. Gerald Mossinghoff (Dey).

Expert Report of Hon. Gerald Mossinghoff Exhibit C: The Hon. Gerald Mossinghoff Appeared as a Principal Witness in the Following Congressional Hearings (Dey).

Expert Report of Hon. Gerald Mossinghoff Exhibit D: Patent Cases in which the Hon. Gerald Mossinghoff Testified as an Expert Witness in Court or in a Deposition (Dey).

Expert Report of Hon. Gerald Mossinghoff Exhibit E: List of Documents Considered (Dey).

Expert Report of Hon. Gerald Mossinghoff—noted in Exhibit E: Letter from Jeffery Alan Hovden to David M. Conca, Jul. 22, 2008.

Rebuttal Expert Report of Lehrman, Oct. 22, 2009 [Sepracor Confidential—Redacted] [Dey Confidential—Filed Under Seal].

Rebuttal Expert Report of Lehrman Exhibit 1: List of Documents Considered.

Rebuttal Expert Report of Lehrman Exhibit 2: Maesen, F.P.V., et al., *Formoterol Suspension Aerosol Comparison with Formoterol Solution Aerosol for 12 Weeks in Asthmatic Patients.* Chest 102:1544–1549 (1992) (provided as Document C45).

Rebuttal Expert Report of Lehrman Exhibit 3: U.S. Patent No. 6,150,418 (provided as Document A93).

Rebuttal Expert Report of Lehrman Exhibit 4: A Comparative Stability Study Of Formoterol In Active Substance Concentrate (US Patent #6,150,418 [to Hochrainer et al.])and Dey's Formoterol Fumarate Inhalation Solutions Oct. 10, 2005 [Dey Confidential—Filed Under Seal].

Rebuttal Expert Report of Lehrman Exhibit 5: Declaration of P. Banerjee dated Sep. 24, 2004 submitted in U.S. Appl. No. 09/887,496 (Dey).

Rebuttal Expert Report of Lehrman Exhibit 6: U.S. Patent No. 3,994,974 (provided as Document A23).

Rebuttal Expert Report of Lehrman Exhibit 7: U.S. Patent No. 6,040,344 (provided as Document A85).

Rebuttal Expert Report of Lehrman Exhibit 8: Guidance for Industry: Analytical Procedures and Methods Validation—Draft Guidance, Aug. 2000.

Rebuttal Expert Report of Lehrman Exhibit 9: NDA Analytical Procedures (Formoterol Fumarate Inhalation Solution, 20 mcg/2 mL (Dey) [Dey Confidential—Filed Under Seal].

Rebuttal Expert Report of Lehrman Exhibit 12: Foradil®.

Rebuttal Expert Report of Lehrman Exhibit 13: European Patent No. 1 157 689 (provided as Document B7).

Rebuttal Expert Report of Lehrman Exhibit 14: Formoterol Inhalation Unit Dose (Dey) [Dey Confidential—Filed Under Seal].

Expert Report of Robert Kuhn, Oct. 23, 2009 (Dey) Expert Report Not Under Seal? FLH Marks as Public?. See D164.

Expert Report of Robert Kuhn Exhibit 1: U.S. Patent No. 3,994,974 (provided as Document A23).

Expert Report of Robert Kuhn Exhibit 2: Curriculum Vitae for Robert Kuhn (Dey).

Expert Report of Robert Kuhn Exhibit 3: List of Materials Reviewed (Dey).

Expert Report of Robert Kuhn Exhibit 4: Kuhn, R., *Formulation of Aerosolized Therapeutics* Chest 120 (2001) 94S–98S.

Expert Report of Robert Kuhn Exhibit 5: Guhan et al., *Systemic effects of formoterol and salmeterol: a dose–response comparison in healthy subjects.* Thorax 55 (2000) 650–656.

Expert Report of Robert Kuhn Exhibit 6: Kuhn, R., *Pharmaceutical Considerations in Aerosol Drug Delivery* Pharacotherapy 22 (2002) 80S–85S.

Expert Report of Robert Kuhn Exhibit 7: Walsh, *Pharmaceutical Biotechnology: Concepts and Applications*, John Wiley & Sons, Ltd., West Sussex, England, 2007, p. 72.
Expert Report of Robert Kuhn Exhibit 8: Hickey, A.J., *Pharmaceutical Inhalation Aerosol Technology*, Marcel Dekker Inc., New York, Ed. 2, 2004, p. 282.
Expert Report of Robert Kuhn Exhibit 9: FDA CDER Transcript, Meeting of Pharmacy Compounding Advisory Committee, Sep. 14, 1998, p. 136–139.
Expert Report of Robert Kuhn Exhibit 10: Molema et al., *Drug Targeting Organ–Specific Strategies*, Wiley–VCH, New York, 2001, p. 67.
Expert Report of Robert Kuhn Exhibit 11: Ganderton et al., *Drug Delivery to the Respiratory Tract*, Ells Horwood Ldt., Chichester, England, 1987, p. 128.
Expert Report of Robert Kuhn Exhibit 12: Garg et al., *Insulin Delivery via Lungs–Is It Still Possible?* Diabetes Technology & Therapeutics 11, Suppl. 2 (2009) S–I.
Opening Expert Report of Larry Nixon, Sep. 25, 2009— (Sepracor) [Dey Confidential—Filed Under Seal].
Opening Expert Report of Larry Nixon Exhibit 1: Documents Considered.
Opening Expert Report of Larry Nixon Exhibit 2: Curriculum Vitae for Larry Nixon.
Reply Expert Report of Larry Nixon, Nov. 20, 2009 (Sepracor) [Dey Confidential—Filed Under Seal].
Reply Expert Report of Larry Nixon Exhibit 1: United States Patent and Trademark Office Utility, Plant, and Reissue Examiner Staffing FY 2009.
Reply Expert Report of Larry Nixon Exhibit 2: List of Documents Considered.
Reply Expert Report of Larry Nixon Exhibit 3: United States Patent and Trademark Office Performance and Accountability Report FY 2009.
Opening Expert Report of Dr. Philip Marcus, Oct. 23, 2009 (Sepracor).
Opening Expert Report of Dr. Philip Marcus Exhibit 1: Curriculum Vitae for Dr. Philip Marcus.
Opening Expert Report of Dr. Philip Marcus Exhibit 2: Cases Testified in over the last Four Years.
Opening Expert Report of Dr. Philip Marcus Exhibit 3: List of Documents Considered.
Opening Expert Report of Dr. Philip Marcus Document Reviewed: Dolovich, M.B., et al., *Device Selection and Outcomes of Aerosol Therapy: Evidence–Based Guidelines*. Chest 127:335–371 (2005).
Opening Expert Report of Dr. Philip Marcus Document Reviewed: Global Strategy for Diagnosis, Management, and Prevention of Chronic Obstructive Pulmonary Disease— Updated 2008.
Opening Expert Report of Dr. Philip Marcus Document Reviewed: Standards for the Diagnosis and Management of Patients with COPD (2004).
Reply Expert Report of Dr. Philip Marcus, Nov. 20, 2009.
Reply Expert Report of Dr. Philip Marcus Exhibit 1: List of Documents Considered.
Supplemental Expert Report of Dr. Gordon Rausser, PhD, Oct. 22, 2009 (Dey) [Dey Confidential—Filed Under Seal].
Supplemental Expert Report of Dr. Gordon Rausser Exhibit A: Four Year Testimony List of Gordon Rausser (Dey).
Supplemental Expert Report of Dr. Gordon Rausser Exhibit B: Additional Materials Reviewed and Relied On (Dey).
Supplemental Expert Report of Dr. Gordon Rausser Cited in Report: Label for Perforomist.

Supplemental Expert Report of Dr. Gordon Rausser Cited in Report: Label for Brovana.
Supplemental Expert Report of Dr. Gordon Rausser Cited in Report: Grove, C., *Availability of Xopenex and Brovana for Medicare Patients*, Associated Content, Sep. 17, 2007, www.associatedcontent.com/article/372751/availability_of_xopenex_and-_brovana.html?cat=71 (last visited Jul. 26, 2010).
Supplemental Expert Report of Dr. Gordon Rausser Cited in Report: Medpac, Report to the Congress. *Variation and innovation in Medicare. Chapter 9: Medicare payments for outpatient drugs under Part B*, Jun. 2003, pp. 149–170.
Supplemental Expert Report of Dr. Gordon Rausser Cited in Report: NHIC Corp., *Nebulizers—Brovana and Perforomist – instructions for–new HCPCS codes: Apr. 17, 2008*, www.medicarenhic.com/dme/medical_review/mr_bulletins/mr_bulletin_current/041708_neb.pdf (last visited Jul 26, 2010).
Supplemental Expert Report of Dr. Gordon Rausser Cited in Report: Sepracor, Aug. 9, 2007, 10–Q filing for the quarter ending Jun. 30, 2007.
Supplemental Expert Report of Dr. Gordon Rausser Cited in Report: American Association for Respiratory Care, *AARC Seeks Clarification on Brovana Reimbursement*, Apr. 26, 2007. www.aarc.org/headlines/07/04/brovana/ (last visited Jul. 26, 2010).
Supplemental Expert Report of Dr. Gordon Rausser Cited in Report: Spiller, L.D. and W.W. Wymer, *Physicians' Perceptions and Uses of Commerical Drug Information Sources: An Examination of Pharmaceutical Marketing to Physicians*, Health Marketing Quarterly 19.1, pp. 91–106. (2001).
Supplemental Expert Report of Dr. Gordon Rausser Cited in Report: Narayanan, S., et al., *Temporal Differences in the Role of Marketing Communication in New Product Categories*, Journal of Marketing Research 42 (Aug. 2005) pp. 278–290.
Supplemental Expert Report of Dr. Gordon Rausser Cited in Report: Navarro, R.P. *Pharmacy & Therapeutics Committees in managed care organizations*, in Robert P. Navarro, ed., Managed Care Pharmacy Practice, Sudbury, Mass.: Jones and Bartlett Publishers, pp. 323–340.
Supplemental Expert Report of Dr. Gordon Rausser Cited in Report: Berndt, E.R., et al., *The roles of marketing, product quality and price competition in the growth and composition of the US antiulcer drug industry*, in The Economics of New Goods, ed. Timothy Bresnahan and Robert J. Gordon (Chicago: University of Chicago Press, 1997).
Supplemental Expert Report of Dr. Gordon Rausser Cited in Report: Rosenthal, M.B., et al., *Demand Effects of Recent Changes in Prescription Drug Promotion*, Kaiser Family Foundation, Jun. 2003.
Expert Report of Carlos Schuler, Oct. 23, 2009 (Dey).
Expert Report of Carlos Schuler Exhibit 1: Curriculum Vitae for Carlos Schuler (Dey).
Expert Report of Carlos Schuler Exhibit 2: List of Documents Considered (Dey).
Expert Report of Carlos Schuler Exhibit 3: Brovana® labeling and Medication Guide.
Expert Report of Carlos Schuler Exhibit 4: Perforomist® labeling and Medication Guide.
Expert Report of Carlos Schuler Exhibit 5: Foradil® labeling.
Expert Report of Carlos Schuler Exhibit 6: U.S. Patent No. 6,150,418 (provided as Document A93).

Expert Report of Carlos Schuler Exhibit 7: Dalby, R.; Spallek, M.; Vashaar, T., *A Review of the Development of Respimat® Soft Mist™ Inhaler,* International Journal of Pharmaceutics 283 (2004) 1–9.

Expert Report of Carlos Schuler Exhibit 8: Respimat® promotional materials (located at http://www.respimat.com/com/homepage.jsp), last visited Jul. 15, 2010.

Expert Report of Carlos Schuler Exhibit 9: Pari Nebulizer.

Expert Report of Carlos Schuler Exhibit 10: Spiriva® User Guide.

Expert Report of Carlos Schuler Exhibit 11: PCT Publication W091/14468.

Expert Report of Carlos Schuler Exhibit 12: PCT Publication W097/12687.

Expert Report of Carlos Schuler Exhibit 13: U.S. Patent No. 7,571,722.

Expert Report of Carlos Schuler Exhibit 14: Zierenberg, et al., *Boehringer Ingelheim Nebulizer Binebo® A New Approach to Inhalation Therapy.* Respiratory Drug Delivery V, 1996 (p. 187–193).

Expert Report of Carlos Schuler Exhibit 15: PCT Publication W097/39831.

Expert Report of Carlos Schuler Exhibit 16: German Patent Publication DE 198 47 968.

Expert Report of Carlos Schuler Exhibit 17: US Patent No. 6,481,435 (provided as Document A125).

Expert Report of Carlos Schuler Exhibit 18: Spallek, M.W., et al., *Scale–Up And Production Challenges Of Bringing Respimat® Soft Mist™ Inhaler (SMI) To Market* Respiratory Drug Delivery IX, 2004 (p. 263–270).

Expert Report of Carlos Schuler Exhibit 19: Clark et al., *Formulation of Proteins for Pulmonary Delivery.* Protein Formulation and Delivery Second Edition (Drugs and the Pharmaceutical Sciences), p. 219–253.

Expert Report of Carlos Schuler Exhibit 20: Kunkel, G. et al., *Respimat® (a New Soft Mist Inhaler) Delivering Fenoterol plus Ipratropium Bromide Provides Equivalent Bronchodilation at Half the Cumulative Dose Compared with a Conventional Metered Dose Inhaler in Asthmatic Patients.* Respiration 2000;67:306–314.

Expert Report of Carlos Schuler Exhibit 21: Ganderton, D., *Targeted delivery of inhaled drugs: current challenges and future goals.* J Aerosol Med., 12 (suppl. 1), pp. 3–8 (1999).

Expert Report of Carlos Schuler Exhibit 22: Goldberg et al., *Improved delivery of fenoterol plus ipratropium bromide using Respimat® compared with a conventional metered dose inhaler.* Eur Respir J. 2001; 17: 225–232.

Expert Report of Carlos Schuler Exhibit 23: Vincken et al., *Fenoterol Delivery by Respimat® Soft Mist Inhaler Versus CFC Metered Dose Inhaler: Cumulative Dose–Response Study in Asthma Patients.* Journal of Asthma, vol. 40, No. 6 pp. 721–730 (2003).

Expert Report of Carlos Schuler Exhibit 24: Vincken et al., *Long–Term Efficacy and Safety of Ipratropium Bromide plus Fenoterol via Respimat® Soft Mist™ Inhaler (SMI) versus a Pressurized Metered–Dose–Inhaler in Asthma.* Clin. Drug. Invest. 2004:24 (1): 17–28.

Expert Report of Carlos Schuler Exhibit 25: Hochrainer et al., *Comparison of the Aerosol Velocity and Spray Duration of Respimat® Soft Mist™ Inhaler and Pressurized Metered Dose Inhalers.* J. Aerosol Medicine 2005, vol. 18, No. 3, pp. 273–282.

Opening Expert Report of Robert Williams III, Sep. 25, 2009.

Opening Expert Report of Robert Williams III Exhibit 1: Curriculum Vitae for Robert Williams III.

Opening Expert Report of Robert Williams III Exhibit 2: U.S. Patent No. 3,994,974 (provided as Document A23).

Opening Expert Report of Robert Williams III Exhibit 3: U.S. Patent No. 6,040,344 (provided as Document A85).

Opening Expert Report of Robert Williams III Exhibit 4: Byron, P.R., *Aerosol Formulation, Generation, and Delivery Using Nonmetered Systems.,* Respiratory Drug Delivery, Ch. 6, pp. 143–165.

Opening Expert Report of Robert Williams III Exhibit 5: "Sodium Hydroxide," The Merck Index, 12thEd., pp. 8772–8773 (1996).

Opening Expert Report of Robert Williams III Exhibit 6: : *Aerosols in Medicine: Principles, Diagnosis and Therapy.* (ed. by Moren, F., Dolovich, M.B., Newhouse, M.T. and Newman, S.P., Second, revised edition, pp. 340–350 1993).

Opening Expert Report of Robert Williams III Exhibit 7: Stoklosa, M.J. et al., *Pharmaceutical Calculations,* 7th Ed., pp. 196–197 (1980).

Opening Expert Report of Robert Williams III Exhibit 8: *Handbook of Pharmaceutical Excipients,* 3rd Ed., (ed. Kibbe, A.H.), "Citric Acid Monohydrate," pp. 140–142 (2000).

Opening Expert Report of Robert Williams III Exhibit 9: *Pharmaceutical Inhalation Aerosol Technology.* (ed. by Hickey, A.J.)., 54: 166–167 (1992).

Opening Expert Report of Robert Williams III Exhibit 10: Formoterol Fumarate Inhalation Solution 20 mcg/2mL Pharmaceutical Development Report (Sepracor) [Dey Confidential—Filed Under Seal].

Opening Expert Report of Robert Williams III Exhibit 11: Formoterol Fumarare Inhalation Solution 20 mcg/2mL Analytical Procedures (Sepracor) [Dey Confidential—Filed Under Seal].

Opening Expert Report of Robert Williams III Exhibit 13: GAO Arformoterol Tartrate and Murakami Fumarate Tables.

Opening Expert Report of Robert Williams III Exhibit 14: GAO Arformoterol Tartrate and Murakami Fumarate Tables.

Opening Expert Report of Robert Williams III Exhibit 15: Study Report Dey Formoterol Fumarare vs. U.S. Patent 6,150,418 (Sepracor) [Dey Confidential—Filed Under Seal].

Opening Expert Report of Robert Williams III Exhibit 16: Lab Notebook (Sepracor) [Dey Confidential—Filed Under Seal].

Opening Expert Report of Robert Williams III Exhibit 17: Lab Notebook (Sepracor) [Dey Confidential—Filed Under Seal].

Opening Expert Report of Robert Williams III Exhibit 18: Stability Data of Formoterol Low Drug Concentration (Sepracor) [Dey Confidential—Filed Under Seal].

Opening Expert Report of Robert Williams III Exhibit 19: Lab Notebook (Sepracor) [Dey Confidential—Filed Under Seal].

Opening Expert Report of Robert Williams III Exhibit 20: Effect of pH on Degradation of Formoterol (Sepracor) [Dey Confidential—Filed Under Seal].

Opening Expert Report of Robert Williams III Exhibit 21: Lab Notebook (Sepracor) [Dey Confidential—Filed Under Seal].

Opening Expert Report of Robert Williams III Exhibit 22: Lab Notebook (Sepracor) [Dey Confidential—Filed Under Seal].

Opening Expert Report of Robert Williams III Exhibit 23: Data for Formoterol High Dose (Sepracor) [Dey Confidential—Filed Under Seal].

Opening Expert Report of Robert Williams III Exhibit 24: Stability Study for Formoterol Fumarare Inhalation Solution 20 mcg/2mL (Sepracor) [Dey Confidential—Filed Under Seal].

Opening Expert Report of Robert Williams III Exhibit 37: Formulation Comparison (Sepracor) [Dey Confidential—Filed Under Seal].

Opening Expert Report of Robert Williams III Exhibit 38: Formulation Comparison (Sepracor) [Dey Confidential—Filed Under Seal].

Opening Expert Report of Robert Williams III Exhibit 39: [Sepracor Confidential—Copy Not Available].

Opening Expert Report of Robert Williams III Exhibit 40: Declaration of P. Banerjee dated Sep. 24, 2004 submitted in U.S. Appl. 09/887,496 (Dey).

Opening Expert Report of Robert Williams III Exhibit 41: Table Supporting Declaration of P. Banerjee dated Sep. 24, 2004 submitted in U.S. Appl. No. 09/887,496 (Dey).

Opening Expert Report of Robert Williams III Exhibit 42: Listing of Documents Reviewed.

Opening Expert Report of Robert Williams III Exhibit 43: Lab Notebook [Dey Confidential—Filed Under Seal].

Opening Expert Report of Robert Williams III Exhibit 44: Lab Notebook [Dey Confidential—Filed Under Seal].

Opening Expert Report of Robert Williams III Exhibit 45: Method Qualification Results (Murakami and Gao) (Dey).

Expert Report of Robert Williams III, Nov. 20, 2009 [Dey Confidential—Filed Under Seal] [Sepracor Confidential—Redacted].

Reply Expert Report of Robert Williams III Exhibit 46: Method Validation Report for HPLC Assay of Formoterol Fumarate and its Related Substances in Formoterol Fumarate Inhalation Solution, 20 mcg/2mL (ATM–716–13) (Sepracor) [Dey Confidential—Filed Under Seal].

Reply Expert Report of Robert Williams III Exhibit 50: Study table (Sepracor) [Dey Confidential—Filed Under Seal].

Reply Expert Report of Robert Williams III Exhibit 51: Formoterol Fumarate Inhalation Solution, 20 mcg/2 mL (Sepracor) [Dey Confidential—Filed Under Seal].

Reply Expert Report of Robert Williams III Exhibit 52: U.S. Patent No. 6,150,418 (provided as Document A93).

Reply Expert Report of Robert Williams III Exhibit 55: Listing of Additional Documents Reviewed.

Akapo Deposition Transcript, Dec. 10, 2008 (Dey) [Dey Confidential—Filed Under Seal].

Akapo Deposition Exhibit 51: Personal Action Form (Dey) [Dey Confidential—Filed Under Seal].

Akapo Deposition Exhibit 52: Employee Self Appraisal (Dey) [Dey Confidential—Filed Under Seal].

Akapo Deposition Exhibit 53: U.S. Appl. No. 60/284,606.

Akapo Deposition Exhibit 54: U.S. Patent No. 6,667,344 w/Partial File History.

Akapo Deposition Exhibit 55: U.S. Patent No. 6,814,953 w/Partial File History.

Akapo Deposition Exhibit 56: U.S. Patent No. 7,348,362 w/Partial File History.

Akapo Deposition Exhibit 57: United States Code, Title 18, §§ 1001 to 1200.

Akapo Deposition Exhibit 58: S. Akapo Award for the Perforomist Patents (Dey) [Dey Confidential—Filed Under Seal].

Akapo Deposition Exhibit 59: A Comparative Stability Study Of Formoterol In Active Substance Concentrate (US Patent #6,150,418) and Dey's Formoterol Fumarate Inhalation Solutions (Dey) [Dey Confidential—Filed Under Seal].

Akapo Deposition Exhibit 60: U.S. Patent No. 6,150,418 (provided as Document A93).

Akapo Deposition Exhibit 61: Summary of Formoterol work done by M. Joyce (Dey) [Dey Confidential—Filed Under Seal].

Akapo Deposition Exhibit 62: Summary of Stability Study for Formoterol Fumarate Inhalation Placebo (Dey) [Dey Confidential—Filed Under Seal].

Akapo Deposition Exhibit 63: A stability–indicating HPLC assay method for formoterol and its related substances in formoterol fumarate dihydrate drug substance (Dey) [Dey Confidential—Filed Under Seal].

Akapo Deposition Exhibit 64: Heat Degradation Study of Formoterol Inhalation Solution (Dey) [Dey Confidential—Filed Under Seal].

Akapo Deposition Exhibit 65: Oral Inhalation PDT Meeting Minutes From Apr. 16, 2003 (Dey) [Dey Confidential—Filed Under Seal].

Akapo Deposition Exhibit 66: Akapo, S., et al., *Validation of a RP–HPLC method for the assay of formoterol and its related substances in formoterol fumarate dehydrate drug substance.* J. Pharm. Biomed. Anal. 33 (2003) 935–945.

Akapo Deposition Exhibit 67: Shelf Life Projection For Formoterol Fumarate Inhalation Solutions (Dey) [Dey Confidential—Filed Under Seal].

Akapo Deposition Exhibit 68: E–mail (Dey) [Dey Confidential—Filed Under Seal].

Akapo Deposition Exhibit 69: E–mail (Dey) [Dey Confidential—Filed Under Seal].

Akapo Deposition Exhibit 70: E–mail (Dey) [Dey Confidential—Filed Under Seal].

Akapo Deposition Exhibit 71: Formoterol PDT Meeting Minutes From Jan. 12, 2005 (Dey) [Dey Confidential—Filed Under Seal].

Akapo Deposition Exhibit 72: Analytical Procedures (Formoterol Fumarate Inhalation Solution, 20 mcg/2 mL) (Dey) [Dey Confidential—Filed Under Seal].

Akapo Deposition Exhibit 73: Method Validation Report for HPLC Assay of Formoterol Fumarate and its Related Substances in Formoterol Fumarate Inhalation Solution, 20 mcg/2mL (ATM–716–13) (Dey) [Dey Confidential—Filed Under Seal].

First Banerjee Deposition Transcript, Feb. 13, 2009 (Dey) [Dey Confidential—Filed Under Seal].

First Banerjee Deposition Exhibit 118: Banerjee et al., *Studies on the Effects of Some Additives on the Stability of Injectable Forumlations of Diazepam,* Indian Drugs 29 (8), 361–364 (May 1992).

First Banerjee Deposition Exhibit 119: Letter from Banerjee to Patent Counsel with references (Dey) [Dey Confidential—Filed Under Seal].

First Banerjee Deposition Exhibit 119[A]: Faulds, D., et al., *Formoterol A Review of its Pharmacological Properties and Therapeutic Potential in Reversible Obstructive Airways Disease.* Drugs 42 (1) pp. 115–137 1991 Use Document on Desksite—Not Printed From E–Room.

First Banerjee Deposition Exhibit 119[B]: Maesen, F.P.V., et al., *Formoterol Suspension Aerosol Comparison with Formoterol Solution Aerosol for 12 Weeks in Asthmatic Patients.* Chest 102:1544–1549 (1992) (provided as Document C45).

First Banerjee Deposition Exhibit 119[C]: U.S. Patent No. 6,004,537 (provided as Document A82).

First Banerjee Deposition Exhibit 119[D]: Anderson, G.P., *Formoterol: Pharmacology, moleculer basis of agonism, and mechanism of long duration of a highly potent and selective $\beta_2$–adrenoceptor agonist bronchodilator.* Life Sciences, vol. 52, No. 26 pp. 2145–2160 (1993).

First Banerjee Deposition Exhibit 119[E]: Bartow, R.A., et al., *Formoterol An Update of its Pharmacological Properties and Therapeutic Efficacy in the Management of Asthma Drugs*, 55 (2) pp. 303–322 (Feb. 1998). (provided as Document C2).

First Banerjee Deposition Exhibit 119[F]: PCT Publication WO 99/36095 (provided as Document B34).

First Banerjee Deposition Exhibit 119[G]: PCT Publication WO 99/00134 (provided as Document B30).

First Banerjee Deposition Exhibit 120: File History U.S. Patent No. 6,667,334.

First Banerjee Deposition Exhibit 121: Dey Product Development Monthly Report—Apr. 1999 (Dey) [Dey Confidential—Filed Under Seal].

First Banerjee Deposition Exhibit 122: Dey Product Development Monthly Report—Jun. 1999 (Dey) [Dey Confidential—Filed Under Seal].

First Banerjee Deposition Exhibit 123: Oral Inhalation PDT Meeting Minutes—Oct. 1999 (Dey) [Dey Confidential—Filed Under Seal].

First Banerjee Deposition Exhibit 124: Oral Inhalation PDT Meeting Minutes—Apr. 2000 (Dey) [Dey Confidential—Filed Under Seal].

First Banerjee Deposition Exhibit 125: Formoterol Fumarate Formulation Activities (Dey) [Dey Confidential—Filed Under Seal].

First Banerjee Deposition Exhibit 126: Dey Formulation Composition (Dey) [Dey Confidential—Filed Under Seal].

First Banerjee Deposition Exhibit 127: E–mail patent reminder (Dey) [Dey Confidential—Filed Under Seal].

First Banerjee Deposition Exhibit 128: U.S. Patent No. 7,462,645 (provided as Document A137).

First Banerjee Deposition Exhibit 129: U.S. Patent No. 7,473,710 (provided as Document A139).

First Banerjee Deposition Exhibit 130: U.S. Patent No. 7,465,756 (provided as Document A138).

Second Banerjee Deposition Transcript, Sep. 15, 2009 (Dey) [Dey Confidential—Filed Under Seal].

Second Banerjee Deposition Exhibit 180: Personnel Action Form (Dey) [Dey Confidential—Filed Under Seal].

Second Banerjee Deposition Exhibit 181: Correspondence between Dey and Patent Counsel (Dey) [Dey Confidential—Filed Under Seal].

Second Banerjee Deposition Exhibit 182: Declaration of P. Banerjee dated Sep. 24, 2004 submitted in U.S. Appl. No. 09/887,496.

Second Banerjee Deposition Exhibit 183: Lab Notebook (Dey) [Dey Confidential—Filed Under Seal].

Second Banerjee Deposition Exhibit 184: Formoterol Fumarate Nebulization U.D.—For the treatment of COPD (Dey) [Dey Confidential—Filed Under Seal].

Second Banerjee Deposition Exhibit 185: Citations from Biological Abstracts (Dey) [Dey Confidential—Filed Under Seal].

Second Banerjee Deposition Exhibit 186: Converted concentrations from Formoterol fumarate to Formoterol free base. (Dey) [Dey Confidential—Filed Under Seal].

Carpenter Deposition Transcript, Feb. 5, 2009 (Dey) [Dey Confidential—Filed Under Seal].

Carpenter Deposition Exhbition 99: Dey Scientific Affairs Track record Jan. 2004–Aug. 2007(Dey) [Dey Confidential—Filed Under Seal].

Carpenter Deposition Exhbition 100: Dey to Center for Drug Research—Change of Correspondence (Dey) [Dey Confidential—Filed Under Seal].

Carpenter Deposition Exhbition 101: Minutes from Apr. 23, 2004 NPC Meeting (Dey) [Dey Confidential—Filed Under Seal].

Carpenter Deposition Exhbition 102: Application To Market A New Drug, Biologic, Or An Antibiotic Drug For Human Use (Dey) [Dey Confidential—Filed Under Seal].

Carpenter Deposition Exhbition 103: E–mail transmitting Formoterol Patent Opinion (Dey) [Dey Confidential—Filed Under Seal].

Carpenter Deposition Exhbition 104: Letter to FDA Formoterol Fumarate Inhalation Solution, 20 mcg/mL—Petition To Correct Patent Information (Dey) [Dey Confidential—Filed Under Seal].

Carpenter Deposition Exhbition 105: Letter to FDA Perforomist™ (formoterol fumarate) Inhalation Solution 20 mcg/2 mL Submission of Patent Information (Dey) [Dey Confidential—Filed Under Seal].

Carpenter Deposition Exhbition 106: PDT Update Sep. 23, 2004 (Dey) [Dey Confidential—Filed Under Seal].

Carpenter Deposition Exhbition 107: Formoterol PDT Meeting Minutes From Oct. 13, 2004 (Dey) [Dey Confidential—Filed Under Seal].

Carpenter Deposition Exhbition 108: Chronology Regulatory & Clinical Activities Formoterol Fumarate (Dey) [Dey Confidential—Filed Under Seal].

Carpenter Deposition Exhbition 109: Formoterol–Quality 5% desformyl degradant (Dey) [Dey Confidential—Filed Under Seal].

Carpenter Deposition Exhbition 110: EOP2 FDA Meeting Action Plan (Dey) [Dey Confidential—Filed Under Seal].

Carpenter Deposition Exhbition 111: Memorandum of Meeting Minutes with FDA on May 13, 2003 (Dey) [Dey Confidential—Filed Under Seal].

Carpenter Deposition Exhbition 112: Formoterol PDT Meeting Minutes From Sep. 8, 2004 (Dey) [Dey Confidential—Filed Under Seal].

Carpenter Deposition Exhbition 113: Formoterol Unit Dose for COPD (Dey) [Dey Confidential—Filed Under Seal].

Carpenter Deposition Exhbition 114: Formoterol Pls (Dey) [Dey Confidential—Filed Under Seal].

Carpenter Deposition Exhbition 115: Oral Inhalation PDT Meeting Minutes From Jul. 10, 2002 (Dey) [Dey Confidential—Filed Under Seal].

Carpenter Deposition Exhbition 116: Oral Inhalation PDT Meeting Minutes From Nov. 13, 2002 (Dey) [Dey Confidential—Filed Under Seal].

Carpenter Deposition Exhbition 117: Letter from Dey to FDA Formoterol Fumarate Inhalation Solution, 20 mcg/2 mL Minor Amendment—Patent Certification Amendment (Dey) [Dey Confidential—Filed Under Seal].

First Chaudry Deposition Transcript, Jun. 30, 2009 (Dey) [Dey Confidential—Filed Under Seal].

First Chaudry Deposition Exhibit 142: Deposition of I. Chaudry in Dey v. Ivax Pharmaceuticals in the United States District Court for the Central District of California, Civil Action No. SACV 04–00079 (Dey) [Dey Confidential—Filed Under Seal].

First Chaudry Deposition Exhibit 143: Letter between litigation counsel regarding discovery (Dey) [Dey Confidential—Filed Under Seal].

First Chaudry Deposition Exhibit 144: Correspondence between Dey and Patent Counsel (Dey) [Dey Confidential—Filed Under Seal].

First Chaudry Deposition Exhibit 145: Stability of Formoterol Fumarate in Purified Water (Dey) [Dey Confidential—Filed Under Seal].

First Chaudry Deposition Exhibit 146: Dey Invention Award Plan (Dey) [Dey Confidential—Filed Under Seal].

First Chaudry Deposition Exhibit 147: Dey Inventor Incentive Award Calculations (Dey) [Dey Confidential—Filed Under Seal].

First Chaudry Deposition Exhibit 148: Formoterol Overview Stage II (Dey) [Dey Confidential—Filed Under Seal].

Second Chaudry Deposition Transcript, Jul. 1, 2009 (Dey) [Dey Confidential—Filed Under Seal].

Second Chaudry Deposition Exhibit 126A: Formulation Composition (Dey) [Dey Confidential—Filed Under Seal].

Second Chaudry Deposition Exhibit 149: Oral Inhalation PDT Meeting Minutes From Oct. 2000(Dey) [Dey Confidential—Filed Under Seal].

Second Chaudry Deposition Exhibit 150: Stability and Expiration Dating of Formoterol (Dey) [Dey Confidential—Filed Under Seal].

Second Chaudry Deposition Exhibit 151: Letter regarding Formoterol U.D. (Dey) [Dey Confidential—Filed Under Seal].

Second Chaudry Deposition Exhibit 152: Merck Innovation Award (Dey) [Dey Confidential—Filed Under Seal].

Second Chaudry Deposition Exhibit 153: Sepracor's Rule 30(b)(6) Notice of Deposition in Dey v. Sepracor in the United States District Court for the Southern District of New York, Civil Action No. 1:07–cv–2353 [Dey Confidential—Filed Under Seal].

Second Chaudry Deposition Exhibit 154: Sepracor's Third Rule 30(b)(6) Notice to Dey in Dey v. Sepracor in the United States District Court for the Southern District of New York, Civil Action No. 1:07–cv–2353 [Dey Confidential—Filed Under Seal].

Second Chaudry Deposition Exhibit 155: I. Chaudry Employee Profile (Dey) [Dey Confidential—Filed Under Seal].

Second Chaudry Deposition Exhibit 156: Scientific Affairs MBO 2004 (Dey) [Dey Confidential—Filed Under Seal].

Second Chaudry Deposition Exhibit 157: Scientific Affairs MBO 2005 (Dey) [Dey Confidential—Filed Under Seal].

Second Chaudry Deposition Exhibit 158: Estimate of Nebulization Market Size (Dey) [Dey Confidential—Filed Under Seal].

Second Chaudry Deposition Exhibit 159: Formoterol Fumarate IS Solution pH (Dey) [Dey Confidential—Filed Under Seal].

First Engle Deposition Transcript, Jan. 30, 2009 (Dey) [Dey Confidential—Filed Under Seal].

First Engle Deposition Exhibit 74: Dey Portfolio Presentation (Dey) [Dey Confidential—Filed Under Seal].

First Engle Deposition Exhibit 75: E–mail regarding Formoterol Patent (Dey) [Dey Confidential—Filed Under Seal].

First Engle Deposition Exhibit 76: Minutes from the NPC Meeting Day 2005(Dey) [Dey Confidential—Filed Under Seal].

First Engle Deposition Exhibit 77: Publication and Abstract Plan (Dey) [Dey Confidential—Filed Under Seal].

First Engle Deposition Exhibit 78: Minutes from the Medical Advisors Meeting, May 2005 (Dey) [Dey Confidential—Filed Under Seal].

First Engle Deposition Exhibit 79: 2004 R&D Plan and Project Prioritization (Dey) [Dey Confidential—Filed Under Seal].

First Engle Deposition Exhibit 80: Presentation of Professor Scheuble—Business Development Update (Dey) [Dey Confidential—Filed Under Seal].

First Engle Deposition Exhibit 81:Perforomist Launch Delay Memo (Dey) [Dey Confidential—Filed Under Seal].

First Engle Deposition Exhibit 82: Formoterol U.D. Memo (Dey) [Dey Confidential—Filed Under Seal].

First Engle Deposition Exhibit 83: Timing in 20% Reduction in Sales Force (Dey) [Dey Confidential—Filed Under Seal].

First Engle Deposition Exhibit 84: Dey Award Plan for Inventions (Dey) [Dey Confidential—Filed Under Seal].

First Engle Deposition Exhibit 85: E–mail regarding Sepracor (Dey) [Dey Confidential—Filed Under Seal].

First Engle Deposition Exhibit 86: Presentation of Dey Award for the Perforomist Patents (Dey) [Dey Confidential—Filed Under Seal].

First Engle Deposition Exhibit 87: E–mail regarding out licensing (Dey) [Dey Confidential—Filed Under Seal].

First Engle Deposition Exhibit 88: Co–promotion agreement with Dey and Critical Therapeutics (Dey) [Dey Confidential—Filed Under Seal].

First Engle Deposition Exhibit 89: E–mail regarding 4–year plan impacts (Dey) [Dey Confidential—Filed Under Seal].

First Engle Deposition Exhibit 90: Revised Plaintiff's Privileged Log (Dey) [Dey Confidential—Filed Under Seal].

First Engle Deposition Exhibit 91: Senior Team Meeting Minutes (Dey) [Dey Confidential—Filed Under Seal].

First Engle Deposition Exhibit 92: E–mail for "formoterol disaster" (Dey) [Dey Confidential—Filed Under Seal].

First Engle Deposition Exhibit 93: Dey Net Sales Projection (Dey) [Dey Confidential—Filed Under Seal].

First Engle Deposition Exhibit 94: Pipeline Activity Summary (Dey) [Dey Confidential—Filed Under Seal].

First Engle Deposition Exhibit 95: Antwort Respiratory Strategy (Dey) [Dey Confidential—Filed Under Seal].

First Engle Deposition Exhibit 96: Net Sales Report (Dey) [Dey Confidential—Filed Under Seal].

First Engle Deposition Exhibit 97: Perforomist Net Sales (Dey) [Dey Confidential—Filed Under Seal].

First Engle Deposition Exhibit 98: North America Mgt Presentation—Pipeline Page (Dey) [Dey Confidential—Filed Under Seal].

Second Engle Deposition Transcript, Sep. 16, 2009 (Dey) [Dey Confidential—Filed Under Seal].

Glascott Deposition Transcript, Aug. 13, 2009 (Dey) [Dey Confidential—Filed Under Seal].

Glascott Deposition Exhibit VG1: Sepracor's Second Rule 30(b)(6) Notice to Dey in *Dey* v. *Sepracor* in the United States District Court for the Southern District of New York, Civil Action No. 1:07–cv–2353, Mar. 21, 2007 [Pam Marrs 1] [Dey Confidential—Filed Under Seal].

Glascott Deposition Exhibit VG2: Press Release Mylan's Dey L.P. Announces Establishment of 'J–Code' for Perforomist™ Inhalation Solution.

Glascott Deposition Exhibit VG3: Draft Updated Mecical Policy for Medicare and Medicaid (Dey) [Dey Confidential—Filed Under Seal].

Glascott Deposition Exhibit VG4: Bates Ranges (Dey) [Dey Confidential—Filed Under Seal].

Glascott Deposition Exhibit VG5: Letter to TrustSolutions with additional information regarding Performist™ (Dey) [Dey Confidential—Filed Under Seal].

Glascott Deposition Exhibit VG6: Border, M, *Treatment Algorithms for Chronic Obstructive Pulmonary Disease, Dec. 2006,* Decision Resources, 2006 (Dey) [Dey Confidential—Filed Under Seal].

Glascott Deposition Exhibit VG7: Monie, D., *Chronic Obstructive Pulmonary Disease Treatment & Reimbursement—Findings from a U.S. Survey of PCPs, Pulmonologists, and Managed Care Pharmacy Directors,* Decision Resources, Nov. 2006 (Dey) [Dey Confidential—Filed Under Seal].

Glascott Deposition Exhibit VG8: Review of Dey Sales Projections (Dey) [Dey Confidential—Filed Under Seal].

Glascott Deposition Exhibit VG9: Situational Analysis of Chronic Obstructive Pulmonary Disease (Dey) [Dey Confidential—Filed Under Seal].

Glascott Deposition Exhibit VG10: US Formoterol Market Overview, Mar. 2002 (Dey) [Dey Confidential—Filed Under Seal].

Glascott Deposition Exhibit VG11: Unit Dose Opportunity Assessment (Dey) [Dey Confidential—Filed Under Seal].

Glascott Deposition Exhibit VG12: Marketing Definition Memo (Dey) [Dey Confidential—Filed Under Seal].

Glascott Deposition Exhibit VG13: New Market Definitions (Dey) [Dey Confidential—Filed Under Seal].

Glascott Deposition Exhibit VG14: Price per day Comparison on WAC (Dey) [Dey Confidential—Filed Under Seal].

Glascott Deposition Exhibit VG15: Foromterol Launch Forecast (Dey) [Dey Confidential—Filed Under Seal].

Glascott Deposition Exhibit VG16: Perforomist™ Projections (Dey) [Dey Confidential—Filed Under Seal].

Glascott Deposition Exhibit VG17: Perforomist™ Retail Price Summary (Dey) [Dey Confidential—Filed Under Seal].

Glascott Deposition Exhibit VG18: E–mail regarding Perforomist™ Launch Offer Recco (Dey) [Dey Confidential—Filed Under Seal].

Glascott Deposition Exhibit VG19: Pricing Recommendation for Perforomist™ Inhalation Solution (Dey) [Dey Confidential—Filed Under Seal].

Glascott Deposition Exhibit VG20: Branded Pipeline Forecast by Indication and Segment (Dey) [Dey Confidential—Filed Under Seal] [Pam Marrs 30].

Glascott Deposition Exhibit VG21: E–mail regarding discussion with Bankers(Dey) [Dey Confidential—Filed Under Seal] [Pam Marrs 27].

Glascott Deposition Exhibit VG22: Formoterol Lost Profits (Dey) [Dey Confidential—Filed Under Seal] [Pam Marrs 23].

Glascott Deposition Exhibit VG23: Optimal Bronchodilation in COPD: Making a Long Story Short (Dey) [Dey Confidential—Filed Under Seal].

Glascott Deposition Exhibit VG24: E–mail FFIS Field Strategy (Dey) [Dey Confidential—Filed Under Seal].

Glascott Deposition Exhibit VG25: E–mail Retention and Maintenance C27100 (Dey) [Dey Confidential—Filed Under Seal].

Glascott Deposition Exhibit VG26: E–mail DuoNeb vs Brovana Sales aid (Dey) [Dey Confidential—Filed Under Seal].

Glascott Deposition Exhibit VG27: Formoterol Competitive Workshop (Dey) [Dey Confidential—Filed Under Seal].

Glascott Deposition Exhibit VG28: Brovana War Games Summary (Dey) [Dey Confidential—Filed Under Seal].

Glascott Deposition Exhibit VG29: Dey Formoterol Forecast Compared to Arformoterol forecast (Dey) [Dey Confidential—Filed Under Seal].

Glascott Deposition Exhibit VG30: Perforomist Message to Internal and External Customers (Dey) [Dey Confidential—Filed Under Seal].

Glascott Deposition Exhibit VG31: E–mail on Back–orders- (Dey) [Dey Confidential—Filed Under Seal].

Glascott Deposition Exhibit VG32: Marketing Department Org Chart (Dey) [Dey Confidential—Filed Under Seal].

Glascott Deposition Exhibit VG33: Formoterol Launch Plan Update (Dey) [Dey Confidential—Filed Under Seal].

Glascott Deposition Exhibit VG34: Formoterol Transition Plan (Dey) [Dey Confidential—Filed Under Seal].

Glascott Deposition Exhibit VG35: Formoterol Launch Commercialization Team (Dey) [Dey Confidential—Filed Under Seal].

Glascott Deposition Exhibit VG36: Formoterol Update (Dey) [Dey Confidential—Filed Under Seal].

Glascott Deposition Exhibit VG37: FFIS Launch Commercialization Meeting Jan. 10, 2007 (Dey) [Dey Confidential—Filed Under Seal].

Glascott Deposition Exhibit VG38: FFIS Launch Commercialization Meeting Feb. 1, 2007 (Dey) [Dey Confidential—Filed Under Seal].

Glascott Deposition Exhibit VG39: Perforomist™ National Sales Plan (Dey) [Dey Confidential—Filed Under Seal].

Glascott Deposition Exhibit VG40: 2008 Perforomist™ Inhalation Solution Launch Marketing Plan (Dey) [Dey Confidential—Filed Under Seal].

Glascott Deposition Exhibit VG41: 2008 Perforomist™ Inhalation Solution Launch Marketing Plan (Dey) [Dey Confidential—Filed Under Seal].

Gupta Deposition Transcript, Aug. 11, 2009 (Dey) [Dey Confidential—Filed Under Seal].

Gupta Deposition Exhibit DX165: Updated Summary of Formoterol PAI Preparation Meetings (Dey) [Dey Confidential—Filed Under Seal].

Gupta Deposition Exhibit DX166: Stability Data for Formoterol Fumarate Inhalation Solution, 20 mcg/2mL (Dey) [Dey Confidential—Filed Under Seal].

Gupta Deposition Exhibit DX167: Finished Product Methods Requiring Transfer Qualifications (Dey) [Dey Confidential—Filed Under Seal].

Gupta Deposition Exhibit DX168: HPLC Assay of Formoterol Fumarate and its Related Substances in Formoterol Fumarate Inhalation Solution (20 mcg/2mL and 20 mcg/0.5 mL) (Dey) [Dey Confidential—Filed Under Seal].

Gupta Deposition Exhibit DX169: Stability Study Protocol for Dey's Perforomist™ (Formoterol Fumarate) Inhalation Solution Against Sepracor's Brovana™ (Arformoterol Tartrate) Inhalation Solution (Dey) [Dey Confidential—Filed Under Seal].

Gupta Deposition Exhibit DX170: Analyical Development Test Request for Brovana™ (Arformoterol Tartrate) Inhalation Solution 15 mcg/2 mL (Dey) [Dey Confidential—Filed Under Seal].

Gupta Deposition Exhibit DX171: Analytical Development Test Request for Formoterol Fumarate Inhalation Solution 20 mcg/2 mL (Dey) [Dey Confidential—Filed Under Seal].

Gupta Deposition Exhibit DX172: Analytical Development Test Request for Formoterol Fumarate Inhalation Solution 20 mcg/2 mL—1 month @ 25±2 ° C./60±5 %RH (Dey) [Dey Confidential—Filed Under Seal].

Gupta Deposition Exhibit DX173: Analytical Development Test Request for Brovana™ (Arformoterol Tartrate) Inhalation Solution, 15 mcg/2 mL—1 month @ 25±2 ° C./60±5 %RH (Dey) [Dey Confidential—Filed Under Seal].

Gupta Deposition Exhibit DX174: Analytical Development Test Request for Formoterol Fumarate Inhalation Solution 20 mcg/2 mL—2 month @ 25±2 ° C./60±5 %RH (Dey) [Dey Confidential—Filed Under Seal].

Gupta Deposition Exhibit DX175: Analytical Development Test Request for Brovana™ (Arformoterol Tartrate) Inhalation Solution, 15 mcg/2 mL—2 month @ 25±2 ° C. 60±5 %RH (Dey) [Dey Confidential—Filed Under Seal].

Gupta Deposition Exhibit DX176: Lab Notebook (Dey).

Gupta Deposition Exhibit DX177: Lab Notbook (Dey) [Dey Confidential—Filed Under Seal].

Gupta Deposition Exhibit DX178: Akapo, et al. *Evaluation of Interconversion of (RR)– and (SS)–Enantiomers in Perforomist™ (FormoterolFumarate) and Brovana™ (Arformoterol Tartrate) Inhalation Solutions* (Dey) [Dey Confidential—Filed Under Seal].

Jones Deposition Transcript, Sep. 5, 2009 (Dey) [Dey Confidential—Filed Under Seal].

Jones Deposition Exhibit DX1: Serpacor's Rule 30(b)(6) Notice of Deposition of Dey in *Dey* v. *Sepracor* in the United States District Court for the Southern District of New York, Civil Action No. 1:07–cv–2353 (Dey) [Dey Confidential—Filed Under Seal].

Jones Deposition Exhibit DX2: Dey's Initial Disclosures in *Dey* v. *Sepracor* in the United States District Court for the Southern District of New York, Civil Action No. 1:07–cv–2353 (Dey) [Dey Confidential—Filed Under Seal].

Jones Deposition Exhibit DX3: Serpacor's First Set of Requests for the Production of Documents to Dey in *Dey* v. *Sepracor* in the United States District Court for the Southern District of New York, Civil Action No. 1:07–cv–2353 (Dey) [Dey Confidential—Filed Under Seal].

Jones Deposition Exhibit DX4: Serpacor's Second Set of Requests for the Production of Documents to Dey in *Dey* v. *Sepracor* in the United States District Court for the Southern District of New York, Civil Action No. 1:07–cv–2353 (Dey) [Dey Confidential—Filed Under Seal].

Jones Deposition Exhibit DX5: Serpacor's Third Set of Requests for the Production of Documents to Dey in *Dey* v. *Sepracor* in the United States District Court for the Southern District of New York, Civil Action No. 1:07–cv–2353 (Dey) [Dey Confidential—Filed Under Seal].

Jones Deposition Exhibit DX6: Subpoena of Heller Ehrman in *Dey* v. *Sepracor* in the United States District Court for the Southern District of New York, Civil Action No. 1:07–cv–2353 (Dey) [Dey Confidential—Filed Under Seal].

Jones Deposition Exhibit DX7: Revised Agreement for Electronic Discovery in *Dey* v. *Sepracor* in the United States District Court for the Southern District of New York, Civil Action No. 1:07–cv–2353 (Dey) [Dey Confidential—Filed Under Seal].

Kling Deposition Transcript, Aug. 20, 2009 (No Exhibits) (Dey) [Dey Confidential—Filed Under Seal].

Laskar Deposition Transcript, Sep. 11, 2008 (Dey) [Dey Confidential—Filed Under Seal].

Laskar Deposition Exhibit DX34: Orange Book Detail Search for Formoterol Fumarate.

Laskar Deposition Exhibit DX35: NDA Description and Composition of the Drug Product (Formoterol Fumarate Inhalation Solution, 20 mcg/2 mL (Dey) [Dey Confidential—Filed Under Seal].

Laskar Deposition Exhibit DX36: Oral Inhalation PDT Meeting Minutes From Jul. 9, 2003 (Dey) [Dey Confidential—Filed Under Seal].

Laskar Deposition Exhibit DX37: Oral Inhalation PDT Meeting Minutes From Feb. 11, 2004 (Dey) [Dey Confidential—Filed Under Seal].

Laskar Deposition Exhibit DX38: Pharmaceutical Development MBOs (Dey) [Dey Confidential—Filed Under Seal].

Laskar Deposition Exhibit DX39: Date of the formulation of the 10 mcg/mL composition. (Dey) [Dey Confidential—Filed Under Seal].

Laskar Deposition Exhibit DX40: Ayres, J, et al., *Student Experiments In Pharmaceutics I.V. Additives, Chemical Incompatibilities, Kinetics, And The Arrhenius Equation.* American Journal of Pharmaceutical Education, Student Experiments in Pharmaceutics, pp. 58–68.

Laskar Deposition Exhibit DX41: Laskar, P., et al., *Degradation of Carmustine in Aqueous Media.* Journal of Pharmaceutical Sciences, vol. 66, No. 8, pp. 1073–1076, Aug. 1977.

Laskar Deposition Exhibit DX42: U.S. Patent Publication 2005/0009836.

Laskar Deposition Exhibit DX43: PCT Publication WO 93/20796.

Laskar Deposition Exhibit DX44: Pharmaceutical Development Report Formoterol Fumarate Inhalation Solution 20 mcg/2 mL (Dey) [Dey Confidential—Filed Under Seal].

Laskar Deposition Exhibit DX45: U.S. Patent No. 6,161,536 (provided as Document A95).

Laskar Deposition Exhibit DX46: Formoterol PDT Meeting Minutes From May 11, 2005 (Dey) [Dey Confidential—Filed Under Seal].

Laskar Deposition Exhibit DX47: Draft Minutes from the NPC Meeting held Jul. 19, 2005 (Dey) [Dey Confidential—Filed Under Seal].

Laskar Deposition Exhibit DX48: Pharmaceutical Development MBOs 2005 (Dey) [Dey Confidential—Filed Under Seal].

Laskar Deposition Exhibit DX49: Dey Innovation Note (Dey) [Dey Confidential—Filed Under Seal].

Laskar Deposition Exhibit DX50: Edits/Questions for Pharm/Tox Sections (Dey) [Dey Confidential—Filed Under Seal].

Lee Deposition Transcript, Jul. 14, 2009 (Dey) [Dey Confidential—Filed Under Seal].

Lee Deposition Exhibit DX160: Ex Parte Reexamination Request for U.S. Patent No. 6,667,344 (Copy not submitted, see Reexamination No. 90/010,488).
Lee Deposition Exhibit DX161: Ex Parte Reexamination Request for U.S. Patent No. 6,814,953 (Copy not submitted, see Reexamination No. 90/010,489).
Lee Deposition Exhibit DX162: Privilege Log (Dey) [Dey Confidential—Filed Under Seal].
Lee Deposition Exhibit DX163: Order Granting Ex Parte Reexamination Request for U.S. Patent No. 6,667,344 (Copy not submitted, see Reexamination No. 90/010,488).
Lee Deposition Exhibit DX164: Order Granting Ex Parte Reexamination Request for U.S. Patent No. 6,814,953 (Copy not submitted, see Reexamination No. 90/010,489).
First Marrs Deposition Transcript, Aug. 12, 2009 (Dey) [Dey Confidential—Filed Under Seal].
First Marrs Deposition Exhibit PM1: Sepracor's Second Rule 30(b)(6) Notice to Dey in *Dey* v. *Sepracor* in the United States District Court for the Southern District of New York, Civil Action No. 1:07–cv–2353 [VG1] (Dey) [Dey Confidential—Filed Under Seal].
First Marrs Deposition Exhibit PM2: Dey's Supplement Objections And Responses To Sepracor's First Set Of Interrogatories To Dey in *Dey* v. *Sepracor* in the United States District Court for the Southern District of New York, Civil Action No. 1:07–cv–2353 (Dey) [Dey Confidential—Filed Under Seal].
First Marrs Deposition Exhibit PM3: Dey Net Sales Peroformist (Dey) [Dey Confidential—Filed Under Seal].
First Marrs Deposition Exhibit PM4: Dey Performist 2008 Actual (Dey) [Dey Confidential—Filed Under Seal].
First Marrs Deposition Exhibit PM5: Dey Performist 2009 Actual (Dey) [Dey Confidential—Filed Under Seal].
First Marrs Deposition Exhibit PM6: 2007 Key Indicator Graphs (Dey) [Dey Confidential—Filed Under Seal].
First Marrs Deposition Exhibit PM7: Formoterol UD NDA Communication (Dey) [Dey Confidential—Filed Under Seal].
First Marrs Deposition Exhibit PM8: Investment Committee Meeting (Dey) [Dey Confidential—Filed Under Seal].
First Marrs Deposition Exhibit PM9: Capital Request for Molds (Dey) [Dey Confidential—Filed Under Seal].
First Marrs Deposition Exhibit PM10: E–mail regarding vial design (Dey) [Dey Confidential—Filed Under Seal].
First Marrs Deposition Exhibit PM11: Performist Inventory on Hand (Dey) [Dey Confidential—Filed Under Seal].
First Marrs Deposition Exhibit PM12: E–mail on Back–orders (Dey) [Dey Confidential—Filed Under Seal] [VG31].
First Marrs Deposition Exhibit PM13: Message to the Senior Team (Dey) [Dey Confidential—Filed Under Seal].
First Marrs Deposition Exhibit PM14: Summary of Net Sales Changes 2007 & 2008 (Dey) [Dey Confidential—Filed Under Seal].
First Marrs Deposition Exhibit PM15: Impact on Formoterol (Dey) [Dey Confidential—Filed Under Seal].
First Marrs Deposition Exhibit PM16: Various Projections in 2015 Scenarios (Dey) [Dey Confidential—Filed Under Seal].
First Marrs Deposition Exhibit PM17: Dey Amendment No. 3 to Form S–1 Registration Statement.
First Marrs Deposition Exhibit PM18: E–mail regarding Formoterol Forward (Dey) [Dey Confidential—Filed Under Seal].
First Marrs Deposition Exhibit PM19: Orange Book Detail Search for Arbuterol Sulfate.
First Marrs Deposition Exhibit PM20: U.S. Patent No. 6,632,842 (provided as Document A128).
First Marrs Deposition Exhibit PM21: HIP Analysis (Dey) [Dey Confidential—Filed Under Seal].
First Marrs Deposition Exhibit PM22: Formoterol Forecast based on Launch Dates (Dey) [Dey Confidential—Filed Under Seal].
First Marrs Deposition Exhibit PM23: Formoterol Lost Profits (Dey) [Dey Confidential—Filed Under Seal] [VG22].
First Marrs Deposition Exhibit PM24: Formoterol Increased sales from early launch of 2 ml vs lost LV sales (Dey) [Dey Confidential—Filed Under Seal].
First Marrs Deposition Exhibit PM25: Formoterol Oct. 2007 Launch Sales (Dey) [Dey Confidential—Filed Under Seal].
First Marrs Deposition Exhibit PM26: Formoterol Low Volume Discontinuance (Dey) [Dey Confidential—Filed Under Seal].
First Marrs Deposition Exhibit PM27: E–mail regarding discussion with Bankers (Dey) [Dey Confidential—Filed Under Seal].
First Marrs Deposition Exhibit PM28: E–mail regarding conversation with bankers, extended (Dey) [Dey Confidential—Filed Under Seal].
First Marrs Deposition Exhibit PM29: E–mail regarding "beta–agonist" (Dey) [Dey Confidential—Filed Under Seal].
First Marrs Deposition Exhibit PM30: Branded Pipeline Forecast by Indication and Segment (Dey) [Dey Confidential—Filed Under Seal].
First Marrs Deposition Exhibit PM31: Branded Budgeted Development Projects (Dey) [Dey Confidential—Filed Under Seal].
First Marrs Deposition Exhibit PM32: Dey Sales Revised 4 Year Plan (Dey) [Dey Confidential—Filed Under Seal].
First Marrs Deposition Exhibit PM33: Dey P&L Summary (Dey) [Dey Confidential—Filed Under Seal].
First Marrs Deposition Exhibit PM34: Formoterol P&L to 2011 (Dey) [Dey Confidential—Filed Under Seal].
First Marrs Deposition Exhibit PM35: Market Share Forecast (Dey) [Dey Confidential—Filed Under Seal].
First Marrs Deposition Exhibit PM36: Patent Share Chart (Dey) [Dey Confidential—Filed Under Seal].
First Marrs Deposition Exhibit PM37: Dey Sales by Product (Dey) [Dey Confidential—Filed Under Seal].
First Marrs Deposition Exhibit PM38: Dey Sales & Margin Before CAMS (Dey) [Dey Confidential—Filed Under Seal].
First Marrs Deposition Exhibit PM39: Dey 2008 Budget (Dey) [Dey Confidential—Filed Under Seal].
First Marrs Deposition Exhibit PM40: Dey 2007 Strategic Plan (Dey) [Dey Confidential—Filed Under Seal].
Second Marrs Deposition Transcript, Sep. 24, 2009 (Dey) [Dey Confidential—Filed Under Seal].
Second Marrs Deposition Exhibit PM41: Dey Sales All Products (Dey) [Dey Confidential—Filed Under Seal].
Second Marrs Deposition Exhibit PM42: 2008 Product Line P&L Analysis vol. 1 Actual (Dey) [Dey Confidential—Filed Under Seal].
Second Marrs Deposition Exhibit PM43: 2008 Product Line P&L Analysis vol. 2 Actual (Dey) [Dey Confidential—Filed Under Seal].
Second Marrs Deposition Exhibit PM44: Dey Gross to Net Sales (Dey) [Dey Confidential—Filed Under Seal].

Second Marrs Deposition Exhibit PM45: Fixed Assets Acquired Specifically for Perforomist (Dey) [Dey Confidential—Filed Under Seal].
Second Marrs Deposition Exhibit PM46: Perforomist Rebate for Neighborhood Health Plan (Dey) [Dey Confidential—Filed Under Seal].
Second Marrs Deposition Exhibit PM47: Perforomist Rebate for Beyond Rx (Dey) [Dey Confidential—Filed Under Seal].
Second Marrs Deposition Exhibit PM48: Contract Renewal for Virtua Health (Dey) [Dey Confidential—Filed Under Seal].
Second Marrs Deposition Exhibit PM49: FFDIS Developing a US Pricing and Market Access Strategy (Dey) [Dey Confidential—Filed Under Seal].
Second Marrs Deposition Exhibit PM50: Perforomist™ Miscellaneous Correspondence (Dey) [Dey Confidential—Filed Under Seal].
Second Marrs Deposition Exhibit PM51: New Market Definitions (Dey) [Dey Confidential—Filed Under Seal].
Second Marrs Deposition Exhibit PM52: E–mail on FFIS Pre–appr Field Strategy (Dey) [Dey Confidential—Filed Under Seal].
Second Marrs Deposition Exhibit PM53: Branded Pipeline Forecasts by Indication and Segment (Dey) [Dey Confidential—Filed Under Seal].
Mercanti Deposition Transcript, Sep. 23, 2009 (Dey) [Dey Confidential—Filed Under Seal].
Mercanti Deposition Exhibit 131: U.S. Patent No. 7,541,385 (provided as Document A140).
Mercanti Deposition Exhibit 132: Declaration of Michael N. Mercanti, Esq. in Support of Dey's Opposition to Sepracor's Motion for Leave to File an Amended Answer and Counterclaims in Dey v. Sepracor in the United States District Court for the Southern District of New York, Civil Action No. 1:07–cv–2353 (Dey) [Dey Confidential—Filed Under Seal] Use Version on Desksite Not Printed From E–Room.
Mercanti Deposition Exhibit 133: Dey's Supplemental Objections And Responses To Sepracor's First Set Of Interrogatories To Dey (Dey) [Dey Confidential—Filed Under Seal].
Mercanti Deposition Exhibit 134: U.S. Patent No. 7,462,645 and partial File History.
Mercanti Deposition Exhibit 135: U.S. Patent No. 7,473,710 and partial File History.
Mercanti Deposition Exhibit 136: U.S. Patent No. 7,465,756 and partial File History.
Mercanti Deposition Exhibit 137: U.S. Patent No. 7,541,385 and partial File History.
Mercanti Deposition Exhibit 138: Partial File History U.S. Appl. No. 09/887,496.
Mercanti Deposition Exhibit 139: Final Office Action mailed May 26, 2009 in U.S. Appl. No. 10/145,978.
Mercanti Deposition Exhibit 140: Privileged Log (Dey) [Dey Confidential—Filed Under Seal].
Mercanti Deposition Exhibit 141: Sepracor's Answer And Counterclaims To Dey's Second Supplemental Complaint in Dey v. Sepracor in the United States District Court for the Souther District of New York, Civil Action No. 1:07–cv–2353 (Dey) [Dey Confidential—Filed Under Seal].
Pham Deposition Transcript, Sep. 9, 2008 (Dey) [Dey Confidential—Filed Under Seal].
Pham Deposition Exhibit DX08: U.S. Patent No. 6,677,344 (provided as Document A129).
Pham Deposition Exhibit DX09: U.S. Patent No. 6,814,953 (provided as Document A133).
Pham Deposition Exhibit DX10: U.S. Patent No. 7,348,362 (provided as Document A136).
Pham Deposition Exhibit DX11: Project Assignment For Unit Dose Scientists (Dey) [Dey Confidential—Filed Under Seal].
Pham Deposition Exhibit DX12: Declaration and Power of Attorney for U.S. Appl. No. 09/887,281.
Pham Deposition Exhibit DX13: Formoterol Fumarate Inhalation Solution 20 mcg/2 mL Original NDA (Dey) [Dey Confidential—Filed Under Seal].
Pham Deposition Exhibit DX14: Formoterol Fumarate Inhalation Solution Clinical Batches (Dey) [Dey Confidential—Filed Under Seal].
Pham Deposition Exhibit DX15: Formulation Selection Memo (Dey) [Dey Confidential—Filed Under Seal].
Pham Deposition Exhibit DX16: Pharmaceutical Development MBOs (Dey) [Dey Confidential—Filed Under Seal].
Pham Deposition Exhibit DX17: Formoterol Solubility and pH Stability Profile (Dey) [Dey Confidential—Filed Under Seal].
Pham Deposition Exhibit DX18: U.S. Patent No. 6,040,344 (provided as Document A85).
Pham Deposition Exhibit DX19: Petitions to Correct Inventorship in Patent No. 6,667,344.
Pham Deposition Exhibit DX20: Petitions to Correct Inventorship in Patent No. 6,814,953.
Pham Deposition Exhibit DX21: Application for Patent No. 7,348,362.
Pham Deposition Exhibit DX22: Petitions to Correct Inventorship in U.S. Appl. No. 10/887,785.
Pham Deposition Exhibit DX23: Formoterol Updates (Dey) [Dey Confidential—Filed Under Seal].
Pham Deposition Exhibit DX24: Maesen, FP., et al., *Formoterol suspension aerosol. Comparison with formoterol solution aerosol for 12 weeks in asthmatic patients.* Chest 102:1544–1549 (1992) (provided as Document C45).
Pham Deposition Exhibit DX25: Merck Innovation Award (Dey) [Dey Confidential—Filed Under Seal].
Pham Deposition Exhibit DX26: Preliminary Stability Assessment Of Formoterol Fumarate In Aqueous Solution (Dey) [Dey Confidential—Filed Under Seal].
Pham Deposition Exhibit DX27: Formulation Development of Formoterol Inhalation Unit Dose (Dey) [Dey Confidential—Filed Under Seal].
Pham Deposition Exhibit DX28: Summary of Formoterol Unit Dose Formulation Development (Dey) [Dey Confidential—Filed Under Seal].
Pham Deposition Exhibit DX29: Formulation Selection Justification Report (Dey) [Dey Confidential—Filed Under Seal].
Pham Deposition Exhibit DX30: Formoterol Unit Dose—Timeline and Key Milestones (Dey) [Dey Confidential—Filed Under Seal].
Pham Deposition Exhibit DX31: Letter to D. Rieger (Dey) [Dey Confidential—Filed Under Seal].
Pham Deposition Exhibit DX32: U.S. Patent No. 3,994,974 (provided as Document A23).
Pham Deposition Exhibit DX33: Response to Final Office Action, mailed Apr. 22, 2003 in U.S. Appl. No. 09/887,281.
Rieger Deposition Transcript, Aug. 19, 2009 (Dey) [Dey Confidential—Filed Under Seal].

Rieger Deposition Exhibit DX179: Feb. 25, 2003 Fax Transmission from Partha S. Banerjee to Dale L. Rieger, Ph.D.; Composition of Formoterol Clinical Formulation (Dey) [Dey Confidential—Filed Under Seal].

A Comparative Stability Study Of Formoterol In Active Substance Concentrate (US Patent #6,150,418 [to Hochrainer et al.])and Dey's Formoterol Fumarate Inhalation Solutions Oct. 10, 2005.

Stenesh, J., *Dictionary of Biochemistry and Molecular Biology* (2d ed. 1989), p. 364.

Sterns, R.H. et al., *Salt and water: read the package insert,* Q. J. Med. (2003), 96:549–552.

Bates, R. et al., *Standards for pH Measurements in Isotonic Saline Media of Ionic Strength I=0.16,* Analytical Chemistry (vol. 50, No. 9, Aug. 1978), 1295–1300.

Roy, R. et al., *Buffer Standards for the Physiological pH of Zwitterionic Compounds, MOBS and TABS from 5 to 55 °C.,* J. Solution Chemistry (vol. 33, No. 10, Oct. 2004), pp. 1199–1211.

Docket Sheet dated Apr. 5, 2011 in *Dey v. Sepracor* in the United States District Court for the Southern District of New York, Civil Action No. 1:07–cv–02353–JGK–RLE, Mar. 21, 2007.

Docket Sheet dated Apr. 5, 2011 in *Dey v. Teva* in the United States District Court for the Northern District of West Virginia, Civil Action No. 1:09–cv–00087–IMK, Jun. 23, 2009.

Defendant's Supplemental Responses to Plaintiffs' First Set of Interrogatories dated Jan. 21, 2011 in *Dey v. Teva* in United States District Court for the Northern District of West Virginia, Civil Action No. 1:09–cv–00087–IMK, Jun. 23, 2009 (Teva) [Dey Confidential—Filed Under Seal] [Teva Confidential—Redacted].

Defendant Teva's Opening Memorandum in Support of Its Claim Construction of the Patents–in–Suit dated Oct. 1, 2010 in *Dey v. Teva* in United States District Court for the Northern District of West Virginia, Civil Action No. 1:09–cv–00087–IMK, Jun. 23, 2009.

Defendant Teva's Opening Memorandum in Support of Its Claim Construction of the Patents–in–Suit, Exhibit A: U.S. Patent No. 6,667,344.

Defendant Teva's Opening Memorandum in Support of Its Claim Construction of the Patents–in–Suit, Exhibit B: U.S. Patent No. 6,814,953.

Defendant Teva's Opening Memorandum in Support of Its Claim Construction of the Patents–in–Suit, Exhibit C: U.S. Patent No. 7,348,362.

Defendant Teva's Opening Memorandum in Support of Its Claim Construction of the Patents–in–Suit, Exhibit D: U.S. Patent No. 7,462,645.

Defendant Teva's Opening Memorandum in Support of Its Claim Construction of the Patents–in–Suit, Exhibit E (6 parts): Excerpts from the Reexamination Files of the '344 Patent (Reexamination No. 90/010,488) and the '953 Patent (Reexamination No. 90/010,489).

Defendant Teva's Opening Memorandum in Support of Its Claim Construction of the Patents–in–Suit, Exhibit F (4 parts): Excerpts from the File History of U.S. Appl. No. 09/887,281.

Defendant Teva's Opening Memorandum in Support of Its Claim Construction of the Patents–in–Suit, Exhibit G (8 parts): Excerpts from the File History of U.S. Appl. No. 10/138,866.

Defendant Teva's Opening Memorandum in Support of Its Claim Construction of the Patents–in–Suit, Exhibit H (6 parts): Excerpts from the File History of U.S. Appl. No. 10/887,785.

Defendant Teva's Opening Memorandum in Support of Its Claim Construction of the Patents–in–Suit, Exhibit I (4 parts): Excerpts from the File History of U.S. Appl. No. 11/688,429.

Defendant Teva's Opening Memorandum in Support of Its Claim Construction of the Patents–in–Suit, Exhibit J: Claim Chart.

Defendant Teva's Opening Memorandum in Support of Its Claim Construction of the Patents–in–Suit, Exhibit K: Parties' Agreed Claim Constructions.

Dey's Memorandum in Support of their Claim Construction (and Exhibits 1–22) dated Oct. 1, 2010 in *Dey v. Teva* in the United States District Court for the Northern District of West Virginia, Civil Action No. 1:09–cv–00087–IMK, Jun. 23, 2009.

Teva's Rebuttal Memorandum on the Issue of Claim Construction of the Patents–in–Suit dated Oct. 15, 2010.

Dey's Rebuttal Claim Construction Report (and Exhibits 23–24) dated Oct. 15, 2010.

Expert Report of Dr. Gordon Rausser Footnote 52: Chronic bronchitis and emphysema prevalence in U.S. adults (age 18 and older), 1999–2008.

Expert Report of Dr. Gordon Rausser Footnote 52: Estimated lifetime asthma diagnosis prevalence in children and adults in the US 1997–2008 (0–17 yrs).

Expert Report of Dr. Gordon Rausser Footnote 31: Connolly et al., *Inhaler Technique of Elderly Patients:Comparison of Metered–dose Inhalers and Large Volume Spacer Devices,* Age and Ageing (vol. 24, No. 3, 1995), pp. 190–192.

Expert Report of Dr. Gordon Rausser Footnote 29: Armitage, J.M. et al., *Inhaler Technique in the Elderly,* Age and Ageing (vol. 17, No. 4, 1988), pp. 275–278.

Expert Report of Dr. Gordon Rausser Footnote 43: Boe, J. et al., *European Society Guidelines on the use of nebulizers,* Eur. Respir. J. (vol. 18, 2001), pp. 228–242.

Expert Report of Dr. Gordon Rausser Footnote 28: Labrune, S. et al., *Inhaled therapy in asthma: Metered–dose inhaler experience,* Monaldi Arch. Chest Dis. (vol. 49, No. 3, 1994), pp. 254–257.

Expert Report of Dr. Gordon Rausser Footnote 40: *Perforomist Inhalation Solution Data Presented At American Thoracic Society Conference,* Medical News Today (May 20, 2009) (located at http://www.medicalnewstoday.com/articles/150812.php).

Expert Report of Dr. Gordon Rausser Footnote 27: Schmidt, D. et al., *Effect of enantiomers of formoterol on inherent and induced tone in guinea–pig trachea and human bronchus,* Naunyn–Schmiedeberg's Arch. Pharmacol. (vol. 261, 2000), pp. 405–409.

Expert Report of Dr. Gordon Rausser Footnote 4: Seemungal T. et al., *Time Course and Recovery of Exacerbations in Patients with Chronic Obstructive Pulmonary Disease,* Am. J. Respir. Crit. Care Med. 161:1608–1613 (2000).

Expert Report of Leslie Hendeles Exhibit 17: Beasley, R. et al., *Preservatives in Nebulizer Solutions: Risks without Benefit—A Further Comment,* Pharmacotherapy (vol. 19, No. 4, 1999), pp. 473–474.

Expert Report of Leslie Hendeles Exhibit 18: *Sterility Requirements for Inhalation Solution Products,* 62 Fed. Reg. 49,638 (Sep. 23, 1997).

Expert Report of Leslie Hendeles Exhibit 19: *Sterility Requirement for Aqueous–Based Drug Products for Oral Inhalation,* 65 Fed. Reg. 34,082 (May 26, 2000).

Expert Report of Leslie Hendeles Exhibit 20: U.S. Dept. Health & Human Services, *Approved Drug Products with Therapeutic Equivalence Evaluations,* (13th ed., 1993) p. 3–7.

Expert Report of Leslie Hendeles Exhibit 21: *Physicians' Desk Reference* (47th ed., 1993), pp. 582–585.

Expert Report of Leslie Hendeles Exhibit 22: *Physicians' Desk Reference* (52d ed., 1998), pp. 2657–2659.

Expert Report of Leslie Hendeles Exhibit 23: *Physicians' Desk Reference* (52d ed., 1998), pp. 1556–1557.

Expert Report of Leslie Hendeles Exhibit 24: File History for Accuneb Trademark Application No. 75/615,399.

Expert Report of Leslie Hendeles Exhibit 26: *Prescribing Information for Pulmicort RespulesTM (budesonide inhalation suspension)0.25 mg and 0.5 mg* (revised Aug. 4, 2000).

Expert Report of Leslie Hendeles Exhibit 27: *Physicians' Desk Reference* (54th ed., 2000), pp. 2316–2318.

Expert Report of Leslie Hendeles Exhibit 29: *Physicians' Desk Reference* (52d ed., 1998), pp. 702–704.

Expert Report of Leslie Hendeles Exhibit 30: *Physicians' Desk Reference* (52d ed., 1998), p. 560.

Expert Report of Leslie Hendeles Exhibit 31: *Physicians' Desk Reference* (52d ed., 1998), pp. 2368–2369.

Expert Report of Leslie Hendeles Exhibit 32: Boehringer Ingelheim Pharmaceuticals, Inc., *Prescribing Information for Atrovent®* (revised Oct. 1998).

Expert Report of Leslie Hendeles Exhibit 42: Hendeles et al., *Dose–Response Of Inhaled Diltiazem On Airway Reactivity To Methacholine And Exercise In Subjects With Mild Asthma,* Clin. Pharmacol. Ther. (vol. 43, Apr. 1988), pp. 387–392.

Expert Report of Leslie Hendeles Exhibit 45: Lindberg et al., *The effects of formoterol, a long–acting β–adrenoceptor agonist, on mucociliary activity,* Eur. J. Pharmacology (vol. 285, No. 3, Oct. 24, 1995), pp. 275–280.

Expert Report of Leslie Hendeles Exhibit 101: *Prescribing Information for Brovana (arformoterol tartrate) Inhalation Solution* (available at http://www.accessdata.fda.gov/scripts/cder/drugsatfda/index.cfm).

Expert Report of Leslie Hendeles Exhibit 102: *The Merck Index* (14th ed., 2006), pp. 389, 728, 736, 1488.

Expert Report of Leslie Hendeles Exhibit 105: Hess, D. et al., *Medication–Delivery Performance of Eight Small–Volume, Hand–Held Nebulizers: Effects of Diluent Volume, Gas, Flowrate and Nebulizer Model,* Respiratory Care (vol. 34, No. 8, Aug. 1989), pp. 717–723.

Expert Report of Leslie Hendeles Exhibit 108: *CRC Handbook of Chemistry and Physics* (Weast et al. eds., 1989–1990), p. D–163.

Expert Report of Paul Myrdal Exhibit 14: Allen, L.V., *Basics of Compounding Inhalation Preparations,* Int. J. Pharm. Compounding (vol. 4, No. 6, Nov./Dec. 2000), pp. 452–455.

Expert Report of Paul Myrdal Exhibit 15: Byron, P.R., *Respiratory Drug Delivery* (Byron, P.R. ed. 1990), pp. 143–165.

Expert Report of Paul Myrdal Exhibit 19: Connors, K.A. et al., *Chemical Stability of Pharmaceuticals: A Handbook for Pharmacists* (1979), pp. 17, 44–52, 123–167.

Expert Report of Paul Myrdal Exhibit 20: Ochsner, Martin et al., *Comparative biophysical analysis of the interaction of bronchodilating β2–adrenoceptor agonists with lipid membranes,* Eur. J. Med. Chem. (vol. 34, No. 6, 1999), pp. 451–462.

Expert Report of Paul Myrdal Exhibit 21: National Asthma Education and Prevention Program, *Expert Panel Report 2: Guidelines for the Diagnosis and Management of Asthma* (Jul. 1997).

Expert Report of Paul Myrdal Exhibit 46: *Physicians' Desk Reference* (52d ed., 1998), pp. 2368–2369; *Physicians' Desk Reference* (47th ed., 1993), pp. 2, 582–585,1556–1557; *Physicians' Desk Reference* (52d ed., 1998), pp. 102, 110, 787–788; *Physicians' Desk Reference* (54th ed., 2000), pp. 4, 790–791.

Expert Report of Paul Myrdal Exhibit 47: *Photostability of Drugs and Drug Formulations* (Tonnesen, H.H. ed., 1996), pp. 1–62, 111–154, 305–321.

Expert Report of Guirag Poochikian Exhibit 6: U.S. Dept. of Health and Human Services, *Guidance for Industry: Q1B Photostability Testing of New Drug Substances and Products* (Nov. 1996).

Expert Report of Guirag Poochikian Exhibit 13: U.S. Dept. of Health and Human Services, *Draft Guidance for Industry: Nasal Spray and Inhalation Solution, Suspension, and Spray Drug Products—Chemistry, Manufacturing, and Controls Documentations* (May 1999).

Expert Report of Guirag Poochikian Exhibit 14: *Draft Guidance for Industry on Nasal Spray and Inhalation Solution, Suspension, and Spray Drug Products; Chemistry, Manufacturing, and Controls Documentations; Availability Sterility Requirements for Inhalation Solution Products,* 64 Fed. Reg. 29,657 (Jun. 2, 1999).

Expert Report of Guirag Poochikian Exhibit 18: International Conference on Harmonization of Technical Requirements for the Registration of Pharmaceuticals for Human Use, *Harmonized Tripartite Guideline: Stability Testing of New Drug Substances and Products* (Oct. 27, 1993).

Expert Report of Guirag Poochikian Exhibit 19: *International Conference on Harmonisation; Stability Testing of New Drug Substances and Products; Guideline; Availability,* 59 Fed. Reg. 48,754 (Sep. 22, 1994).

Expert Report of Gordon Rausser, Ph.D, Apr. 28, 2011. [Confidential—Under Seal].

Expert Report of Leslie Hendeles Exhibit 25: Opinion in *AstraZeneca v. Apotex* in the United States District Court of New Jersey, Civil Action No. 1:09–cv–1518 (filed May 14, 2009). [Confidential—Under Seal].

Expert Report of Leslie Hendeles Exhibit 118.2: Claim Chart for U.S. Patent No. 6,667,344: Hochrainer et al. and Puigbo et al. [Confidential—Under Seal].

Expert Report of Leslie Hendeles Exhibit 118.3: Claim Chart for U.S. Patent No. 6,667,344: Murakami et al. and Gao et al. [Confidential—Under Seal].

Expert Report of Leslie Hendeles Exhibit 119.2: Claim Chart for U.S. Patent No. 6,814,953: Murakami et al. and Hochrainer et al. [Confidential—Under Seal].

Expert Report of Leslie Hendeles Exhibit 119.3: Claim Chart for U.S. Patent No. 6,814,953: Gao et al. and Whelan et al. [Confidential—Under Seal].

Expert Report of Leslie Hendeles Exhibit 120.2: Claim Chart for U.S. Patent No. 7,348,362: Murakami et al., Gavin et al., and Platz. [Confidential—Under Seal].

Expert Report of Leslie Hendeles Exhibit 121.2: Claim Chart for U.S. Patent No. 7,462,645: Murakami et al., Gavin et al., and Platz (Exhibit 103). [Confidential—Under Seal].

Expert Report of Leslie Hendeles, Pharm.D., Apr. 28, 2011. [Confidential—Under Seal].

Expert Report of Professor Paul B. Mydral, Ph.D., Apr. 28, 2011. [Confidential—Under Seal].

Expert Report of Guirag Poochikian Exhibit 11: Letter from Michele Carpenter to FDA submitting Original IND for Formoterol Fumarate Inhalation Solution, Serial No. 000, dated Dec. 15, 2003. [Confidential—Under Seal].

Expert Report of Guirag Poochikian, Ph.D., Apr. 27, 2011. [Confidential—Under Seal].

Expert Report of Leslie Hendeles Exhibit 46: Deposition Transcript of Stephen Pham, Ph.D., dated Jan. 21, 2011 in *Dey* v. *Teva* in the United States District Court for the Northern District of West Virginia, Civil Action No. 1:09–CV–0087. [Confidential—Under Seal].

Expert Report of Leslie Hendeles Exhibit 112: Transcript of Claim Construction Hearing on Mar. 3, 2011 in *Dev.* v. *Teva*. [Confidential—Under Seal].

Expert Report of Leslie Hendeles Exhibit 115: Deposition Transcript Dr. Imtiaz Chaudry dated Oct. 27, 2010 in *Dev.* v. *Teva*. [Confidential—Under Seal].

Expert Report of Paul Myrdal Exhibit 37: Pham, S., Formoterol Inhalation Unit Dose. [Confidential—Under Seal].

Expert Report of Paul Myrdal Exhibit 38: Formoterol Inhalation Unit Dose Study Description and Conclusions. [Confidential—Under Seal].

Expert Report of Paul Myrdal Exhibit 40: Email from Samuel Akapo to Imtiaz Chaudry dated Feb. 4, 2005, Formoterol Special Study Plan. [Confidential—Under Seal].

Expert Report of Paul Myrdal Exhibit 41: Email from Samuel Akapo to Imtiaz Chaudry dated Oct. 5, 2005, Final Report. [Confidential—Under Seal].

Expert Report of Paul Myrdal Exhibit 42: Akapo Lab Notebook AD–0369.[Confidential—Under Seal].

Expert Report of Paul Myrdal Exhibit 43: Akapo Email and stability data to Chaudry dated Jan. 1, 2006. [Confidential—Under Seal].

Expert Report of Paul Myrdal Exhibit 44: Pharmaceutical Development Report #PDR 716B Section 3 Reference. [Confidential—Under Seal].

Expert Report of Leslie Hendeles Exhibit 4: List of Materials Considered in Forming Opinion.

Expert Report of Paul Myrdal Exhibit 3: List of Materials Considered.

Expert Report of Guirag Poochikan Exhibit 1: List of Documents Reviewed.

Memorandum Opinion And Order Construing Patent Claims in *Dey* v. *Teva* in the United States District Court for the Northern District of West Virginia, Civil Action No. 1:09–cv–00087.

Maesen et al, "Formoterol suspension aerosol. Comparison with formoterol solution aerosol for 12 weeks in asthmatic patients," *Chest,* 102:1544–1549 (1992).

Lachman et al. *The Theory and Practice of Industrial Pharmacy,* by Lachman, Lieberman and Kanig, (3rd ed. 1986), Chapter 26: Kinetic Principles and Stability Testing, pp. 760–803.

Whelan et al, "Comparison of the Anti–Inflammatory Properties of Formoterol, Salbutamol, and Salmeterol in Guinea–Pig Skin and Lung," *British Journal of Pharmacology* 110, 613–18 (1993).

Remington, *The Science and Practice of Pharmacology,* $19^{th}$ Edition (1995), Chapter 38 "Stability of Pharmaceutical Products," pp. 639–647, vol. 1.

Wade et al., *Handbook of Pharmaceutical Excipients,* 2nd Ed. (1994), "Lecithin," pp. 267–268.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 61 is cancelled.

Claims 1, 5, 10, 22-26, and 39-43 are determined to be patentable as amended.

Claims 2-4, 6-9, 11-21, 27-38, 48, 62, 65 and 68-74, dependent on an amended claim, are determined to be patentable.

New claims 89-120 are added and determined to be patentable.

Claims 44-47, 49-60, 63, 64, 66, 67 and 75-88 were not reexamined.

1. A pharmecutical composition, comprising formoterol, or a derivative thereof, in a pharmacologically suitable [fluid] *aqueous solution*, wherein the composition is stable during long term storage, [the fluid comprises water, and] the composition is formulated at a concentration *effect for bronchodilation by nebulization, and the composition is* suitable for direct administration to a subject in need thereof, *without propellant and without dilution of the composition prior to administration*.

5. The pharmaceutical composition of claim 1, wherein the pharmacologically suitable [fluid] *aqueous solution* comprises a polar solvent.

10. The pharmaceutical composition of claim 1, wherein the pharmacologically suitable [fluid] *aqueous solution* comprises a buffer.

22. The pharmaceutical composition of claim 1, wherein the formoterol free base concentration is about 5 μg/mL to about [2 mg/mL] *50 μg/mL*.

23. The pharmaceutical composition of claim 22, wherein the formoterol free base concentration is about [10] *5* μg/mL to about [1 mg/mL] *10 μg/mL*.

24. The pharmaceutical composition of claim [23] *22*, wherein the formoterol free base concentration is about [50] *10* μg/mL to about [200 mg/mL] *50 μg/mL*.

25. The pharmaceutical composition of claim [24] *1*, wherein the formoterol free base concentration is about 59 μg/mL.

26. The pharmaceutical composition of claim [24] *1*, wherein the formoterol free base concentration is about 118 μg/mL.

39. The pharmaceutical composition of claim 27, wherein the formoterol free base concentration is about 5 μg/mL to about [2 mg/mL] *50 μg/mL*.

40. The pharmaceutical composition of claim 39, wherein the formoterol free base concentration is about [10] *5* μg/mL to about [1 mg/mL] *10 μg/mL*.

41. The pharmaceutical composition of claim [40] *39*, wherein the formoterol free base concentration is about [50] *10* μg/mL to about [200] *50* μg/mL.

42. The pharmaceutical composition of claim [41] *27*, wherein the formoterol free base concentration is about 59 μg/mL.

43. The pharmaceutical composition of claim [41] *27*, wherein the formoterol free base concentration is about 118 μg/mL.

*89. A pharmaceutical composition comprising a single unit dosage form, the dosage form comprising a single use container, the contents of the container comprising about 2 mL of an aqueous solution comprising formoterol, a pharmaceutically acceptable salt thereof, or hydrate of said formoterol or salt, wherein the concentration of said formoterol, salt, or hydrate is equivalent to about 5 μg/mL to about 50 μg/mL of formoterol free base in the solution, and the composition is suitable for direct administration by nebulization without dilution for bronchodilation to a subject in need thereof, and is stable during long term storage.*

*90. A composition according to claim 89, wherein the concentration of the formoterol, salt or hydrate is equivalent to about 5 μg/mL to about 10 μg/mL of formoterol free base in the solution.*

*91. A composition according to claim 89, wherein the concentration of the formoterol, salt or hydrate is equivalent to about 10 μg/mL to about 50 μg/mL of formoterol free base in the solution.*

*92. A pharmaceutical composition according to claim 89, wherein the salt is a tartrate.*

*93. A pharmaceutical composition according to claim 89, wherein the salt is a fumarate.*

*94. A pharmaceutical composition according to claim 89, wherein the nebulization is conducted in a jet nebulizer.*

*95. A pharmaceutical composition according to claim 89, wherein the subject is human.*

*96. A pharmaceutical composition as defined in claim 89, wherein the nebulization is conducted in an ultrasonic nebulizer.*

*97. A pharmaceutical composition as defined in claim 89, wherein the nebulization is conducted in an electromagnetic nebulizer.*

*98. A pharmaceutical composition according to claim 89 wherein the aqueous solution comprises a saline solution.*

*99. A pharmaceutical composition according to claim 98, wherein the saline solution is isotonic.*

100. A pharmaceutical composition according to claim 89, wherein the solution further comprises a citrate buffer.

101. A pharmaceutical composition according to claim 100, wherein the citrate buffer comprises sodium citrate.

102. A pharmaceutical composition according to claim 100, wherein the citrate buffer comprises citratic acid and sodium citrate.

103. A pharmaceutical composition according to claim 89, wherein the dosage form comprises an aqueous solution that is sterile.

104. A pharmaceutical composition according to claim 89, wherein the formoterol, salt or hydrate is provided as a mixture of enantiomers or stereoisomers of formoterol, or a salt or a hydrate thereof.

105. A pharmaceutical composition according to claim 89, wherein the formoterol, salt or hydrate is provided substantially as a single enantiomer or stereoisomer of formoterol, or a salt or a hydrate thereof.

106. A pharmaceutical composition according to claim 105, wherein the formoterol, salt, or hydrate provided substantially as a single enantiomer or stereoisomer optically pure.

107. A pharmaceutical composition according to claim 105, wherein the formoterol, salt, or hydrate consists of the free base, a salt or a hydrate of the enantiomer or stereoisomer
2-hydroxy-5-((1R)-1-hydroxy-2-(((1R)-2-(p-methoxyphenyl)-1-methylethyl)amino) ethyl) formanilide.

108. A pharmaceutical composition according to claim 106, wherein the formoterol, salt, or hydrate consists of the free base, a salt or a hydrate of the enantiomer or stereoisomer
2-hydroxy-5-((1R)-1-hydroxy-2-(((1R)-2-(p-methoxyphenyl)-1-methylethyl)amino) ethyl) formanilide.

109. A pharmaceutical composition according to claim 108, wherein the formoterol, salt, or hydrate consists of tartate salt of the enantiomer or stereoisomer
2-hydroxy-5-((1R)-1-hydroxy-2-(((1R)-2-(p-methoxyphenyl)-1-methylethyl)amino) ethyl) formanilide.

110. A pharmaceutical composition according to claim 108, wherein the formoterol, salt, or hydrate consists of a fumarate salt of the enantiomer or stereoisomer
2-hydroxy-5-((1R)-1-hydroxy-2-(((1R)-2-(p-methoxyphenyl)-1-methylethyl)amino) ethyl) formanilide.

111. A pharmaceutical composition according to claim 105, wherein the formoterol, salt or hydrate consists of a formoterol tartrate or a formoterol fumarate.

112. A pharmaceutical composition according to claim 111, wherein the formoterol, salt or hydrate consists of a formoterol fumarate dihydrate.

113. A pharmaceutical composition according to claim 111, wherein the formoterol, salt or hydrate consists of a formoterol tartrate.

114. A pharmaceutical composition comprising a single unit dosage form, the dosage form comprising a single use container, the contents of the container comprising about 2 mL of a sterile isotonic saline solution comprising a pharmaceutically acceptable salt of formoterol or a hydrate thereof and a citrate buffer, wherein the concentration of the formoterol salt is equivalent to about 5-50 µg formoterol free base per mL of solution, the dosage form is suitable for long term storage of the solution, and the solution does not require dilution before the administration by nebulization of a therapeutically effective amount for bronchodilation of the formoterol salt or hydrate to a human subject in need thereof.

115. A pharmaceutical composition according to claim 114, wherein the salt is a formoterol fumarate or a formoterol tartrate.

116. A pharmaceutical composition according to claim 115, wherein the salt is a formoterol fumarate dihydrate.

117. A pharmaceutical composition according to claim 115, wherein the salt is a formoterol tartrate.

118. A pharmaceutical composition comprising a single unit dosage form, the dosage form comprising a single use container, the contents of the container comprising about 2 mL of a sterile isotonic saline solution comprising a pharmaceutically acceptable salt of
2-hydroxy-5-((1R)-1-hydroxy-2-(((1R)-2-(p-methoxyphenyl)-1-methylethyl)amino)ethyl) formanilide (formoterol) or a hydrate thereof
and a citrate buffer,
wherein the concentration of the formoterol salt is equivalent to about 5-50 µg formoterol free base per mL of solution,
the dosage form is suitable for long term storage of the solution, and
the solution does not require dilution before the administration by nebulization of a therapeutically effective amount for bronchodilation of the formoterol salt to a human subject in need thereof.

119. A pharmaceutical composition according to claim 114, wherein the concentration of the formoterol salt is equivalent to about 5-10 µg formoterol free base per mL of solution.

120. A pharmaceutical composition according to claim 118, wherein the concentration of the formoterol salt is equivalent to about 5-10 µg formoterol free base per mL of solution.

* * * * *